US007790849B2

(12) United States Patent
Asada et al.

(10) Patent No.: US 7,790,849 B2
(45) Date of Patent: Sep. 7, 2010

(54) ENHANCEMENT OF RETROVIRAL GENE TRANSDUCTION EMPLOYING POLYPEPTIDES COMPRISING THE FIBRONECTIN HEPARIN II BINDING DOMAIN

(75) Inventors: Kiyozo Asada, Koka-gun (JP); Takashi Uemori, Otsu (JP); Takashi Ueno, Kusatsu (JP); Nobuto Koyama, Uji (JP); Kimikazu Hashino, Takatsuki (JP); Ikunoshin Kato, Uji (JP)

(73) Assignee: Takara Bio Inc. (JP)

( * ) Notice: Subject to any disclaimer, the term of this patent is extended or adjusted under 35 U.S.C. 154(b) by 28 days.

(21) Appl. No.: 12/241,581

(22) Filed: Sep. 30, 2008

(65) Prior Publication Data
US 2009/0209730 A1 Aug. 20, 2009

Related U.S. Application Data

(60) Division of application No. 11/181,091, filed on Jul. 14, 2005, now Pat. No. 7,446,170, which is a division of application No. 09/775,964, filed on Feb. 2, 2001, now Pat. No. 6,949,623, which is a division of application No. 08/809,156, filed on Mar. 7, 1997, now Pat. No. 6,472,204, which is a continuation-in-part of application No. PCT/JP96/03254, filed on Nov. 7, 1996.

(30) Foreign Application Priority Data

Nov. 13, 1995 (JP) ................................... 7-294382
Mar. 8, 1996 (JP) ................................... 8-051847

(51) Int. Cl.
C07K 14/00 (2006.01)
C07H 21/04 (2006.01)
(52) U.S. Cl. ................................... 530/350; 536/23.4
(58) Field of Classification Search ........................ None
See application file for complete search history.

(56) References Cited

U.S. PATENT DOCUMENTS

| 4,994,559 | A | 2/1991 | Moscatelli et al. |
| 5,026,839 | A | 6/1991 | Moscatelli et al. |
| 5,302,701 | A | 4/1994 | Hashi et al. |
| 5,399,346 | A | 3/1995 | Anderson et al. |
| 5,492,890 | A | 2/1996 | Ginsberg et al. |

FOREIGN PATENT DOCUMENTS

| EP | 0 207 751 A1 | 1/1987 |
| JP | 62-89699 A | 4/1987 |
| JP | 63-501953 A | 8/1988 |
| JP | 7-504812 A | 6/1995 |
| JP | 10029952 | 2/1998 |
| WO | WO 92/17210 A1 | 10/1992 |
| WO | WO 93/09221 A1 | 5/1993 |
| WO | WO 94/10323 A1 | 5/1994 |
| WO | WO 95/26200 A1 | 10/1995 |

OTHER PUBLICATIONS

Brown, T., 1993, Hybridization Analsis of DNA Blots, in Current Protocols in Molecular Biology, John Wiley and Sons, Inc., 2.10.1-2.10.16.*
Giovanni Paolella et al., "Sequence analysis and in vivo expression show that alternative splicing of ED-B and ED-A regions of the human fibronectin gene are independent events", Nucleic Acids Research, vol. 16, No. 8, 1988, pp. 3545-3557.
Bing Lim et al., "Long-term expression of human adenosine deaminase in mice transplanted with retrovirus-infected hematopoietic stem cells", Proc. Natl. Acad. Sci. USA, vol. 86, Nov. 1989, pp. 8892-8896.
Michael H. Ross, Ph.D. et al., *Histology: A Text and Atlas,* Williams & Wilkins, Baltimore, 1989, pp. 192-195.
Hiroshi Neda et al., "Chemical Modification of an Ecotropic Murine Leukemia Virus Results in Redirection of Its Target Cell Specificity", The Journal of Biological Chemistry, vol. 266, No. 22, Aug. 5, 1991, pp. 14143-14146.
Thomas M. Devlin, Ph.D., *Textbook of Biochemistry With Clinical Corrections,* Wiley-Liss, New York, 1992, pp. 1151-1154.
Gay M. Crooks et al., "Growth Factors Increase Amphotropic Retrovirus Binding to Human CD34+ Bone Marrow Progenitor Cells", Blood, vol. 82, No. 11, Dec. 1, 1993, pp. 3290-3297.
Hugo Soudeyns et al., "Identification of a Novel Glucocorticoid response Element within the Genome of the Human Immunodeficiency Virus Type 1", Virology, vol. 194, 1993, pp. 758-768.
Mariann Grossman et al., "Successful ex vivo gene therapy directed to liver in a patient with familial hypercholesterolaemia", Nature Genetics, vol. 6, Apr. 1994, pp. 335-341.
Thomas Moritz et al., "Bone Marrow Extracellular Matrix Molecules Improve Gene Transfer into Human Hernatopoietic Cells via Retroviral Vectors", J. Clin. Invest., vol. 93, Apr. 1994, pp. 1451-1457.
E.G. Nabel et al., "Recombinant growth factor gene expression in vascular cells in vivo", Annals of the New York Academy of Sciences, Apr. 18, 1994, 714:247-52.
Noriyuki Kasahara et al., "Tissue-Specific Targeting of Retroviral Vectors Through Ligand-Receptor Interactions", Science, vol. 266, Nov. 25, 1994, pp. 1373-1376.
E.L.W. Kittler et al., "Enhancement of Retroviral Integration by Cytokine Stimulation Impairs Engraftment of Bone Marrow Cells into Non-Myeloablated Hosts", Blood, vol. 84 (10 Suppl. 1), 1994, p. 344a (col. 1360).
Thomas Moritz, MD et al., "Gene transfer into the hematopoietic system", Current Science/Current Opinion in Hematology, 1994, pp. 423-428.

(Continued)

*Primary Examiner*—Jeffrey S. Parkin
(74) *Attorney, Agent, or Firm*—DLA Piper LLP (US)

(57) ABSTRACT

An isolated polypeptide includes the amino acid sequence shown in SEQ. ID No. 13 and an isolated nucleic acid encoding the polypeptide, such as an isolated nucleic acid including the nucleic acid sequence shown in SEQ. ID No. 17. The isolated polypeptide includes two heparin binding polypeptides connected in tandem and the isolated nucleic acid encodes these. The polypeptide and nucleic acid sequences can improve retroviral vector mediated gene transfer efficiency into target cells.

3 Claims, 26 Drawing Sheets

OTHER PUBLICATIONS

Akio Ido et al., "Gene Therapy for Hepatoma Cells Using a Retrovirus Vector Carrying Herpes Simplex Virus Thymidine Kinase Gene under the Control of Human αFetoprotein Gene Promoter", Cancer Research 55, Jul. 15, 1995, pp. 3105-3109.

Thierry Vandendriessche et al., "Inhibition of Clinical Human Immunodeficiency Virus (HIV) Type 1 Isolates in Primary CD4+ T Lymphocytes by Retroviral Vectors Expressing Anti-HIV Genes", Journal of Virology, vol. 69, No. 7, Jul. 1995, pp. 4045-4052.

Robin A. Weiss et al., "Retrovirus Receptors", Cell, vol. 82, Aug. 25, 1995, pp. 531-533.

Claudio Bordignon et al., "Gene Therapy in Peripheral Blood Lymphocytes and Bone Marrow for ADA-Immunodeficient Patients", Science, vol. 270, Oct. 20, 1995, pp. 470-474.

Donald B. Kohn, MD, "The current status of gene therapy using hematopoietic stem cells", Current Science/Current Opinion in Pediatrics, 1995, pp. 56-63.

Peter J. Quesenberry, "Hemopoietic stem cells, progenitor cells, and cytokines", *Williams Hematology*, Fifth Edition, McGraw-Hill, Inc., New York, 1995, pp. 211-215.

Christopher E. Walsh et al., "Gene therapy", *Williams Hematology*, Fifth Edition, McGraw-Hill, Inc., New York, 1995, pp. 195-199.

Helmut Hanenberg et al., "Colocalization of retrovirus and target cells on specific fibronectin fragments increases genetic transduction of mammalian cells", Nature Medicine, vol. 2, No. 8, Aug. 1996, pp. 876-882.

Thomas Moritz et al., "Fibronectin Improves Transduction of Reconstituting Hematopoietic Stem Cells by Retroviral Vectors: Evidence of Direct Viral Binding to Chymotryptic Carboxy-Terminal Fragments", Blood, vol. 88, No. 3, Aug. 1, 1996, pp. 855-862.

Thomas J. Wickham et al., "Targeted Adenovirus Gene Transfer to Endothelial and Smooth Muscle Cells by Using Bispecific Antibodies", Journal of Virology, vol. 70, No. 10, Oct. 1996, pp. 6831-6838.

John M. Coffin, "*Retroviridae*: The Viruses and Their Replication", *Fields Virology*, Third Edition, Lippincott-Raven Publishers, Philadelphia, 1996, pp. 1769-1771 and 1787-1791.

David M. Knipe, "Virus-Host Cell Interactions", *Fields Virology*, Third Edition, Lippincott-Raven Publishers, Philadelphia, 1996, pp. 275-279.

Valérie Dardalhon et al., "Green Fluorescent Protein as a Selectable Marker of Fibronectin-Facilitated Retroviral Gene Transfer in Primary Human T Lymphocytes", Human Gene Therapy, Jan. 1, 1999, pp. 5-14.

Scott S. Case et al., "Stable transduction of quiescent CD34+CD38− human hematopoietic cells by HIV-1-based lentiviral vectors", Proc. Natl., Acad. Sci. USA, vol. 96, Mar. 1999, pp. 2988-2993.

Vivienne I. Rebel et al., "One-Day Ex Vivo Culture Allows Effective Gene Transfer Into Human Nonobese Diabetic/Severe Combined Immune-Deficient Repopulating Cells Using High-Titer Vesicular Stomatitis Virus G Protein Pseudotyped Retrovirus", Blood, vol. 93, No. 7, Apr. 1, 1999, pp. 2217-2224.

Fern J. Bober Barkalow et al., "Localization of the Major Heparin-binding Site in Fibronectin," The Journal of Biological Chemistry, vol. 266, No. 12, Apr. 25, 1991, pp. 7812-7818.

\* cited by examiner

ENHANCEMENT OF RETROVIRAL GENE TRANSDUCTION EMPLOYING POLYPEPTIDES COMPRISING THE FIBRONECTIN HEPARIN II BINDING DOMAIN

This application is a divisional of Ser. No. 11/181,091, filed on Jul. 14, 2005, which is a divisional of Ser. No. 09/775,964, filed on Feb. 2, 2001 (now U.S. Pat. No. 6,949,623, issued Sep. 27, 2005), which is a divisional of Ser. No. 08/809,156, filed on Mar. 7, 1997 (now U.S. Pat. No. 6,472,204, issued Oct. 29, 2002), which is a continuation-in-part application of PCT. Application No. PCT/JP96/03254, filed on Nov. 7, 1996, which claims priority of Japanese Patent Application Nos. 294382/1995, filed Nov. 13, 1995, and 051847/1996, filed Mar. 8, 1996.

FIELD OF THE INVENTION

The present invention relates to a method for increasing the efficiency of gene transfer into target cells. The method permits efficient transformation of target cells in various technical fields such as medical science, cell technology, genetic engineering and developmental technology and a series of techniques relating thereto.

PRIOR ART

Owing to understanding in mechanisms of many human diseases as well as rapid progress in recombinant DNA technology and gene transfer technology, recently, protocols for somatic gene therapy have been developed for treating severe genetic diseases. In addition, currently, activities have been attempted to apply gene therapy to not only treatment of genetic diseases but also treatment of viral infections such as AIDS and cancers.

Almost all the gene transfer experiments in human being heretofore approved by Food and Drug Administration (FDA) are transduction of cells by recombinant retroviral vectors. Retroviral vectors can efficiently transfer a required exogenous gene into cells to stably integrate the exogenous gene into chromosomal DNA and therefore, especially, they are preferred gene transfer means for gene therapy wherein long term gene expression is desired. Such vectors are designed in various ways to avoid any adverse effect on transduced organisms. For example, replication, functions of vectors are lost to prevent unlimited repetition of infection (transduction) due to auto-replication of the vectors to be used for gene transfer into cells. Since these vectors (replication deficient retroviral vectors) have no capability of auto-replication, in general, retroviral vectors packaged in viral particles are prepared by using retrovirus producer cells (packaging cells).

On the other hand, bone marrow cells are a good target for somatic gene therapy because bone marrow cells are easily manipulated in vitro and contain hematopoietic stem cells capable of auto-replication. Alternatively, human cord blood has previously also been demonstrated to contain a large number of primitive progenitor cells including hematopoietic stem cells. When gene therapy is carried out by gene transfer into these target cells and grafting thereof in a living body, the gene thus transferred is expressed over long term in blood cells to effect lifelong cures for diseases.

However, in spite of intensive studies by various groups, hematopoietic stem cells are one of those whose efficient transduction is difficult. Heretofore, a most efficient gene transfer protocol relating to hematopoietic stem cells of mouse and other animals was co-culture of hematopoietic stem cells with retrovirus producer cells. However, for clinical gene therapy of human being, cell-free transduction is more desirable due to concerns about bio-safety. Unfortunately, efficient gene transfer into hematopoietic stem cells has generally not been possible without co-culture with retrovirus producer cells.

Recently, it has been reported that the gene transfer efficiency by retroviruses can be improved by a component of an extracellular matrix, fibronectin, or its fragments alone (J. Clin. Invest., 93, pp. 1451-1457 (1994); Blood, 88, pp. 855-862 (1996)). In addition, it has also been disclosed that fibronectin fragments produced by genetic engineering have the same properties and, by utilizing them, efficient transfer of an exogenous gene into hematopoietic stem cells can be carried out (WO 95/26200). Binding of a heparin binding domain of fibronectin to a retrovirus is suggested to be concerned in such improvement of the gene transfer efficiency by fibronectin. In all these methods utilizing fibronectin and fibronectin fragments, cells are infected with retroviruses in plates on which fibronectin or its fragment is immobilized.

OBJECTS OF THE INVENTION

The above-described gene transfer methods utilizing fibronectin and fibronectin fragments are considered to be achieved by fibronectin or its fragment molecules having both retrovirus binding domain and target cell binding domain on the same molecule (Nature Medicine, 2, pp. 876-872 (1996)). Therefore, for efficient gene transfer into various target cells by using the above-described method, it is necessary to prepare a functional material having both virus and target cell binding domains on one molecule according to respective particular cells and a problem still remains in the use thereof as a general gene transfer method.

Further, the above-described gene transfer method is carried out by immobilizing fibronectin or a fibronectin fragment on the surface of a plate to be used for culture of target cells upon infection of retroviruses. However, complicated procedures are required for immobilization on a plate and this is far from saying a simple and convenient gene transfer method.

Moreover, the functional material to be used in the above-described gene transfer method is limited to that containing a heparin binding domain derived from fibronectin as a retrovirus binding domain. Then, there are possibilities that an improved gene transfer method can be developed by finding out any other retrovirus binding substance.

The object of the present invention is to solve the problem and to provide a more convenient and efficient gene transfer method.

SUMMARY OF THE INVENTION

The present inventors have found that retrovirus infection by a functional material, typically, fibronectin or its fragment, can be promoted, even when a region having a retrovirus binding domain and a region having a cell binding domain are not present on the same molecule. That is, the present inventors have found that the efficiency of gene transfer into target cells by retroviruses can be improved by using an effective amount of a functional material containing a retrovirus binding domain admixed with a functional material having a target cell binding domain.

In addition, the present inventors have also found that retrovirus infection enhancing activity by a functional material can be observed even when the functional material is not immobilized on a surface of a plate. The present inventors have further found that the efficiency of gene transfer into target cells can be improved by contacting retroviruses with the target cells in the presence of a functional material immobilized on beads.

In addition, the present inventors have further found a retrovirus binding substance which does not contain a heparin binding domain derived from fibronectin and also found that the material and derivatives thereof are useful for gene transfer into target cells with retroviruses. Moreover, the present inventors have succeeded in creation of functional materials useful for gene transfer into target cells with retroviruses. Thus, the present invention has been completed.

Then, the first aspect of the present invention relates to a method for increasing the efficiency of gene transfer into target cells with retroviruses. The method is directed to transduction of target cells with, a retrovirus and is characterized by infecting the target cells with the retrovirus in the presence of a mixture of an effective amount of a functional material having retrovirus binding domain, and an effective amount of another functional material having target cell binding domain to permit transfer of the gene into the target cells.

The functional material having retrovirus binding domain used in the first aspect of the present invention is not specifically limited and, for example, it is a functional material selected from the group consisting of the Heparin-II binding domain of fibronectin, a fibroblast growth factor, a collagen, a polylysine and functional equivalents thereof. The functional material having target cell binding domain may be a substance containing a ligand which can bind to target cells. As the ligand, there are cell adhesion proteins, hormones, cytokines, antibodies, sugar chains, carbohydrates and metabolites of target cells and the like. Examples of adhesion proteins include polypeptides of a cell binding domain of fibronectin. As the cell binding domain of fibronectin, there are polypeptides of binding domain to VLA-5 and/or VLA-4. Further, other examples of ligand include erythropoietin.

The functional material to be used in the first aspect of the present invention may be used without immobilization or may be immobilized and, when they are immobilized on beads, they can be used conveniently. In addition, when a ligand specific for target cells is selected as the functional material having target cell binding domain, the first aspect of the present invention permits convenient transduction of intended target cells.

As described above, in the conventional methods as disclosed in WO 95/26200 and Nature Medicine, it is consider to be an essential mechanism for improving the gene transfer efficiency into target cells with a retrovirus to co-localize the retrovirus and the target cells on a functional material having both retrovirus binding domain and target cell binding domain on the same molecule. However, according to the present invention, the efficiency of gene transfer into target cells can be improved by carrying out gene transfer into the target cells with a retrovirus in the presence of a mixture of an effective amount of a functional material having retrovirus binding domain and an effective amount of another functional material having target cell binding domain.

The second aspect of the present invention relates to a culture medium for target cells to be used for gene transfer into the target cells with retroviruses which comprises a mixture of an effective amount of a functional material having retrovirus binding domain, and an effective amount of another functional material having target cell binding domain.

By using the culture medium of the second aspect of the present invention, the first aspect of the present invention can be carried out conveniently.

The third aspect of the present invention relates to a localization method of retroviruses and the method is characterized by incubating a culture medium containing a retrovirus contacted with a mixture of an effective amount of a functional material having retrovirus binding domain, and an effective amount of another functional material having target cell binding domain.

The fourth aspect of the present invention relates to a kit to be used for carrying out retrovirus-mediated gene transfer into target cells and the kit comprises:

(a) an effective amount of a functional material having retrovirus binding domain and/or an effective amount of another functional material having target cell binding domain;

(b) an artificial substrate for incubating target cells and a retrovirus; and (c) a target cell growth factor for pre-stimulating the target cells.

By using the reagent kit of the fourth aspect of the present invention, the first and third aspects of the present invention can be carried out conveniently.

The fifth aspect of the present invention relates to a method for improving the gene transfer efficiency into target cells with retroviruses and the method is characterized by infecting the target cells with a retrovirus in the presence of an effective amount of a functional material having a target cell binding domain as well as a retrovirus binding domain derived from a fibroblast growth factor, a collagen or a polylysine, or a functional equivalent thereof on the same molecule to permit transduction of the target cells.

In the above conventional methods as described in WO 95/26200 and Nature Medicine, fibronectin fragments are disclosed as the material which can be used in a most efficient method for improving gene transfer into target cells with retroviruses. However, regarding functional materials other than fibronectin fragments, there is no specific disclosure about what kind of a functional material can be used in an efficient method for gene transfer into target cells with retroviruses. More specifically, in the conventional method, only the repeat 12-14 of fibronectin is disclosed as the retrovirus binding domain.

The present inventors have unexpectedly found that a fibroblast growth factor, a collagen, a polylysine and so on which do not have any structural relation to the repeat 12-14 of fibronectin can be effectively used in a method for improving gene transfer into target cells with retroviruses. Therefore, any functional equivalent of these materials, i.e., any material which has a retrovirus binding domain functionally equivalent to these materials and can improve the gene transfer efficiency into target cells with retrovirus can be used in the fifth aspect of the present invention.

In the fifth aspect of the present invention, as the target cell binding domain, a material having a ligand which can bind to target cells can be used and this material is coupled to the retrovirus binding domain.

Examples of the ligand include cell adhesion proteins, hormones, cytokines, antibodies, sugar chains, carbohydrates, metabolites of target cells and the like. Examples of cell adhesion proteins include polypeptides of a cell binding domain of fibronectin. For example, polypeptides of binding domain to VLA-5 and/or VLA-4 can be used in the present invention. Further, other examples of ligand include erythropoietin.

In the fifth aspect of the present invention, as the fibroblast growth factor to be used as the retrovirus binding domain, there are fibroblast growth factors selected from, for example, a fibroblast growth factor represented by SEQ. ID No. 3 of the Sequence Listing, functional equivalents of the factor and polypeptides containing the factor or functional equivalents thereof.

Examples of these functional materials include polypeptides containing an amino acid sequences represented by SEQ. ID Nos. 4 and 5 of the Sequence Listing.

In the fifth aspect of the present invention, collagens to be used as the retrovirus binding domain include, for example, collagens selected from a collagen fragment containing an insulin binding domain derived from type V collagen, functional equivalents of the fragments and polypeptides containing the fragments or functional equivalents thereof. In addition, examples of the fragments include a fragment containing an amino acid sequence represented by SEQ. ID No. 6 of the Sequence Listing.

Examples of these functional materials include polypeptides represented by SEQ. ID Nos. 7 and 8 of the Sequence Listing.

In the fifth aspect of the present invention, the polylysine to be used as the retrovirus binding domain is a polymer of L-lysine and, for example, one having a suitable polymerization degree can be selected from commercially available products and used.

If the retrovirus binding domain derived from a fibroblast growth factor, a collagen or a polylysine has a target cell binding domain, simultaneously, the gene transfer efficiency into target cells with a retrovirus can be improved by infecting the target cells with the retrovirus in the presence of an effective amount of the retrovirus binding domain derived from the fibroblast growth factor, the collagen or the polylysine. If target cells are adhesion cells, a retrovirus and target cells respectively bind to and adhere to the functional material, and the gene transfer efficiency into the target cells with the retrovirus can be improved by infecting the target cells with the retrovirus in the presence of an effective amount of the retrovirus binding domain derived from the fibroblast growth factor, the collagen or the polylysine.

It has also been found that, if a polypeptide represented by SEQ. ID No. 1 of the Sequence Listing (hereinafter referred to as H-271) has a target cell binding domain, simultaneously, that is, if target cells bind to the polypeptide, H-271, the gene transfer efficiency into the target cells with a retrovirus can be improved by infecting the target cells with the retrovirus in the presence of an effective amount of the polypeptide.

That is, although the retrovirus binding domain disclosed in the above Nature Medicine is only the repeat 12-14 of fibronectin, the present inventors have unexpectedly found that this H-271 effectively acts as a target cell binding domain according to a particular kind of target cells to improve the gene transfer efficiency into the target cells. In addition, in case that target cells are adhesion cells, the target cells and a retrovirus bind and adhere to the polypeptide, respectively, and the gene transfer efficiency into the target cells with the retrovirus can be improved by infecting the target cells with the retrovirus in the presence of an effective amount of the polypeptide.

In the fifth aspect of the present invention, the functional material may be used without immobilization or may be immobilized, though immobilization is preferred in case that target cells are adherent cells.

The sixth aspect of the present invention relates to a culture medium for target cells to be used for gene transfer into the target cells with a retrovirus which comprises an effective amount of a functional material which has a target cell binding domain as well as a retrovirus binding domain derived from a fibroblast growth factor, a collagen or a polylysine, or a functional equivalent thereof on the same molecule.

The seventh aspect of the present invention relates to a localization method of a retrovirus which comprises incubating a culture medium containing the retrovirus contacted with a effective amount of a functional material containing a retrovirus binding domain derived from a fibroblast growth factor, a collagen or a polylysine. These functional materials can be efficiently used in localization of a retrovirus for improvement of gene transfer into target cells with the retrovirus.

Moreover, the localization method of a retrovirus of the present invention include incubation of the retro virus contacted with an effective amount of a functional material comprising a target cell bind domain as well as a retrovirus binding domain derived from a fibroblast growth factor, a collagen or a polylysine, or a functional equivalent thereof on the same molecule.

The eighth aspect of the present invention is a kit to be used for carrying out retrovirus-mediated gene transfer into target cells and the kit comprises:

(a) an effective amount of a functional material having a retrovirus binding domain as well as a target cell binding domain derived from a fibroblast growth factor, a collagen or a polylysine or a functional equivalent thereof on the same molecule;

(b) an artificial substrate for incubating target cells contacted with a retrovirus; and (c) a target cell growth factor for pre-stimulating the target cells.

For practicing any method of the first and fifth aspects, any culture medium of the second and sixth aspects, any method of the third and seventh aspects and any kit of the fourth and eighth aspects of the present invention, the functional materials immobilized on beads can be suitably used.

The ninth aspect of the present invention relates to a method for improving the gene transfer efficiency into target cells with a retrovirus and characterized in that the target cells are infected with the retrovirus in the presence of an effective amount of a functional material immobilized on beads selected from substantially pure fibronectin, a substantially pure fibronectin fragment or a mixture thereof to permit transduction of the target cells with the retrovirus.

The tenth aspect of the present invention also relates to a method for improving the gene transfer efficiency into target cells with a retrovirus and characterized in that the target cells are infected with the retrovirus in the presence of an effective amount of a functional material selected from substantially pure fibronectin, a substantially pure fibronectin fragment or a mixture thereof without immobilization to permit transduction of the target cells with the retrovirus.

In the above conventional methods as disclosed in WO 95/26200 and Nature Medicine, it is an essential mechanism for improving the gene transfer efficiency with a retrovirus that the retrovirus and the target cells should be co-localized on a functional material having a retrovirus binding domain and a target cell binding domain on the same molecule. In these methods, the co-localization of both retrovirus and target cells on the functional material having both retrovirus binding domain and target cell binding domain on the same molecule firstly becomes possible by immobilizing the functional material having the retrovirus binding domain and the target cell binding domain on the same molecule on a culture substrate.

However, according to the present invention, even when substantially pure fibronectin, a substantially pure fibronectin fragment or a mixture thereof is used, unexpectedly, the gene transfer efficiency into target cells with a retrovirus can be efficiently improved by using the functional material having both retrovirus binding domain and target cell binding domain on the same molecule without immobilization on a culture substrate.

As the target cells to be used in the first, fifth, ninth and tenth aspects of the present invention, there can be used, for example, cells selected from stem cells, hematopoietic cells, non-adherent low density mononuclear cells, adherent cells, bone marrow cells, hematopoietic stem cells, peripheral blood stem cells, umbilical blood cells, fetal hematopoietic stem cells, embryoplastic stem cells, embryonic cells, primordial germ cells, oocyte, oogonia, ova, spermatocyte, sperm, CD 34+cells, C-kit+cells, multipotential hemopoietic progenitor cells, unipotential hemopoietic progenitor cells, erythrocytic precursor cells, lymphocytic precursor cells, mature blood cells, lymphocytes, B cells, T cells, fibroblast, neuroblast, nerve cells, endothelial cells, angio-endothelial cells, hepatic cells, myoblast, skeletal muscle cells, smooth muscle cells, cancer cells, myeloma cells and leukemia cells.

As the retrovirus to be used in the first, third, fifth, seventh, ninth and tenth aspects of the present invention, a retrovirus containing an exogenous gene can be used and the retrovirus may be, for example, a recombinant retroviral vector. Further, the retrovirus may be, for example, a replication deficient recombinant retroviral vector.

The eleventh aspect of the present invention relates to transduced cells obtained by the first, fifth, ninth or tenth aspect of the present invention.

The twelfth aspect of the present invention relates to a cell grafting method for grafting the transduced cells of the eleventh aspect of the present invention into a vertebrate animal.

The thirteenth aspect of the present invention relates to a polypeptide represented by SEQ. ID No. 13 of the Sequence Listing which can improve the gene transfer efficiency into target cells with a retrovirus, or functional equivalents thereof.

The fourteenth aspect of the present invention relates to a gene encoding the polypeptide of the thirteenth aspect of the present invention. Examples of the gene include a gene represented by SEQ. ID No. 17 of the Sequence Listing or a gene which can hybridize to the above gene under stringent conditions and encode a polypeptide which can improve the gene transfer efficiency into target cells with a retrovirus.

In the above conventional methods of WO 95/26200 and Nature Medicine, the most efficient peptide to be used for the gene transfer is CH-296. On the other hand, the present inventors have unexpectedly found that the same polypeptide without VLA-5 binding domain and VLA-4 binding domain can be used in the present invention.

The fifteenth aspect of the present invention relates to a polypeptide represented by SEQ. ID No. 30 of the Sequence Listing which can improve a gene transfer efficiency into target cells with a retrovirus, or its functional equivalent.

The sixteenth aspect of the present invention relates to a gene encoding the polypeptide of the fifteenth aspect of the present invention. Examples of the gene includes a gene represented by SEQ. ID No. 33 of the Sequence Listing or a gene which can hybridize to the above gene under stringent conditions and encode a polypeptide which can improve the gene transfer efficiency into target cells with a retrovirus.

The seventeenth aspect of the present invention relates to a polypeptide represented by SEQ. ID No. 5 which can improve the gene transfer efficiency into target cells with a retrovirus, or functional equivalents thereof.

The eighteenth aspect of the present invention relates to a gene encoding the polypeptide of the seventeenth aspect of the present invention. Examples of the gene include a gene represented by SEQ. ID No. 26 or a gene which can hybridize to the above gene and encode a polypeptide which can improve the gene transfer efficiency into target cells with a retrovirus.

DETAILED DESCRIPTION OF THE INVENTION

For the gene transfer method of the present invention, usually, recombinant retroviral vectors are used and, in particular, a replication deficient retroviral vector is suitable. The capability of replication of the vector is lost to prevent auto-replication in infected cells, so the vector is non-pathogenic. These vectors can invade into host cells such as vertebrate animal cells, in particular, mammalian cells to stably integrate exogenous genes inserted into the vectors in chromosomal DNA of host cells.

In the present invention, an exogenous gene to be transferred into cells can be used by inserting it into a retroviral vector under the control of a suitable promoter, for example, a promoter of LTR present in a retrovirus or an exogenous promoter. In addition, in order to achieve transcription of an exogenous gene, other regulatory-elements which can cooperate with a promoter and a transcription initiation site, for example, an enhancer, can also be present in a vector. Moreover, preferably, an inserted gene can have a terminator sequence at its downstream. The exogenous gene to be transferred into cells can be natural or artificial ones, and can have additional DNA molecule derived from heterologous sources coupled thereto by ligation or other means known to the art.

The exogenous genes inserted into a retrovirus can be any genes of interest for transduction of the cells. For example, the exogenous genes can encode an enzyme which is associated with a disorder to be treated, a protein, an antisense nucleic acid, a ribozyme or a false primer (see, e.g. WO 90/13641), an intracellular antibody (see, e.g. WO 94/02610), a growth factor or the like.

The retroviral vectors to be used in the present invention can have a marker gene so that transduced cells can be readily selected. As the marker gene, for example, a drug resistant gene which provides transformant cells with antibiotic resistance or a reporter gene which provides transformant cells with an enzyme activity for detection thereof can be used.

As the vectors to be used, there are retroviral vectors such as known MFG vector (ATCC No. 68754), α-SGC (ATCC No. 68755) and the like. In addition, both N2/ZipTKNEO vector (TKNEO, Blood, Vol. 78, pp. 310-317 (1991)) and PM5neo vector (Exp. Hematol., Vol. 23, pp. 630-638 (1995)) used in the examples hereinafter contain neomycin resistant genes (neomycin phosphotransferase gene) as their marker genes. Then, cells transformed with these vectors can be recognized as cells having resistance to antibiotics (neomycin, G418, etc.) which are inactivated by the gene products. Moreover, these vectors can be prepared as virus particles containing the vectors packaged therein by using known packaging cell strains, for example, PG13 (ATCC CRL-10686), PG13/LNc8 (ATCC CRL-10685), PA317 (ATCC CRL-9078), cell strains described in U.S. Pat. No. 5,278,056, GP+E-86 (ATCC CRL-9642), GP+envAm-12 (ATCC CRL-9641) and the like.

The term "effective amount" of the functional material used herein means the amount required for transformation of target cells in gene transfer to target cells with a retrovirus. The amount can be selected depending upon a particular functional material, a retrovirus and a particular kind of target cells by using the method described herein. The terms "the gene transfer efficiency" used herein means the transformation efficiency.

The capability of binding to retroviruses of the functional material, i.e., effectiveness and usefulness of the functional material in the present invention can be ascertained by routine assays as disclosed in Examples hereinafter.

These assays determine the extent to which retrovirus particles are bound to the functional material immobilized to the matrix to be used in the present invention so as to resist washing from the matrix. Briefly, for example, a virus-containing supernatant can be incubated in a well containing the immobilized functional material having a retrovirus binding domain. The well is then thoroughly washed with a physiological saline buffer and thereafter, target cells are incubated in the well to determine the level of infectious activity of the virus remaining in the well. The reduction in infectious activity, or titer, relative to the initial viral supernatant is assessed and compared to that of a similar control (e.g. using a BSA-coated well). A significantly higher titer remaining in the functional material containing well as compared to the control well indicates that the material can be used as the functional material in the present invention.

To facilitate this screening procedure, the viral vector can contain a selectable marker gene.

The functional material having retrovirus binding domain to be used in the present invention can be screened by these assays.

As such a functional material having retrovirus binding domain, there is a functional material which has a retrovirus binding domain derived from Heparin-II binding domain of fironectin, a fibroblast growth factor, a collagen or a polylysine.

The binding of a cell binding domain of the functional material to be used in the present invention to cells, i.e., binding of a material containing a target cell binding ligand to cells can likewise be assayed using conventional procedures. For example, such procedures include those described in Nature 352: 438-441 (1991).

Briefly, the functional material having cell binding domain is immobilized on a culture plate and the cell population to be assayed is overlaid in a medium, followed by incubation for 30 minutes to 2 hours. After this incubation period, cells non-adherent to the functional material are retrieved, counted and assayed for viability. Cells adherent to the functional material are also retrieved using trypsin or cell dissociation buffer (e.g. Gibco), counted and viability tested. In some cases, for example for hematopoietic colony forming cells, the cells are further cultured for an additional 12 to 14 days to ascertain the colony forming characteristics of the cells. The percentage of adherent cells is then calculated and compared to a standard or standard control such as bovine serum albumin (BSA) immobilized on a culture plate. Substantial binding of the target cells to the assayed functional substance provides an indication that the functional material/cell combination is suitable for the present invention and the functional material having cell binding domain can co-exist with or be coupled to the functional material having retrovirus binding domain, followed by assessing retrovirus infection of the target cells to construct the functional material to be used in the present invention.

As the functional material having retrovirus binding domain which can be used in the present invention, as described above, there is a functional material which has a retrovirus binding domain derived from Heparin-II binding domain of fironectin, a fibroblast growth factor, a collagen or a polylysine. All substances which have a retrovirus binding domain equivalent to the above and can improve the gene transfer efficiency into target cells with retroviruses by coupling to or co-existing with a ligand having target cell binding domain are included in the functional equivalents to the retrovirus binding domain derived from a fibroblast growth factor, a collagen or a polylysine.

The effective amount of the functional material(s) to be used in the present invention can be determined by using target cells and a retrovirus in the gene transfer method of the present invention in the presence of the selected functional material having retrovirus binding domain coupled to or coexisting with the functional material having target cell binding domain and assessing improvement of the gene transfer efficiency according to the above-described method.

Hereinafter, the present invention will be illustrated in detail.

One aspect of the present invention is a method for improving the gene transfer efficiency into target cells with a retrovirus. This method is characterized by infecting viable target cells with a retrovirus in the presence of a mixture of the functional material having retrovirus binding domain and the functional material having target cell binding domain which is effective for improving the gene transfer efficiency into the target cells with the retrovirus.

This method can be used for obtaining transformant cells transduced with the retrovirus and grafting the cells into an individual organism permits gene transfer into an individual organism.

The functional material having retrovirus binding domain to be used in this method is not specifically limited and examples thereof include Heparin-II binding domain of fibronectin, a fibroblast growth factor, a collagen, a polylysine and the like. Likewise, functional equivalents thereof, for example a functional material having a heparin binding domain can also be used. In addition, a mixture of the functional materials, a polypeptide containing the functional material, a polymer of the functional material, a derivative of the functional material and the like can also be used. These functional materials can be obtained from naturally occurring products, or artificially produced (e.g., produced by genetic engineering techniques or chemical syntheses). Further, they can be produced by combining naturally occurring products with artificial products.

In so far as the retrovirus binding domain and/or target cell binding domain which can achieve gene transfer with the high efficiency as described herein are maintained, the functional material to be used may be those having mutation in amino acid sequences of naturally occurring polypeptides. In the present invention, even if deletion, substitution, insertion and/or addition of one or plural, for example, up to several amino acids are present in the amino acid sequences of naturally occurring polypeptides, in so far as the desired retrovirus binding domain and/or target cell binding domain are maintained, such polypeptides are referred to as functional equivalents of the polypeptides having naturally occurring amino acid sequences. These functional equivalents can be obtained by preparing genes encoding the functional equivalents to produce the equivalents and ascertaining their biological activities.

In this regard, the pertinent biotechnology arts have already advanced to a state in which the deletion, substitution, addition or other modifications of amino acids in the required functional domains can be routinely carried out. Then, the resultant amino acid sequences can be routinely screened for the desired cell binding activity or virus binding activity.

A gene encoding the functional equivalent can be obtained by searching for genes hybridizable to the gene encoding the above functional material.

That is, the gene encoding the above functional material or a part of its nucleotide sequence can be used as a probe of hybridization or primers of a gene amplification method such as PCR or the like to screen a gene encoding a protein having a similar activity to the functional material. Sometimes, in this method, a DNA fragment containing only a part of the desired gene is obtained. In such case, after ascertaining that the resultant DNA fragment is a part of the desired gene, the whole desired gene can be obtained by carrying out hybridization with the DNA fragment or a part thereof as a probe or carrying out PCR with primers synthesized based on the nucleotide sequence of the DNA fragment.

The above hybridization can be carried out, for example, under the following conditions.

That is, a membrane on which DNA is immobilized is incubated in 6×SSC (1×SSC: 0.15M NaCl, 0.015M sodium citrate, pH 7.0) containing 0.5% of SDS, 0.1% of BSA, 0.1% of polyvinyl pyrrolidone, 0.1% of Ficoll 400 and 0.01% of denatured salmon sperm DNA together with a probe at 50° C. for 12 to 20 hours. After completion of incubation, the membrane is washed with, firstly, 2×SSC containing 0.5% of SDS at 37° C. and then with changing the concentrations of SSC to 0.1×SSC and temperatures to 50° C. until the signal derived from the immobilized DNA can be distinguished from the background.

In addition, whether or not the resultant gene thus obtained is the desired one can be ascertained by examining the activity of the protein encoded by the resultant gene according to the above method.

As described in the above WO 95/26200, Heparin-II binding domain of fibronectin is the polypeptide having a retrovirus binding domain. Although a fibroblast growth factor, a collagen and a polylysine do not have any structural similarity to Heparin-II binding domain of fibronectin (e.g., similarity of amino acid sequences), the present inventors have found that these substances have retrovirus binding domains.

The functional material having target cell binding domain to be used in the present invention is not specifically limited, either, and is a substance having a ligand which can bind to target cells. Examples of the ligand include cell adhesion proteins, hormones, cytokines, antibodies against antigens on cell surfaces, polysaccharides, sugar chains in glycoproteins or glycolipids, metabolites of target cells and like. In addition, there can be used polypeptides containing the functional materials, polymers of the functional materials, derivatives of the functional materials, functional equivalents of the functional materials and the like. These functional materials can be obtained from naturally occurring products or artificially produced (e.g., produced by gene engineering techniques or chemical synthetic techniques). Further, they can be produced by combining naturally occurring products with artificially products.

Cell adhesion proteins to be used are, for example, fibronectin and its fragments. For example, the cell binding domain of human fibronectin which corresponds to Pro$^{1239}$-Ser$^{1515}$, as described in U.S. Pat. No. 5,198,423, has been shown to have the function equivalent to the polypeptide C-274 disclosed herein and to bind to cells including BHK and B16-F10 cells (Kimizuka et al., J. Biochem. Vol., 110, pp. 285-291 (1991)). A sequence composed of four amino acids of RGDS present in these polypeptides is a ligand for VLA-5 receptor. Expression of VLA-5 receptor is observed in a wide variety of cells and it is expressed in undifferentiated cells better than in differentiated cells. In addition, CS-1 region of fibronectin is known to be a ligand for VLA-4 receptor and binds to cells expressing the receptor (T cells, B cells, monocytes, NK cells, acidophiles, basophiles, thymocytes, myelomonocytic cells, erythroblastic precursor cells, lymphocytic precursor cells, melanoma, muscle cells and the like). The polypeptide described in JP-A 3-284700 and represented by SEQ. ID No. 29 (hereinafter referred to as C277-CS1) is a polypeptide having ligands for both above VLA-5 and VLA-4 receptors and can be used for gene transfer into cells having these receptors. Moreover, it has been shown that Heparin-II domain can bind to fibroblasts, endothelial cells and tumor cells. The polypeptide sequence of the cell binding domain of Heparin-II domain is useful for directing retrovirus infection toward targeted cells in the presence of a polypeptide of the functional material having retrovirus binding domain.

Hormones and cytokines having cell specific activities are suitable as the functional material having cell binding domain in the present invention. For example, erythropoietin which is a cytokine in the hematopoietic system can be used for gene transfer into erythrocytic cells. Erythropoietin can be prepared according to a known method and used in addition, functional equivalents of the erythropoietin and polypeptides containing erythropoietin or functional equivalents thereof can also be used.

As described in Examples hereinafter, when the functional material having retrovirus binding activity (e.g., H-271 and a fibroblast growth factor) is used in admixed with C-274 which is a polypeptide having a cell binding activity derived from fibronectin or the like, the high gene transfer efficiency can be obtained. NIH/3T3 cells which are used in these experiments express VLA-5 receptor which can bind to C-274 and the interaction of them contribute to improvement of the gene transfer efficiency.

Further, the same phenomenon is also observed, when an erythropoietin derivative is present in gene transfer into TF-1 cells which express erythropoietin receptor (Blood, Vol. 73, pp. 375-380 (1989)). Moreover, this effect is not observed in cells which do not have any erythropoietin receptor.

From these results, it is clear that cell specific increase in the gene transfer efficiency takes place in the presence of the functional material having retrovirus binding domain together with the functional material having cell binding domain.

In this aspect of the present invention, the functional material having retrovirus binding domain is used in the form of a mixture with another functional material having target cell binding domain. Thereby, the gene transfer efficiency into target cells having affinity to the functional materials is remarkably improved. Since the gene transfer efficiency is improved, co-culture with virus producer cells can be avoided and this is one of advantages of the present invention.

Means for selective gene transfer into target cells has high utility and various studies have been done. For example, there is non-viral vector (molecular conjugation vector) wherein a material binding to a receptor present on a cell surface is coupled to a DNA binding material. Examples of gene transfer using such a vector include gene transfer into hepatoma cells with asialoglycoprotein (J. Biol. Chem., Vol. 262, pp. 4429-4432 (1987)), gene transfer into lymphoblasts with transferrin (Proc. Natl. Acad. Sci. USA, Vol. 89, pp. 6099-6103 (1992)), gene transfer into cancer cells with anti EGF receptor antibody (FEBS Letters, Vol. 338, pp. 167-169 (1994)) and the like. These gene transfer methods using non-viral vectors are undesirable from the viewpoint of long term gene expression of transferred genes because the transferred genes are not integrated into chromosomal DNA of cells. Activities have been attempted to use retroviruses which are widely used as vectors capable of insertion of genes into chromosomes to infect specific cells. For examples, gene transfer into hepatocytes by direct chemical modification of retroviruses to couple to lactose (J. Biol. Chem., Vol. 266, pp. 14143-14146 (1991)), gene transfer into erythropoietin receptor-expressing cells by utilizing recombinant viral particles having an envelope protein which is a fused protein with erythropoietin (Science, Vol. 266, pp. 1373-1376 (1994)) and the like have been developed. However, for this purpose, it is necessary to prepare special protein particles according to particular target cells. In addition, chemical modification of viral particles requires complicated procedures and is liable to inactivate viruses. Moreover, regarding a virus envelope modified by gene engineering, the desired product having required functions (binding to target cells and construction of viral particles) is not always, obtained.

The above WO 95/26200 suggests that a retroviral vector without any special modification can be transferred into cells in the presence of a fibronectin fragment to which a suitable ligand having cell binding activity is covalently coupled. However, this method uses a functional molecule having both virus binding activity and cell binding activity and therefore an individual special functional material should be prepared according to particular kinds of cells. In addition, it is unknown whether or not the functional material prepared maintains both activities.

The combination of the functional material having retrovirus binding domain and the different functional material having target cell binding domain of the present invention can provide a gene delivery system using retroviruses for a wide variety of cell species. For this purpose, the functional material having retrovirus binding domain does not need to be covalently coupled to the functional material having cell binding domain. Therefore, there is no need to prepare an individual special functional material wherein the functional material having retrovirus binding domain is covalently coupled to the functional material having cell binding domain according to particular kinds of cells and gene transfer into target cells can be conveniently and efficiently carried out.

Examples of gene transfer into target cells using the method of the present invention is gene transfer into cells of the hematopoietic system. It has been known that the above CS-1 cell adhesion region of fibronectin is useful for gene transfer into hematopoietic stem cells. Further, it has, also been known that, in addition to the above erythropoietin, various other cell specific cytokines are concerned in differentiation of hematopoietic cells, and gene transfer can be carried out specifically into target cells (cell lines) by utilizing them. For example, when G-CSF is used, megakaryoblasts and granulocytic precursor cells can be used as the target cells of transduction.

When using a substance which specifically or predominantly binds to malignant cells as the functional material having cell binding domain, gene transfer into such target cells can be carried out.

For example, it has been known that receptors named as HER-2 and HER-4 are expressed in certain breast carcinoma cells (Proc. Nat. Acad. Sci. USA, Vol. 92, pp. 9747-9751 (1995)). Accordingly, it is possible to control growth of breast carcinoma cells by combining heregulin which is a ligand for the receptors with the functional material having retrovirus binding domain.

In addition, by using the functional material containing iodine for thyroid (cancer) cells or the functional material containing a high-density lipoprotein (HDL), an asialoglycoprotein or a part thereof for liver (cancer) cells, these cells can be used as the target cells for transduction.

Further, by using antibodies against antigens present on cell surfaces, suitably, monoclonal antibodies as the functional material having cell binding activity, any cells whose antibodies are available can be used as target cells. Thus, a wide variety of cells can be used as the target cells by utilizing the localization method of a retroviral vector and target cells disclosed by the present invention.

In the particularly preferred aspect, the gene transfer efficiency into target cells with a retrovirus is increased by using a novel functional material.

Heretofore, only Heparin-II domain of fibronectin has been known to be the functional material having retrovirus binding domain effective for gene transfer into target cells with retroviruses.

As described above, the domain itself has that binding to certain cells and, in some cases, this activity is undesired depending upon certain target cells. In such cases, the desired results can be obtained by replacing the binding domain with another cell binding domain. In this manner, plural functional materials having different properties can be used and this makes broader application of the gene therapy according to the present invention possible and transduction of the intended target cells can be readily carried out.

The novel functional material having retrovirus binding domain provided by the present invention include fibroblast growth factors, polypeptides containing the factors, collagen fragments, a mixture of the fragments, polypeptides containing the fragments, polymers of the functional material and the like. Polylysines are also used for this purpose of the present invention. These functional materials can be obtained from naturally occurring products or can be artificially produced (e.g., produced by genetic engineering techniques or chemical syntheses). Further, they can be produced by combination of naturally occurring products and chemically synthesized products. The function material can be used for the gene transfer method of the first aspect of the present invention and chimera molecules of the functional material and the other functional material having cell binding domain are also useful for gene transfer.

All the above-described functional materials have retrovirus binding activity. However, these materials do not contain Heparin-II domain of human fibronectin described in WO 95/26200 or polypeptides having similar amino acid sequences.

As the fibroblast growth factor, a substantially purified naturally occurring product can be used or a product prepared by genetic engineering techniques can be used. In the present invention, the fibroblast growth factor, that is represented by SEQ. ID No. 3 of the Sequence Listing can be used and modified derivatives thereof maintaining functions of the polypeptide can also be used. Examples of fibroblast growth factor derivatives include a polypeptide represented by SEQ. ID No. 4 of the Sequence Listing (hereinafter referred to as C-FGF•A). This is a polypeptide wherein the cell adhesion domain polypeptide of fibronectin is coupled to the N-terminal, of a fibroblast growth factor represented by SEQ. ID No. 3 and can be produced by genetic engineering techniques as generally disclosed in U.S. Pat. No. 5,302,701. The polypeptide can be obtained by using *E. coli* which has been disclosed in the above U.S. patent as FERM P-12637, and now deposited under Budapest Treaty with National Institute of Bioscience and Human-Technology (NIBH), Agency of Industrial Science & Technology, Ministry of International Trade & Industry of 1-1-3, Higashi, Tsukuba-shi, Ibaraki-ken, Japan, under the accession number of FERM BP-5278 (date of original deposit; Dec. 9, 1991).

A polypeptide derivative of the above C-FGF•A having CS-1 cell adhesion domain derived from fibronectin which is represented by SEQ. ID No. 5 (hereinafter referred to as C-FGF-CS1) can be obtained by using *Escherichia coli* deposited under Budapest Treaty with the NIBH of 1-1-3, Higashi, Tsukuba-shi, Ibaraki-ken, Japan, under the accession number of FERM BP-5654 (date of original deposit: Sep. 6, 1996) according to the process described herein. This C-FGF-CS1 is particularly useful for gene transfer into target cells having CS-1 binding property, in particular, hematopoietic stem cells.

As collagen fragments, substantially purified fragments obtained by enzymatically or chemically cleaving natural collagens can be used or those prepared by genetic engineering techniques can be used. In addition, modifications of these fragments maintaining their functions can be used. Among collagens, human type V collagen has strong insulin binding activity (JP-A 2-209899). An example of polypeptides having insulin binding domain is a polypeptide which contains an amino acid sequence represented by SEQ. ID No. 28 of the Sequence Listing (JP-A 5-97698), for example, a polypeptide represented by SEQ. ID No. 6 of the Sequence Listing (hereinafter referred to as ColV). ColV can be prepared according to a method disclosed in Examples herein. A polypeptide which contains ColV and represented by SEQ. ID No. 7 (hereinafter referred to as C277-ColV) is the polypeptide wherein the cell adhesion domain polypeptide of fibronectin is coupled to the N-terminal of ColV and can be produced by genetic engineering technique according to JP-A 5-97698 as described, above. C277-ColV can, be obtained by using *E. coli* which is disclosed under the accession number of FERM P-12560 in JP-A 5-97698 and deposited under Budapest Treaty with NIBH of 1-1-3, Higashi, Tsukuba-shi, Ibaraki-ken, Japan, under the accession number of FERM BP-5277 (date of original deposit: Oct. 7, 1991).

A polypeptide (hereinafter referred to as C-ColV-CS1) derived from C277-ColV which is represented by SEQ. ID No. 8 and has CS-1 cell adhesion domain derived from fibronectin can be prepared as follows. A DNA fragment is isolated by amplifying by PCR using the above plasmid pCH102 which is prepared from *E. coli* deposited under Budapest Treaty with NIBH of 1-1-3, Higashi, Tsukuba-shi, Ibaraki-ken, Japan, under the accession number of FERM BP-2800 (date of original deposit: May 12, 1989) as a template and the primers CS1-S (the nucleotide sequence is represented by SEQ. ID No. 9 of the Sequence Listing) and M4, and then digesting with the restriction enzymes NheI and SalI.

On the other hand, a DNA fragment is isolated by amplifying by PCR using the plasmid pTF7520ColV, which contains a gene encoding C277-ColV and prepared from above *E. coli* FERM BP-5277 as a template and the primers CF and CNR, and then digesting with the restriction enzymes AccIII and NheI. The nucleotide sequences of CF and CNR are represented by SEQ. ID Nos. 10 and 12 of the Sequence Listing. The above two DNA fragments are mixed and ligated with an about 4.4 kb DNA fragment obtained by digesting the plasmid pTF7520ColV with the restriction enzymes AccIII and SalI. The resultant plasmid encodes the polypeptide C-ColV-CS1 which has CS-1 cell adhesion domain at the C-terminal of C277-ColV and in which the second glutamic acid from the C-terminal of ColV and the C-terminal threonine are replaced by alanine and serine, respectively. After culture of *E. coli* transformed with this plasmid, the desired polypeptide can be obtained from the culture. This C-ColV-CS1 is particularly useful in gene transfer into a target cell having CS1 binding property, especially, stem cells.

As the polylysine, as described above, that having a suitable polymerization degree can be selected from commercially available polylysines and used.

The functional materials to be used in the present invention can include derivatives of the above functional materials. Examples thereof include the above C-FGF-CS1 or its functional equivalents and C-ColV-CS1 or its functional equivalents. In addition, polymers obtained by polymerizing plural molecules of the functional materials and modified materials obtained by modifying the functional materials according to known methods (addition of sugar chain, etc.) can also be used in the present invention. These polymers and their functional equivalents can be prepared by genetic engineering techniques using genes encoding the polymers and genes encoding their functional equivalents. In addition, a cysteine-added functional material useful for preparing a polymer of the functional material can be prepared by addition, insertion and substitution of cysteine in the amino acid sequence of the functional material. In addition, a molecule which is a cysteine-added functional material and has a retrovirus binding domain is readily coupled to an another molecule which is a cysteine-added functional material and has a target cell binding domain. Furthermore, a material coupled to other functional material can be prepared by utilizing the reactivity of the cysteine residue of the cysteine-added functional material.

In another preferred aspect of the present invention, gene transfer is carried out by using a polymer of the retrovirus binding domain of fibronectin which increases the gene transfer efficiency into target cells with retroviruses.

The functional material is a polypeptide having plural Heparin-II binding domains of human fibronectin in one molecule as described in the above WO 95/26200 or derivatives of the polypeptide. In so far as the same activity as that of the functional material is maintained, functional equivalents a part of whose amino acid sequences are different from that of the naturally occurring products can be included.

Examples of the polymer of the functional material include those obtained by enzymologically or chemically polymerizing the above polypeptide derived from fibronectin or by gene engineering techniques. An example of a polypeptide which has two Heparin-II binding domains derived from fibronectin in a molecule include a polypeptide having an amino acid sequence represented by SEQ. ID No. 13 of the Sequence Listing (hereinafter referred to as H2-547). H2-547 can be obtained according to the method described herein by using *E. coli* which has been deposited under Budapest Treaty with NIBH of 1-1-3, Higashi, Tsukuba-shi, Ibaraki-ken, Japan, under the accession number of FERM BP-5656 (date of original deposit: Sep. 6, 1996). A polypeptide having an amino acid sequence represented by SEQ. ID No. 14 of the Sequence Listing is a polypeptide derivative containing a cell adhesion polypeptide of fibronectin coupled at the N-terminal of H2-547 (hereinafter referred to as CH 2-826). This polypeptide can be obtained according to the method disclosed herein. Further, a polypeptide having an amino acid sequence represented by SEQ. ID No. 30 of the Sequence Listing is a polypeptide derivative containing CS-1 cell adhesion region of fibronectin coupled at the C-terminal of H2-547 (hereinafter referred to as H2S-573). The polypeptide can be obtained according to the method described herein by using *E. coli* which has been deposited under Budapest Treaty with NIBH of 1-1-3, Higashi, Tsukuba-shi, Ibaraki-ken, Japan, under the accession number of FERM BP-5655 (date of original deposit: Sep. 6, 1996). H2S-573 having CS-1 cell adhesion region is useful for gene transfer into hematopoietic stem cells.

In yet another preferred aspect of the present invention, viable target cells are infected with a replication deficient retroviral vector in the presence of the functional material immobilized on beads which is effective to increase the gene transfer efficiency into cells with a retroviral vector.

Conventional methods for improving the gene transfer efficiency into target cells with a retroviral vector by using the functional materials described in the above WO 95/26200 and Nature Medicine are carried out by immobilizing the functional materials on a vessel to be used for infection of cells with viruses (a plate for cell culture). These methods require complicated procedures such as washing of excess functional material after treatment of the plate with a solution containing the functional material.

Then, the gene transfer methods using a plate having the functional materials immobilized thereon are hardly to say a convenient method. On the other hand, a method using the functional materials immobilized on bead(s) has the following advantages.

In comparison with a plate, immobilization on beads can be carried out at a relatively small space and beads can be handled in a sealed vessel. Since a surface of a plate having the functional material immobilized thereon is exposed to air, it is necessary to take care to prevent deterioration or the like due to drying during storage in case the functional material having lower stability. However, beads can be stored by suspending in a solution and such troubles can be avoided. Moreover, a surface area of the functional material becomes larger by using beads and therefore, in comparison with a plate, the higher gene transfer efficiency can be obtained.

Immobilization of the functional materials can be carried out by the conventional method, for example, a target cell culture vessel is coated with the functional materials or the functional materials can be immobilized, for example, on culture beads for culturing cells. The raw material and kind of beads can be selected depending upon the intended use. For example, the bead may have a circular or spherical core as a central portion and the surface of the core can be coated with a hydrophilic polymer. Examples of the raw material and the kind of the core and the polymer are described in JP-A 8-501092. For example, biodegradable beads on which these functional materials are immobilized may be administered in a living body. Alternatively, an effective method is to use a mixture of beads on which a molecule having a retrovirus binding domain is immobilized and beads on which a molecule having a target cell binding domain is immobilized.

When these functional materials are used without immobilization, for example, a target cell culture vessel can be pre-treated with a substance which prevents the functional materials from the adhesion to the vessel, for example, bovine serum albumin (BSA). Thus, the functional materials can be used without non-specific adhesion to the vessel.

According to the present invention, gene transfer can be efficiently carried out even in such a system that the functional material of the present invention is used without immobilization.

In addition, by using the reagent kit specifically designed for carrying out the method of the present invention as described hereinafter, gene transfer into cells can be very conveniently carried out.

As described above, transformant cells obtained according to the method of the present invention can be grafted into a living body, thereby gene therapy can be carried out to express an exogenous gene in a living body.

For example, when hematopoietic stem cells are used as target cells, gene therapy can be carried out by the following procedures. First, a material containing the hematopoietic cells, for example, bone marrow tissue, peripheral blood, fetal umbilical cord blood or the like is collected from a donor. The material can be used as such. However, usually, a monocyte fraction containing hematopoietic stem cells is prepared by density gradient centrifugation or the like. Alternatively, hematopoietic stem cells can be purified by utilizing markers on cell surfaces such as CD34 and/or C-kit. The material containing hematopoietic cells can optionally be pre-stimulated with a suitable cell growth factor or the like and then, the cells are infected with a recombinant retroviral vector into which an intended gene has been inserted according to the method of the present invention, in particular, in the presence of the functional material having stem cell binding activity. The transformant cells thus obtained can be grafted into a recipient by, for example, intravenous administration. The recipient is, preferably, an autologous donor but also including allogeneic transplants, the latter especially where umbilical cord blood cells are used for the graft.

Gene therapy using hematopoietic stem cells as target cells is to compensate for a deficient or abnormal gene of a patient and examples thereof include ADA deficiency and Gaucher's disease. In addition, sometimes, transduction of a drug resistant gene is carried out to relieve hematopoietic stem cell disorders due to chemotherapy used in treatment of cancers, leukemias and the like.

It has been known that hematopoietic stem cells express VLA-4 receptor and it is therefore possible to carry out gene transfer efficiently by using the functional material having CS-1 cell adhesion region disclosed by the present invention. Further, as described above, molecules such as CD34 and C-kit are expressed on the surfaces of hematopoietic stem cells and therefore the gene transfer efficiency can be improved by combining antibodies against to these molecules or a stem cell factor which is a ligand of C-kit with the functional material having retrovirus binding domain.

Moreover, as gene therapy of cancers, tumor vaccinotherapeutics have been studied, wherein cytokine genes are transferred into cancer cells and, after depriving growth capability, the cells are returned to the patient body to increase tumor immunity (Human Gene Therapy, Vol. 5, pp. 153-164 (1994)). Such treatment can, also be carried but effectively by applying the method of the present invention with the functional material having high affinity to cancer cells.

Further, activities have been attempted to treat AIDS by gene therapy. In this case, it has been proposed to transfer a gene encoding a nucleic acid molecule which inhibits HIV replication or gene expression (e.g., anti-sense nucleic acid, ribozyme, etc.) into T cells which is infected with HIV which causes AIDS (J. Virol., Vol. 69, pp. 4045-4052 (1995)). Gene transfer into T cells can be achieved by the method of the present invention with utilizing the functional material, for example, CD4 antibody or the like which can bind to a molecule present on the surface of T cells.

Thus, as target cells for gene transfer, any cells can be used in so far as the functional material having target cell binding domain of the present invention is available or can be prepared.

Moreover, the method of the present invention is suitable for protocols of clinical gene therapy because co-cultivation of target cells in the presence of retrovirus producer cells is not required and the method of the present invention can be carried out in the absence of hekadimethrine bromide whose use is clinically disadvantageous in human being.

Further, as application of the present invention to art fields other than gene therapy, for example, transgenic vertebrate animals can be simply produced by using, as a target cells, embryoplastic stem cells, primordial germ cell, oocyte, oogonia, ova, spermatocyte, sperm and the like.

That is, as one aspect, the present invention provides a method for cellular grafting comprising grafting the transformant cells obtained by the method of the present invention into a vertebrate animal. Examples of vertebrate animals to be grafted with transformant cells include mammals (e.g., mouse, rat, rabbit, goat, pig, horse, dog, monkey, chimpanzee, human being, etc.), birds (e.g., chicken, turkey, quail, duck, wild duck, etc.), reptiles, (e.g, snake, alligator, tortoise, etc.), amphibian (e.g., frog, salamander, newt, etc.), fishes (e.g., dog mackerel, mackerel, bass, snapper, grouper, yellowtail, tuna, salmon, trout, carp, sweetfish, eel, flounder, shark, ray, sturgeon, etc.).

Thus, according to this aspect of the present invention, like substantially pure fibronectin, substantially pure fibronectin fragments or a mixture thereof, gene transfer with retroviruses can be carried out efficiently by the retrovirus binding domain and the target cell binding domain of the functional material to be used in the present invention. Then, the present invention can provide a technique for transferring genetic materials into vertebrate cells without any limitation of conventional techniques.

In a further aspect of the present invention, an effective amount of a material which has both retrovirus binding domain and target cell binding domain on the same molecule and has functions equivalent to those of substantially pure fibronectin, substantially pure fibronectin fragments or a mixture thereof is used as the functional material.

Such a functional material is a material which can perform gene transfer with the same efficiency as that of fibronectin, a fibronectin fragment or a mixture thereof. Typically, it is the functional material having the above novel retrovirus binding domain and target cell binding domain of the present invention on the same molecule. In case of using these materials, it is considered that retroviruses as well as target cells bind to at least one functional material.

Examples of the functional material having a retrovirus binding domain and a target binding domain on the same molecule include polypeptides represented by SEQ. ID Nos. 21 and 22 of the Sequence Listing (hereinafter referred to as CHV-181 and CHV-179, respectively).

These peptides include type III similar sequences (III-12, III-13 and III-14) contained in H-271. In CHV-181, III-12 and III-13 sequences, and in CHV-179, III-13 and III-14 sequences are added to the C-terminal of the cell adhesion polypeptide ($Pro^{1239}$-$Ser^{1515}$) of fibronectin via methionine. A plasmid for expressing the polypeptide CHV-181 can be constructed, for example, by the following procedures.

First, the plasmid pHD101 containing a DNA fragment encoding the heparin binding polypeptide (H-271) of fibronectin is prepared in *Escherichia coli* HB101/pHD101 (FERM BP-2264). A HindIII site is introduced in a region encoding the C-terminal of the III-13 sequence on this plasmid by site-directed mutagenesis, followed by digestion with NcoI and HindIII to obtain a DNA fragment encoding III-12 and III-13 sequence. On the other hand, the plasmid vector pINIII-ompA$_1$ is digested with HindIII and SalI to obtain a DNA fragment encoding a lipoprotein terminator region.

Next, the plasmid pTF7021 containing a DNA fragment encoding the cell adhesion polypeptide (C-279) of fibronectin is prepared from *Escherichia coli* JM109/pTF7021 (FERM BP-1941), and a NcoI site is introduced immediately before termination codon of C-279 on the plasmid by site-directed mutagenesis to obtain the plasmid pTF7520. This plasmid is digested with NcoI and SalI, followed by mixing with the DNA fragment encoding the III-12 and III-13 sequence and the DNA fragment encoding a lipoprotein terminator region to ligate them to obtain the plasmid pCHV181 for expressing the polypeptide CHV-181. The nucleotide sequence of a region encoding the polypeptide CHV-181 on the plasmid pCHV181 is shown in SEQ. ID No. 27 of the Sequence Listing.

A plasmid for expressing the polypeptide CHV-179 can be constructed, for example, by the following procedures.

First, a NcoI site is introduced in a region encoding the N-terminal of the III-13 sequence on the plasmid pHD101 by site-directed mutagenesis, followed by digestion with NcoI and HindIII to obtain a DNA fragment encoding the III-13 and III-14 sequence. This is mixed with a DNA fragment encoding the above lipoprotein terminator region and the NcoI and SalI-digested plasmid pTF7520 to ligate them to obtain the plasmid pCHV179 for expressing the polypeptide CHV-179.

CHV-181 and CHV-179 can be obtained by culturing *E. coli* transformed with the above plasmids, respectively, then purifying from the resulting culture.

These functional materials can be used by immobilized on, for example, beads as described above or without immobilization.

In another aspect, the present invention provides a culture medium of target cells to be used for gene transfer into the target cells with retroviruses which comprises (1) the above-described mixture of an effective amount of the functional material having retrovirus binding domain and an effective amount of another functional material having the target cell binding domain or (2) an effective amount of the functional material having the above described novel retrovirus binding domain and target cell binding domain on the same molecule. The functional material may be immobilized or may be used without immobilization.

Other ingredients of the culture medium of the present invention are not specifically limited in so far as they can be used in culture of target cells and commercially available culture mediums for culturing cells can be used. The culture medium of the present invention can also contain serum, a cell growth factor necessary for growth of target cells, an antibiotic for preventing contamination of microorganisms and the like. For example, in case of NIH/3T3 cell, Dulbecco's modified Eagle's medium (DMEM, JRH Bioscience) containing 10% bovine fetal serum (Gibco), 50 units/ml, of penicillin and 50 µg/ml of streptomycin (both Gibco) can be used as the culture medium.

In further aspect, the present invention provides a method for localization of a retrovirus which comprises incubating a culture medium containing the retrovirus contacted with (1) the above-described mixture of a molecule containing the retrovirus binding domain and another molecule containing the target cell binding domain, (2) the above-described functional material having the novel retrovirus binding domain of the present invention and a target cell binding domain on the same molecule, or (3) the above-described functional material having the retrovirus binding domain.

As described above, the functional material may be immobilized or may be used without immobilization. Incubation can be carried out according to a conventional method, for example, at 37° C. under the conditions of $CO_2$ concentration of 5% and humidity of 99.5%. These conditions can be suitably adjusted depending on particular target cells to be used and the culture period can also be changed according to particular cells and purposes.

By using the method of the present invention, viral particles can be localized in various constructs which deliver viruses into target cells.

In another aspect of the present invention, there is provided a kit for using retrovirus-mediated gene transfer into target cells. The kit comprises:

(a) an effective amount of (1) a mixture of the molecule having the above described retrovirus binding domain and another molecule having the target cell binding domain, or (2) the functional material having the novel retrovirus binding domain of the present invention and the target cell binding domain on the same molecule;

(b) an artificial substrate for incubating the retrovirus contacted with the target cells; and (c) a target cell growth factor for pre-stimulating the target cells. The functional material (a) may be immobilized or non-immobilized. This kit may further comprise a recombinant retroviral vector, necessary buffers and the like.

As the artificial substrate, there can be used plates for culturing cells, petri dishes, flasks and the like. They may be made of polystyrene.

In case that target cells are cells in $G_o$ phase, infection with a retrovirus does not occur and therefore, preferably, cells are pre-stimulated to lead cells to the cell cycle. For this purpose, target cells are cultured in the presence of a suitable cell growth factor prior to infection with a retrovirus. For example, in case of gene transfer into bone marrow cells and hematopoietic stem cells, a target cell growth factor such as Interleukin-6 or a stem cell factor can be used.

Respective constituent members of the kit can be prepared in the form of freeze dried products, granules, tablets in addition to aqueous solutions according to per se known methods.

By using the kit of the present invention, for example, a transformed viable target cell culture can be obtained and retrovirus-mediated transduction into target cells can be simply carried out.

The present invention also includes a method for gene transfer into target cells with retrovirus wherein the functional material selected from the group consisting of substantially pure fibronectin, substantially pure fibronectin fragments and a mixture thereof, or a polymer thereof which is immobilized on beads or not immobilized is used.

The present invention includes the above described CH2-826 and its functional equivalents. In addition, the present invention provides a gene encoding CH2-826. One example thereof is a gene represented by SEQ. ID No. 20 of the Sequence Listing. The present invention also includes functional equivalents of the gene.

Further, the present invention provides the above described CHV-181 and includes its functional equivalents. In addition, the present invention provides a gene encoding CHV-181. One example of the gene is that represented by SEQ. ID No. 27 of the Sequence Listing. The present invention also includes functional equivalents of the gene.

The present invention also provides a polymer containing a polymer of the retrovirus binding domain and/or a polymer of the target cell binding domain. Specific examples of the polymer are a polymer of a fibroblast growth factor and a polymer of a polypeptide having an insulin binding domain derived from type V collagen.

As discussed hereinafter, although the present invention is not limited by any theory, it is believed that gene transfer into cells with a retrovirus, i.e., transformation is enhanced by binding the retrovirus and the target cell to respective functional domains.

As such a functional material which binds to a retrovirus and thus is useful in the present invention, there are substantially pure fibronectin, substantially pure fibronectin fragments or a mixture thereof. The present inventors have found that the above-described functional materials of the present invention having functions substantially the same as those of substantially pure fironectin and the like improve the gene transfer efficiency, i.e., the transformation efficiency of target cells with a retrovirus.

The fragments of fibronectin described herein may be of natural or synthetic origin and can be prepared in substantial purity from naturally occurring materials, for example as previously described by Ruoslahti et al. (1981) J. Biol. Chem. 256:7277; Patel and Lodish (1986) J. Cell. Biol. 102:449; and Bernardi et al. (1987) J. Cell. Biol. 105:489. In this regard, reference herein to substantially pure fibronectin or a fibronectin fragment is intended to mean that they are essentially free from other proteins with which fibronectin naturally occurs.

The substantially pure fibronectin or fibronectin fragment described herein can also be produced by genetic engineering techniques, for example, as generally described in U.S. Pat. No. 5,198,423. In particular, the recombinant fragments identified in the Examples below as H-271, H-296, CH-271 (SEQ ID NO 23) and CH-296 (SEQ ID NO 24), and methods for obtaining them, are described in detail in this patent. The C-274 fragment used in the Examples below was obtained as described in U.S. Pat. No. 5,102,988. These fragments or fragments from which they can be routinely derived are available by culturing E. coli deposited with NIBH of 1-1-3, Higashi, Tsukuba-sh, Ibaraki-ken, Japan under Budapest Treat with the accession numbers of FERM P-10721 (H-296) (the date of original deposit: May 12, 1989), FERM BP-2799 (C-277 bound to H-271 via methionine) (the date of original deposit: May 12, 1989), FERM BP-2800 (C-277 bound to H-296 via methionine) (the date of original deposit: May 12, 1989) and FERM BP-2264 (H-271) (the date of original deposit: Jan. 30, 1989), as also described in U.S. Pat. No. 5,198,423.

In addition, useful information as to fibronectin fragments utilizable herein or as to starting materials for such fragments may be found in Kimizuka et al., J. Biochem. 110, 284-291 (1991), which reports further as to the above-described recombinant fragments; in EMBO J., 4, 1755-1759 (1985), which reports the structure of the human fibronectin gene; and in Biochemistry, 25, 4936-4941 (1986), which reports on the Heparin-II binding domain of human fibronectin. Fibronectin fragments which contain both the CS-1 cell adhesion domain and the Heparin-II binding domain have been found to significantly enhance the efficiency of gene transfer into hematopoietic cells in work thus far.

It will thus be understood that the fibronectin-related polypeptides described herein will provide an amino acid sequence having the cell-binding activity of the CS-1 cell adhesion domain of fibronectin as well as an amino acid sequence of the Heparin-II binding domain of fibronectin which binds the virus.

The viral-binding polypeptide utilized to enhance transduction by retroviral vectors as disclosed in WO 95/26200 will comprise (i) a first amino acid sequence which corresponds to the $Ala^{1690}$-$Thr^{1960}$ of the Heparin-II binding domain of human fibronectin, which is represented by the formula (SEQ ID NO 1):

Ala Ile Pro Ala Pro Thr Asp Leu Lys Phe Thr Gln

Val Thr Pro Thr Ser Leu Ser Ala Gln Trp Thr Pro

Pro Asn Val Gln Leu Thr Gly Tyr Arg Val Arg Val

Thr Pro Lys Glu Lys Thr Gly Pro Met Lys Glu Ile

-continued

```
Asn Leu Ala Pro Asp Ser Ser Ser Val Val Val Ser

Gly Leu Met Val Ala Thr Lys Tyr Glu Val Ser Val

Tyr Ala Leu Lys Asp Thr Leu Thr Ser Arg Pro Ala

Gln Gly Val Val Thr Thr Leu Glu Asn Val Ser Pro

Pro Arg Arg Ala Arg Val Thr Asp Ala Thr Glu Thr

Thr Ile Thr Ile Ser Trp Arg Thr Lys Thr Glu Thr

Ile Thr Gly Phe Gln Val Asp Ala Val Pro Ala Asn

Gly Gln Thr Pro Ile Gln Arg Thr Ile Sys Pro Asp

Val Arg Ser Tyr Thr Ile Thr Gly Leu Gln Pro Gly

Thr Asp Tyr Lys Ile Tyr Leu Tyr Thr Leu Asn Asp

Asn Ala Arg Ser Ser Pro Val Val Ile Asp Ala Ser

Thr Ala Ile Asp Ala Pro Ser Asn Leu Arg Phe Leu

Ala Thr Thr Pro Asn Ser Leu Leu Val Ser Trp Gln

Pro Pro Arg Ala Arg Ile Thr Gly Tyr Ile Ile Lys

Tyr Glu Sys Pro Gly Sev Pro Pro Arg Glu Val Val

Pro Arg Pro Arg Pro Gly Val Thr Glu Ala Thr Ile

Thr Gly Leu Glu Pro Gly Thr Glu Tyr Thr Ile Tyr

Val Ile Ala Leu Lys Asn Asn Gln Lys Ser Glu Pro

Leu Ile Gly Arg Lys Lys Thr;
``` or a sufficiently similar amino acid sequence thereto to exhibit the ability to bind the retrovirus;

and (ii) a second amino acid sequence (CS-1) which corresponds to one portion of the IIICS binding domain of human fibronectin; which is represented by the formula (SEQ. ID No. 2):

Asp Glu Leu Pro Gln Leu Val Thr Leu Pro His Pro Asn Leu His Gly Pro Glu Ile Leu Asp Val Pro Ser Thr;

or a sufficiently similar amino acid sequence thereto to exhibit the ability to bind hematopoietic cells such as primitive progenitor and/or long term repopulating (stem) cells.

The retrovirus binding activity of a polypeptide represented by the above SEQ. ID No. 1 (H-271) shows a concentration dependence and, as indicated in Example 8 below, it shows substantially the same activity as that of CH-271 at high concentrations. That is, a retrovirus and target cells bind to at least one molecule of H-271 for the first time in the presence of a high concentration of H-271.

The strong virus binding to the virus binding domain of the functional material of the present invention can be used for constructing delivery systems for virus-mediated therapy across a broad range of cell types. For this purpose, a polypeptide containing the retrovirus binding domain of the functional material of the present invention can be coupled to any material containing a cell binding domain which gives this construct specificity for the target cells, or can be co-localized with a material containing its cell binding domain. That is, the virus binding polypeptide may be covalently coupled to the cell binding material or they may be different molecules.

This approach will circumvent the prior necessity of constructing specific retrovirus cell lines for each target cell and facilitate selection of the functional material having the most suitable target cell binding domain according to a particular kind of target cells. Therefore, by using the functional material of the present invention, transduction specific for target cells to be used can be readily carried out and, in particular, the method of the present invention wherein a mixture of the functional material having retrovirus binding domain and the functional material having target cell binding domain is especially useful for transfer the required gene into the intended target cell. In addition, the novel functional material provided by the present invention is especially useful for the method for improving the gene transfer efficiency into target cells with retroviruses and related techniques.

The following Examples further illustrate the present invention in detail but are not to be construed to limit the scope thereof.

Example 1

(1) Preparation of Virus Supernatant

GP+E-86 producer cells (ATCC CRL-9642) containing retroviral plasmid PM5neo vector containing a neomycin resistant gene (Exp. Hematol., 23, 630-638 (1995)) were cultured in Dulbecco's modified Eagle medium (DMEM, JRH Bioscience) containing 10% fetal calf serum (FCS, Gibco) and 50 units/ml of penicillin and 50 μg/ml of streptomycin (both Gibco). All DMEM used hereinafter contained 50 units/ml of penicillin and 50 μg/ml of streptomycin. PM5neo virus containing supernatant was collected by adding 4 ml of DMEM containing 10% FCS to semi-confluent plates to culture overnight. Harvested medium was filtered through 0.45 micron filters (Millipore) to obtain virus supernatant which was stored at −80° C. until used.

Separately, regarding retrovirus plasmid, TKNEO vector (Blood, 78, 310-317 (1991)), TKNeo virus supernatant was prepared according to the same procedures as those described above by using GP+envAm-12 cells (ATCC CRL-9641).

(2) Determination of Virus Titer of Supernatant

The virus titer of the supernatant was determined by using NIH/3T3 cells according to the standard method (J. Virol., 62, pp. 1120-1124 (1988)). Namely, DMEM and 2,000 cells/well of NIH/3T3 cells were added to a 6-well tissue culture plate. After cultivation overnight, the serially diluted virus supernatant was added to each well together with hexadimethrine bromide (polybrene manufactured by Aldrich) at the final concentration of 7.5 μg/ml. This was incubated at 37° C. for 24 hours and then the medium was replaced by that containing G418 (Gibco) at the final concentration of 0.75 mg/ml. The plate was further incubated. G418 resistant ($G418^r$) colonies which grew after 10 to 12 days were stained with crystal violet to record their count. The number of infectious particles per 1 ml of the supernatant (cfu/ml) was calculated by multiplying the number of colonies per well by the dilution rate and it was used as the titer of the supernatant to determine the amount of the virus supernatant to be added in the subsequent experiments.

Example 2

(1) Preparation of Polypeptide Derived from Fibronectin

The polypeptide derived from human fibronectin, H-271 (amino acid sequence is shown in SEQ. ID No. 1 of the Sequence Listing) was prepared from *E. coli* containing the recombinant plasmid containing DNA encoding the polypeptide, pHD101, i.e., *Escherichia coli* HB101/pHD101 (FERM BP-2264) according to the method disclosed in U.S. Pat. No. 5,198,423.

The polypeptide, CH-271 (amino acid sequence is shown in SEQ. ID No. 23 of the Sequence Listing) was prepared as follows. Namely, *Escherichia coli* HB101/pCH101 (FERM BP-2799) was cultured according to the method described in the above patent and CH-271 was obtained from the culture.

And, the polypeptide, CH-296 (amino acid sequence is shown SEQ. ID No. 24) was prepared as follows. Namely, *Escherichia coli* HB101/pCH102 (FERM BP-2800) was cultured according to the method described in the above patent and CH-296 was obtained from the culture.

The polypeptide, C-274 (amino acid sequence is shown in SEQ. ID No. 25 of the Sequence Listing) was prepared as follows. Namely, *Escherichia coli* JM109/pTF7221 (FERM BP-1915) was cultured according to the method described in U.S. Pat. No. 5,102,988 and C-274 was obtained from the culture.

Further, the polypeptide, C277-CS1 (amino acid sequence is shown in SEQ. ID No. 29 of the Sequence Listing) was prepared as follows. Namely, *Escherichia coli* HB101/pCS25 which was disclosed in JP-A 3-284700 under FERM P-11339 and was deposited with the above NIBH of 1-1-3, Higashi, Tsukuba-shi, Ibaraki-ken under Budapest Treaty with the accession number FERM BP-5723 (date of original deposit: Mar. 5, 1990) was cultured according to the method described in the above patent and C277-CS1 was obtained from the culture.

(2) Preparation of C-FGF•A

The polypeptide, C-FGF•A (amino acid sequence is shown in SEQ. ID No. 4 of the Sequence Listing) was prepared as follows. Namely, *E. coli* containing the recombinant plasmid containing DNA encoding the above polypeptide, pYMH-CF•A, i.e., *Escherichia coli* JM109/pYMH-CF•A (FERM BP-5278) was cultured in 5 ml of LB broth containing 100 μg/ml of ampicillin at 37° C. for 8 hours. This pre-culture broth was inoculated into 500 ml of LB broth containing 100 μg/ml of ampicillin and 1 mm of IPTG (isopropyl-β-D-thiogalactopyranoside) and cultivated at 37° C. overnight. The microbial cells were harvested, suspended in 10 ml of PBS (phosphate buffered saline) containing 1 mM PMSF (phenylmethanesulfonium fluoride) and 0.05% of Nonidet P-40 and sonicated to disrupt the cells. The mixture was centrifuged to obtain a supernatant. To absorbance 4,000 at 260 nm of this supernatant was added 1 ml of 5% polyethylene imine and the mixture was centrifuged to obtain a supernatant. The supernatant was applied to a HiTrap-Heparin column (Pharmacia) equilibrated with PBS. After washing the non-absorbed fraction with PBS, the absorbed fraction was eluted with PBS containing NaCl gradient of from 0.5 M to 2 M. The eluate was analyzed by SDS-polyacrylamide gel electrophoresis (SDS-PAGE) which showed the presence of two fractions containing 47 kd polypeptide. One fraction of them which was eluted at the higher NaCl concentration was collected and applied to a Superose 6 column (Pharmacia) equilibrated with PBS containing 1.5 M NaCl. The eluate was analyzed by SDS-PAGE and a fraction containing about 47 kd polypeptide was collected to obtain the purified C-FGF•A which was used in the subsequent steps.

(3) Preparation of C-FGF-CS1

First, a plasmid was constructed for expressing the polypeptide, C-FCF-CS1 (amino acid sequence is shown in SEQ. ID No. 5 of the Sequence Listing) in *Escherichia coli* as a host.

*Escherichia coli* HB101/pCH102 (FERM BP-2800) was cultured and the plasmid pCH102 was prepared by alkali-SDS method from the resulting microbial cells. PCR was carried out using this plasmid as a template as well as primer M4 (Takara Shuzo Co., Ltd.) and primer CS1-S, nucleotide sequence of which is shown in SEQ. ID No. 9 in the Sequence Listing and an amplified DNA fragment in the reaction solution was recovered with ethanol precipitation. The resultant DNA fragment was digested with NheI and SalI (both Takara Shuzo. Co., Ltd.), followed by agarose gel electrophoresis to recover about 970 bp DNA fragment from the gel.

*Escherichia coli* JM109/pYMH-CF•A (FERM BP-5278) was then cultured and the plasmid pYMH-CF•A was prepared by an alkali-SDS method from the resulting microbial cells. PCR reaction was carried out using this plasmid as a template as well as primer CF, nucleotide sequence of Which is shown in SEQ. ID No. 10, and primer FNR, nucleotide sequence of which is shown in SEQ. ID No. 11 of the Sequence Listing, and an amplified DNA fragment in the reaction solution was recovered with ethanol precipitation. The resultant DNA fragment was digested with Eco52I (Takara Shuzo Co., Ltd.) and NheI, followed by agarose gel electrophoresis to recover about 320 bp DNA fragment from the gel.

About 4.1 kb DNA fragment isolated by digesting the plasmid pYMH-CF•A with Eco52I and SalI and subjecting to agarose gel electrophoresis was mixed with the above 970 bp DNA fragment and about 320 bp DNA fragment to ligate them to obtain a recombinant plasmid which was inserted into *E. coli* JM109. A plasmid was prepared from the resulting transformant and that containing each one molecule of the above three DNA fragments was selected and named plasmid pCFS100. *E. coli* JM109 transformed with the plasmid pCFS100 was named *Escherichia coli* JM109/pCRS100. The plasmid pCFS100 has a CS-1 cell adhesion region derived from fibronectin at the C-terminal of C-FGF•A and encodes the polypeptide, C-FGF-CS1, wherein second lysine from the C-terminal of FGF was substituted with alanine.

The polypeptide, C-FGF-CS1 was prepared as follows. Namely, the above *E. coli* JM109/pCFS100 was cultured in 5 ml of LB broth containing 100 μg/ml of ampicillin at 37° C. for 8 hours. This pre-cultured broth was inoculated into 500 ml of LB broth containing 100 μg/ml of ampicillin and 1 mM IPTG and cultured overnight at 37° C. to collect the microbial cells. The resulting microbial cells were suspended in 10 ml of PBS (phosphate buffered saline) containing 0.5M NaCl, 1 mM PMSF and 0.05% Nonidet P-40, and the microbial cells were sonicated to disrupt and centrifuged to obtain a supernatant. This supernatant was subjected to HiTrap-Heparin column pre-equilibrated with PBS containing 0.5 M NaCl, the non-adsorbed is fractions were washed with PBS containing 0.5 mM NaCl and the adsorbed fraction was eluted with PBS having a concentration gradient of 0.5 M to 2 M NaCl. The eluate was analyzed by SDS-polyacrylamide gel electrophoresis and fractions containing about 50 kd polypeptide were collected to obtain purified C-FGF-CS1 which was used in the subsequent steps.

Amino acid sequence of from N-terminal to the fifth amino acid of purified C-FGF-CS1 thus obtained was investigated and found to be consistent with that shown in SEQ. ID No. 5 of the Sequence Listing. In addition, molecular weight of purified C-FGF-CS1 measured by mass spectroscopy was consistent with that expected from the above amino acid sequence.

(4) Preparation of C277-ColV

The polypeptide, C277-ColV (amino acid sequence is shown in SEQ. ID No. 6 of the Sequence Listing) was purified as follows. Namely, *E. coli* containing the recombinant plasmid containing DNA encoding the above polypeptide, pTF7520ColV, i.e., *Escherichia coli* JM109/pTF7520 ColV (FERM BP-5277) was cultured in 5 ml of LB broth containing 100 µg/ml of ampicillin at 37° C. for 6.5 hours. This pre-culture broth was inoculated into 500 ml of LB broth containing 100 µg/ml ampicillin and cultivated at 37° C. When the absorbance at 660 nm reached 0.6, IPTG was added to the broth to make up to 1 mM of the final concentration and the broth was cultured overnight to harvest microbial cells. The microbial cells obtained were suspended in 10 ml of PBS containing 1 mM of EDTA, 0.05% of Nonidet P-40 and 2 mM of PMSF, and sonicated for 10 minutes to disrupt the cells. The cell disruption solution was centrifuged and the resultant supernatant was applied to a Resource Q column (Pharmacia) to obtain a non-adsorbed fraction containing the desired polypeptide. The fraction was applied to HiTrap-Heparin column equilibrated with PBS. After washing the non-adsorbed fraction with PBS, the adsorbed fraction was eluted with PBS having NaCl gradient of from 0 M to 0.5 M NaCl. The eluate was analyzed by SDS-PAGE and the fractions containing 48 kd polypeptide were collected to obtain the purified C277-ColV which was used in the subsequent steps.

(5) Preparation of ColV

First, a plasmid was constructed for expressing the polypeptide, ColV (amino acid sequence is shown in SEQ. ID No. 6 of the Sequence Listing) in *Escherichia coli* as a host.

*Escherichia coli* HB101/pTF7520ColV (FERM BP-5277) was cultivated and the plasmid pTF7520ColV was prepared by alkali-SDS method from the resulting microbial cells. This plasmid was digested with NcoI and BamHI (both Takara Shuzo Co., Ltd.), followed by agarose gel electrophoresis to recover about 0.58 kb DNA fragment from the gel. This was mixed with the plasmid vector pET8C (Novagen) predigested with NcoI and BamHI to ligate them. The resultant recombinant plasmid was introduced into *E. coli* BL21 to obtain a transformant, from which plasmids were prepared, a plasmid containing only one molecule of the above about 0.58 kb DNA fragment was selected and named pETColV.

*E. coli* BL21 transformed with the above plasmid pET-ColV, that is, *Escherichia coli* BL-21/pETColV was cultured overnight in 10 ml of LB broth containing 50 µg/ml of ampicillin at 37° C. 0.2 ml of this pre-culture, solution was inoculated into 100 ml of L-broth containing 50 µg/ml of ampicillin, followed by cultivating at 37° C. When the absorbance at 600 nm reached 0.4, IPTG was added thereto at the final concentration of 1 mM, followed by cultivating overnight to collect the microbial cells. The resulting microbial cells were suspended in 5 ml of PBS (phosphate buffered saline) containing 1 mM of EDTA, 0.05% of Nonidet P-40, 10 µg/ml of aprotinin, 10 µg/ml of leupeptin and 2 mM of PMSF, the cells were sonicated to disrupt, followed by centrifugation to obtain a supernatant. This supernatant was subjected to a HiTrap-Heparin column equilibrated with PBS, the non-adsorbed fractions were washed with PBS and the adsorbed fraction was eluted with PBS containing 0.5M NaCl. The eluate was analyzed by SDS-polyacrylamide gel electrophoresis and almost homogenous about 18 kd polypeptide was confirmed. Purified ColV thus obtained was used in the subsequent steps.

(6) Preparation of H2-547

A plasmid for expressing the polypeptide, H2-547 (amino acid sequence is shown in SEQ. ID No. 13 of the Sequence Listing) was constructed as follows. *Escherichia coli* HB101/pCH101 (FERM BP-2800) was cultivated and the plasmid pCH102 was prepared from the resultant cells using alkali-SDS method. PCR was carried out using this plasmid as a template as well as primer 12S, the nucleotide sequence of which is shown in SEQ. ID No. 15 of the Sequence Listing, and primer 14A, the nucleotide sequence of which is shown in SEQ. ID No. 16 of the Sequence Listing, followed by agarose gel electrophoresis to recover an about 0.8 kb DNA fragment encoding a heparin binding polypeptide of fibronectin from the gel. The resulting DNA fragment was digested with NcoI and BamHI (both Takara Shuzo Co., Ltd.) and mixed with NcoI-BamHI digested pTV118N (Takara Shuzo Co., Ltd.) to ligate them, which was inserted into *E. coli* JM109. Plasmids were prepared from the resulting transformant and a plasmid containing the above DNA fragment was selected and manned plasmid pRH1.

The plasmid vector, pINIII-ompA$_1$ (The EMBO Journal, 3, 3437-2442 (1984)) was digested with BamHI and HincII (Takara Shuzo Co., Ltd.) to recover an about 0.9 kb DNA fragment containing a lipoprotein terminator region. This was mixed with BamHI-HincII digested plasmid pRH1 to ligate them to obtain the plasmid pRH1-T containing lac promoter, DNA fragment encoding a heparin binding polypeptide and lipoprotein terminator in this order.

An about 3.1 kb DNA fragment obtained by digesting the plasmid pRH1-T with NheI and ScaI (both Takara Shuzo Co., Ltd.) and an about 2.5 kb DNA fragment obtained by digesting the plasmid pRH1-T with Spe I (Takara Shuzo Co., Ltd. and ScaI were prepared, respectively, and these two fragments were ligated to obtain the plasmid pRH2-T containing lac promoter, open reading frame encoding a polypeptide wherein two heparin binding polypeptides are connected in tandem, and lipoprotein terminator in this order. A nucleotide sequence of the above open reading frame is shown SEQ. ID No. 17 of the Sequence Listing.

The polypeptide, H2-547 was prepared as follows. Four 500 ml Erlenmeyer flasks, equipped with a baffle, containing 120 ml of LB broth containing 100 µg/ml of ampicillin were prepared, these were inoculated with *E. coli* HB101 transformed with the above plasmid pRH2-T, that is, *Escherichia coli* HB101/pRH2-T to culture overnight at 37° C. The microbial cells were collected from the culture by centrifugation, suspended in a 40 ml disruption buffer (50 mM tris-HCl, 1 mM EDTA, 150 mM NaCl, 1 mM DTT, 1 mM PMSF, pH 7.5) and the microbial cells were sonicated to disrupt. The supernatant obtained by centrifugation was subjected to High trap Heparin column (Pharmacia) equilibrated with a purification buffer (50 mM tris-HCl, pH 7.5). The non-adsorbed fractions in the column were washed with the same buffer, followed by elution with a purification buffer having the concentration gradient of 0 to 1 M NaCl. The eluate was analyzed with SDS-polyacrylamide gel electrophoresis and the fractions containing a polypeptide having the molecular weight of about 60,000 were collected to obtain purified H2-547 preparation. The protein amount contained in the resulting preparation was analyzed with BCA PROTEIN ASSAY REAGENT (Pierce) using bovine serum albumin as a standard, indicating that about 10 mg of H2-547 was obtained.

Amino acid sequence of from the N-terminal to the fifth residue of purified H2-547 thus obtained was investigated and found to be consistent with amino acid sequence of H2-547 expected from nucleotide sequence shown in SEQ ID NO 17 of the Sequence Listing minus methionine at the N-terminal (sequence thereof is shown in SEQ. ID No. 13 of the Sequence Listing). The molecular weight of purified H2-547 measured by mass spectroscopy was consistent with that expected from amino acid sequence shown in SEQ. ID No. 13 of the Sequence Listing.

(7) Preparation of CH2-826

A plasmid for expressing the polypeptide, CH2-826 (amino acid sequence is shown in SEQ. ID No. 14 of the Sequence Listing) was constructed as follows. PCR was carried out using the above plasmid pCH102 as a template as well as primer CLS, the nucleotide sequence of which is shown in SEQ. ID No. 18 of the Sequence Listing, and primer CLA, the nucleotide sequence of which is shown in SEQ. ID No. 19 of the Sequence Listing, followed by agarose gel electrophoresis to recover an about 0.8 kb DNA fragment encoding the cell adhesion polypeptide of fibronectin. The resulting DNA fragment was digested with NcoI and BglII (both Takara Shuzo Co., Ltd.) and mixed with NcoI-BamHI digested pTV118N to ligate them, which was inserted into E. coli JM109. Plasmids were prepared from the resulting transformant and a plasmid containing the above DNA fragment was selected and named plasmid pRC1. An about 2.5 kb DNA fragment obtained by digesting this plasmid pRC1 with SpeI and ScaI and an about 3.9 kb DNA fragment obtained by digesting the above plasmid pRH2-T with NheI and ScaI were mixed to ligate them to obtain the plasmid pRCH2-T encoding a polypeptide wherein two heparin binding polypeptides are tandemly connected to the C-terminal of the cell adhesion polypeptide. A nucleotide sequence of open reading frame on the plasmid pRCH2-T encoding this polypeptide is shown in SEQ. ID No. 20 of the Sequence Listing.

The polypeptide, CH2-826 was prepared according to the same method as that used for the polypeptide H2-547 described in Example 2 (6). The fractions containing a polypeptide having the molecular weight of about 90,000 were collected from the eluate of High trap Heparin column to obtain purified CH2-826.

(8) Preparation of H2S-537

A plasmid for expressing the polypeptide, H-2S-537 (amino acid sequence is shown in SEQ. ID No. 30 of the Sequence Listing) was constructed as follows. PCR was carried out using the above plasmid pCH102 as a template as well as primer CS1S, the nucleotide sequence of which is shown in SEQ. ID No. 31 of the Sequence Listing, and primer CS1A, the nucleotide sequence of which is shown in SEQ. ID No. 32 of the Sequence Listing, followed by agarose gel electrophoresis to recover an about 0.1 kb DNA fragment encoding the cell adhesion polypeptide of fibronectin. The resulting DNA fragment was digested with NcoI and BamHI (both Takara Shuzo Co., Ltd.) and mixed with NcoI-BamHI digested pTV118N to ligate them, which was inserted into E. coli JM109. Plasmids were prepared from the resulting transformant and a plasmid containing the above DNA fragment was selected and named plasmid pRS1.

The plasmid vector, pINIII-ompA$_1$ was digested with BamHI and HincII to recover an about 0.9 kb DNA fragment containing a lipoprotein terminator region. This was mixed with BamHI-HincII digested plasmid pRS1 to ligate them to obtain the plasmid pRS1-T containing lac promoter, DNA fragment encoding CS-1 region polypeptide and lipoprotein terminator in this order.

An about 2.4 kb DNA fragment obtained by digesting this plasmid pRS1-T with NheI and ScaI and an about 3.3 kb DNA fragment obtained by digesting the above plasmid pRH2-T with SpeI, ScaI and PstI (Takara Shuzo Co., Ltd.) were prepared. They were ligated to obtain the plasmid pRH2S-T containing lac promoter, open reading frame encoding a polypeptide having such structure in which two heparin binding polypeptides are tandemly connected and CS-1 region is further coupled to the C-terminal thereof, and lipoprotein terminator in this order. A nucleotide sequence of the above open reading frame is shown in SEQ. ID No. 32 of the Sequence Listing.

The polypeptide, H2S-573 was prepared according to the same method as that used for the polypeptide H2-547 described in Example 2 (6). The fractions containing a polypeptide having the molecular weight of about 60,000 were collected from the eluate of High trap Heparin column to obtain purified H2S-573.

(9) Immobilization of Functional Material on Plate

For using a plate on which the functional material was immobilized in the experiment for infection of cells with a retrovirus (6-well tissue culture plate, Falcon), immobilization was carried out according to the following procedures. Namely, a solution of each functional material described the above Examples dissolved in PBS at a suitable concentration was added to a plate at an amount of 2 ml per well (bottom area 9.6 cm$^2$) and the plate was incubated under UV light at room temperature for one hour without its cover and then for additional one hour with its cover. Then, the polypeptide solution was exchanged to 2 ml of PBS containing 2% bovine serum albumin (BSA, Boehringer Mannheim) and incubated at room temperature for 30 minutes. The plate was washed with PBS containing 25 mM of HEPES. A control plate coated on which BSA was immobilized was prepared according to the same manner as indicated above except that the incubation with the polypeptide solution was not carried out.

In gene transfer (virus infection) experiment in Examples below, the above 6-well tissue culture plate was used unless otherwise indicated. When the concentration of the functional material used for immobilization on the plate is indicated, an polypeptide amount per unit bottom area of a well is described using as unit of pmol/cm$^2$ (and μg/cm$^2$). For example, when immobilization is carried out by using 2 ml of 48 μg/ml of H-271 solution on the above plate (bottom area 9.6 cm$^2$), the description is "immobilization was carried out with 333 pmol/cm$^2$ (10 μg/cm$^2$) of H-271". And, CH-296 immobilized plate to be used for culturing non-adherent cells (TF-1, HL-60) after transduction was that prepared by immobilization of 48 pmol/cm$^2$ (3 μg/cm$^2$) of a CH-296 solution according to the above procedures. In the subsequent Examples, virus infection of target cells was always carried out in a medium without polybrene. When an amount of virus, cell, medium and the like are indicated, the amount per well is described unless otherwise indicated.

Example 3

(1) Gene Transfer Using Mixture of Functional Materials

The following experiment was carried out to investigate the effect on the gene transfer in case of immobilization of a mixture of a cell binding material and a retrovirus binding material on a plate. First, each polypeptide was immobilized on a plate by using 32 pmol/cm$^2$ (1.5 µg/cm$^2$) of C-FGF•A, a mixture 32 pmol/cm$^2$ (1 µg/cm$^2$) of C-274 and 32 pmol/cm$^2$ (0.5 µg/cm$^2$) of FGF or 0.32 pmol/cm$^2$ (0.5 µg/cm$^2$) of FGF (Becton Dickinson) according to the same manner as described in Example 2 (9). After pre-incubating 2 ml of a virus supernatant containing 1,000 cfu of PM5neo virus in respective plates and a control plate coated with BSA at 37° C. for 30 minutes, the plates were thoroughly washed with PBS. To each of these plates was added 2 ml of DMEM medium containing 2,000 NIH/3T3 cells and incubated at 37° C. for 2 hours in the absence of polybrene. Non adhered cells were collected by decantation and cells adhered to the plate were collected by trypsin treatment to detach them from the plate. The cells were combined. The resultant cell suspension was divided into two halves. One half portion was cultured in DMEM and the other portion was cultured in DMEM containing G418 at a final concentration of 0.75 mg/ml. Both portions were incubated at 37° C. for 10 days and the colonies appeared were counted. By taking the ratio of the number of G418 resistant (G418$^r$) colonies relative to that obtained in the medium without G418 as the gene transfer efficiency, the results are shown in FIG. 1. In FIG. 1, the abscissa indicates the functional materials used and the ordinate indicates the gene transfer efficiency.

As shown in FIG. 1, in case of 2 hour retrovirus infection, when the mixture of C-274 and FGF was used, G418$^r$ colonies were obtained at almost the same gene transfer efficiency as that of C-FGF•A where these two polypeptides were covalently coupled, though the gene transfer efficiency obtain by using FGF alone was lower than that of C-FGF•A.

In order to investigate in detail, the effect of immobilization of C-274 alone and FGF alone was compared with that of immobilization of a mixture thereof. Namely, assessment was carried out except that plates prepared with 32 pmol/cm$^2$ (1 µg/cm$^2$) of C-274, 32 pmol/cm$^2$ (0.5 µg/cm$^2$) of FGF and a mixture of 32 pmol/cm$^2$ of C-274 and 32 pmol/cm$^2$ of FGF, respectively, according to the same manner as described in Example 2 (9). The results are shown in FIG. 2. In FIG. 2, the abscissa indicates the functional materials used and the ordinate indicates the gene transfer efficiency.

As shown in FIG. 2, when using the plate on which immobilization was carried out with the mixture of C-274 and FGF, the gene transfer efficiency was higher than that using the plate on which only FGF was immobilized. And, no G418$^r$ colonies appeared in the plate on which immobilization was carried out with C-274 which did not have any retrovirus binding domain. This shows that, by combining FGF which has the retrovirus binding domain with C-274 which has the cell binding domain, the higher gene transfer efficiency can be obtained in comparison with that obtained by using FGF alone and that covalent coupling of the polypeptides is not necessary required for elaborating such effect of the combination of the polypeptides.

(2) Gene Transfer Using Mixture of Functional Materials

According to the same manner as described in Example 3 (1), assessment was carried out except that the polypeptide having retrovirus binding domain was replaced with ColV. In this experiment, the effect was investigated by mixing C-274 and ColV in various molar ratios. Namely, according to the same manner as described in Example 2 (9), immobilization on plates was carried out by using 330 pmol/cm$^2$ (6 µg/cm$^2$) of ColV, a mixture of 330 pmol/cm$^2$ (10 µg/cm$^2$) of C-274 and 330 pmol/cm$^2$ of ColV (molar ratio of C-274:ColV=10:10), a mixture of 100 pmol/cm$^2$ (3 µg/cm$^2$) of C-274 and 330 pmol/cm$^2$ of ColV (3:10), a mixture of 33 pmol/cm$^2$ (1 µg/cm$^2$) of C-274 and 330 pmol/cm$^2$ of ColV (1:10), 330 pmol/cm$^2$ (16 µg/cm$^2$) of C277-ColV and 330 pmol/cm$^2$ (10 µg/cm$^2$) of C-274, respectively. By using the plates thus prepared, the effect of retrovirus infection was investigated according to the same manner as described above. The results are shown in FIG. 3. In FIG. 3, the abscissa indicates the functional materials used and the ordinate indicates the gene transfer efficiency.

As shown in FIG. 3, in case of 2 hour infection, the infection efficiency of ColV immobilized plate was less than ½ of that of C277-ColV immobilized plate, while the infection efficiency of the plate on which immobilization was carried out with the mixture of ColV and its ¹/₁₀ amount (as the molecular number) of C274 was the same as that of C277-ColV immobilized plate. Then, the retrovirus infection enhancing activity of C-274 was ascertained as observed in the case of FGF. This effect was rather decreased in case that the amount of C-274 molecules relative to ColV molecules was increased. When a mixture containing the same amounts of ColV and C-274 was coated, there was no substantial difference between the mixture and ColV alone.

(3) Gene Transfer Using Mixture of Functional Materials

In order to investigate the effect on the gene transfer efficiency by immobilization of a mixture of a material having cell binding domain and a material having retrovirus binding domain, the following experiment was carried out. First, according to the same manner as described in Example 2 (9), immobilization of plates was carried out with 32 pmol/cm$^2$ (1 µg/cm$^2$) of C-274, 333 pmol/cm$^2$ (10 µg/cm$^2$) of H-271 and a mixture of 32 pmol/cm$^2$ (1 µg/cm$^2$) of C-274 and 333 pmol/cm$^2$ (10 µg/cm$^2$) of H-271, respectively. After pre-incubating 2 ml of a virus supernatant containing 1,000 cfu of PM5neo virus in respective plates at 37° C. for 30 minutes, the plates were thoroughly washed with PBS. To each of these plates was added 2 ml of DMEM medium containing 2,000 NIH/3T3 cells and incubated at 37° C. for 2 hours. Non adhered cells were collected by decantation and cells adhered to the plate were collected by trypsin treatment to detach them from the plate. The cells were combined. The resultant cell suspension was divided into two halves. One half portion was cultured in DMEM and the other portion was cultured in DMEM containing G418 at a final concentration of 0.75 mg/ml. Both portions were incubated at 37° C. for 10 days and the colonies appeared were counted. By taking the ratio of the number of G418$^r$ colonies relative to that obtained in the medium without G418 as the gene transfer efficiency, the results are shown in FIG. 4. In FIG. 4, the abscissa indicates the functional materials used and the ordinate indicates the gene transfer efficiency.

As shown in FIG. 4, when using the plate on which the mixture of C-274 and H-271 (molar ratio=1:10) was immobilized, the infection efficiency was significantly increased. No gene transfer was observed in C-274 immobilized plate.

(4) Gene Transfer Using C277-CS1

In order to investigate the effect on the infection efficiency by using C277-CS1 as a material having cell binding domain and immobilization of a mixture thereof and a material having retrovirus binding domain, the following experiment was carried out. As the material binding to a retrovirus, a polylysine [(Lys)$_n$, poly-L-lysine hydrobromide, molecular weight: 50,000-100,000, Wako Pure Chemical Co., Ltd.] and H-271 were used. As the cells, non-adherent cells; TF-1 cells (ATCC CRL-2003), were used. First, according to the same manner as described in Example 2 (9), immobilization on plates was carried out by using the following solutions: C-277-CS1 (33 pmol/cm$^2$, 1.1 µg/cm$^2$), polylysine (133 pmol/cm$^2$, 10 µg/cm$^2$), a mixture of C-277-CS1 (33 pmol/cm$^2$) and polylysine (133 pmol/cm$^2$), H-271 (333 pmol/cm$^2$, 10 µg/cm$^2$) and a mixture of C-277-CS1 (33 pmol/cm$^2$) and H-271 (333 pmol/cm$^2$) and CH-296 (33 pmol/cm$^2$, 2.1 µg/cm$^2$), respectively. To each plate was added RPMI 1640 medium [containing 5 ng/ml of GM-CFS (Petro Tech), 50 units/ml of penicillin and 50 µg/ml of streptomycin] containing 1×10$^4$ cfu of TKNEO virus, 1×10$^4$ of TF-1 cells and the plate was incubated at 37° C. for 24 hours. After incubation, non adhered cells were collected by decantation and cells adhered to the plate were collected by trypsin treatment to remove them from the plate. The cells were combined. Respective one fifth portions of the resultant cell suspension were transferred to two plates coated with CH-296 and incubated for 24 hours. Then, the medium of one portion was exchanged to the above medium and that of the other portion was exchanged to the above medium containing G418 at a final concentration of 0.75 mg/ml. Both portions were incubated at 37° C. for 8 days and the colonies appeared were counted. The incidence of G418$^r$ colonies (the gene transfer efficiency) was calculated based on the numbers of colonies appeared in the presence and absence of G418.

The results are shown in FIG. 5. In FIG. 5, the abscissa indicates the functional materials used and, the ordinate indicates the gene transfer efficiency. In FIG. 5, (a) represents the use of the polylysine as the retrovirus binding material and (b) represents the use of H-271. In comparison with the plate on which only retrovirus binding material was immobilized, the gene transfer efficiency is significantly increased by using the polylysine or H-271 together with C277-CS1 having the cell binding domain.

(5) Preparation of Polypeptide Derived from Erythropoietin

For using in gene transfer into the cells having erythropoietin receptor, a polypeptide derivative which was erythropoietin fused with glutathione-S-transferase (GST-Epo) was prepared. The amino acid sequence is shown in SEQ. ID No. 34 of the Sequence Listing. In this sequence, the amino acid sequence from 233rd amino acid to 398th amino acid corresponds to erythropoietin.

First, a plasmid was constructed by the following procedures to express GST-Epo. PCR was carried out by using cDNA library derived from human fetal liver (Clone tech) as a template and primers EPF1 and EPR1 (the nucleotide sequences of primers EPF1 and EPR1 are shown in SEQ. ID Nos. 35 and 36 of the Sequence Listing). A portion of the reaction mixture was taken out and, by using it as a template and primers EPF2 and EPR2 (the nucleotide sequences of primers EPF2 and EPR2 are shown in SEQ. ID Nos. 37 and 38 of the Sequence Listing), additional PCR was carried out. Amplified DNA fragments were recovered from the reaction mixture, digested with EcoRI and BamHI (both Takara Shuzo Co., Ltd.) and then subjected to agarose electrophoresis to recover a DNA fragment of about 520 bp which contained a region encoding erythropoietin. The resultant fragment was mixed with a plasmid vector pTV118N (Takara Shuzo Co., Ltd.) which digested with EcoRI (Takara Shuzo Co., Ltd.) and BamHI to ligate it to the plasmid. Then, *E. coli* JM109 was transformed with the plasmid. A transformant maintaining the above plasmid was selected from the resultant transformants to prepare a plasmid and named as plasmid pEPO. Then, the plasmid pEPO thus obtained was digested with EcoRI and SalI (Takara Shuzo Co., Ltd.) and subjected to agarose electrophoresis to recover a DNA fragment of about 0.5 kb. This fragment was mixed with a plasmid vector pGEX5X-3 (Pharmacia) digested with EcoRI and SalI to ligate them. *E. coli*. JM109 was transformed with the resultant plasmid. A transformant maintaining the above plasmid was selected from the resultant transformants to prepare a plasmid and the plasmid was named as pGSTEPO. This plasmid encodes GST-EPO wherein the amino acid sequence of erythropoietin is coupled to the C-terminal of glutathione-S-transferase derived from the vector. The nucleotide sequence encoding GST-EPO on the plasmid pGSTEPO is shown in SEQ. ID No. 39 of the Sequence Listing.

The polypeptide GST-Epo was prepared by the following procedures. Seven culture tubes each containing 5 ml of LB broths containing 100 µg/ml of ampicillin were provided and *E. coli* JM109 transformed with the above plasmid pGSTEPO, *Escherichia coli* JM109/pGSTEPO, was inoculated into each broth, followed by incubating at 37° C. overnight. Then, seven 2 liter Erlenmeyer flasks each containing 500 ml of the same broth were provided and 5 ml portions of the above culture were inoculated into the flasks, followed by incubating at 37° C. 3.5 Hours after starting incubation, IPTG was added at the final concentration of 1 mM and incubation was continued for additional 3.5 hours. After completion of culture, cells were recovered from the culture broth by centrifugation, suspended in 100 ml of PBS containing 1 mM PMSF and 1 mM EDTA and disrupted by sonication. To the disrupted solution was added 100 ml of PBS containing 1 mM PMSF, 1 mM EDTA and 2% Triton X-100. The mixture was allowed to stand on ice for 30 minutes and centrifuged to collect a supernatant. The resultant supernatant was filtered through a filter of 0.45 µm (Millipore) and applied on a glutathione-Sephallose 4B column (Pharmacia, 3 ml) equilibrated with PBS. After washing the column with PBS, the column was eluted with 50 mM Tris-HCl containing 10 mM glutathione (pH 8.0). The eluate was analyzed by SDS-polyacrylamide gel electrophoresis and a fraction containing a polypeptide having a molecular weight of about 44,000 was collected. The fraction was dialyzed against PBS. A dialyzed sample was applied on Resource Q column (Pharmacia) equilibrated with PBS. After washing the column with PBS, the column was eluted with PBS having NaCl gradient of from 0 M to 0.6 M. According to the same manner as described above, the column was eluted with 50 mM Tris-HCl containing glutathione (pH 8.0) to collect a fraction containing a polypeptide having a molecular weight of about 44,000. This was subjected to ultrafiltration with Centricon 10 (Amicon) to concentrate to about 50 μl. Further, it was filtrated with Ultrafree C3GVSTRL (Millipore) and the filtrate was subjected to gel filtration chromatography using Superdex 200 column (Pharmacia, equilibrated with PBS). An eluted fraction containing a polypeptide having a molecular weight of about 44,000 was collected and this was used as a GST-Epo polypeptide solution in the subsequent experiments. In this GST-Epo solution, about 50% of the total proteins were GST-Epo.

(6) Gene Transfer into Erythropoietin Receptor Expressing Cells

The effect of gene transfer using erythropoietin as a material having cell binding activity was investigated by using two kinds of cells, TF-1 which expresses an erythropoietin receptor and HL-60 (ATCC CCL-240) which does not express the erythropoietin receptor. In this investigation, the above polypeptide derivative of erythropoietin (GST-Epo), was used as erythropoietin and a polylysine was used as the retrovirus biding material. First, according to the same manner as described in Example 2 (9), immobilization on plates was carried out by using GST-Epo corresponding to 34 pmol/cm$^2$ (1.5 μg/cm$^2$), polylysine (133 pmol/cm$^2$, 10 μg/cm$^2$), a mixture of GST-Epo (34 pmol/cm$^2$) and polylysine (133 pmol/cm$^2$), respectively. To each plate was added a medium containing 1×10$^4$ cfu of TKNEO virus and 1×10$^4$ of cells and the plate was incubated at 37° C. for 24 hours. As the medium, RPMI1640 medium (containing 5 ng/ml of GM-CFS, 50 units/ml of penicillin and 50 μg/ml of streptomycin) was used for TF-1 and RPMI medium (Nissui, containing 10% FCS, 50 units/ml of penicillin, 50 μg/ml of streptomycin) was used for HL-60. After incubation, non adhered cells were collected by decantation and cells adhered to the plate were collected by trypsin treatment to remove them from the plate. The cells were combined. Respective one fifth portions of the resultant cell suspension were transferred to two CH-296 immobilized plates and incubated for 24 hours. Then, the medium of one portion was exchanged to the above medium and that of the other portion was exchanged to the above medium containing G418 at a final concentration of 0.75 mg/ml. Both portions were incubated at 37° C. for 8 days and the colonies appeared were counted. The incidence of G418$^r$ colonies (the gene transfer efficiency) was calculated based on the numbers of colonies appeared in the presence and absence of G418.

The results are shown in FIG. 6. In FIG. 6, the abscissa indicates the functional materials used and the ordinate indicates the gene transfer efficiency, respectively. In case of using TF-1 cells as shown in FIG. 6 (a), although gene transfer was taken place to some extent in the plate on which only the polylysine was immobilized, the higher gene transfer efficiency was obtained in the presence of GST-Epo. On the other hand, in case of using HL-60 as shown in FIG. 6 (b), no increase in the gene transfer efficiency was observed in the presence of GST-Epo. These results showed that target cell specific gene transfer was possible by using erythropoietin.

In addition, an experiment of gene transfer into TF-1 cells was carried out by replacing the retrovirus binding material with H2-547. According to the same manner as described in Example 2 (9), immobilization on plates was carried out by using H2-547 (333 pmol/cm$^2$, 20 μg/cm$^2$), GST-Epo corresponding to 34 pmol/cm$^2$, 1.5 μg/cm$^2$) and a mixture of GST-Epo (34 pmol/cm$^2$) and H2-547 (333 pmol/cm$^2$, 20 μg/cm$^2$), respectively. At the same time, a control experiment was carried out by using BSA immobilized plate.

The results are shown in FIG. 7. In FIG. 7, the abscissa indicates the functional materials used and the ordinate indicates the gene transfer efficiency, respectively. As shown in FIG. 7, in case of using H2-547, the gene transfer efficiency into TF-1 cells was increased in the presence of GST-Epo.

(7) Gene Transfer Using Beads on which Mixture of Functional Materials was Immobilized Whether the retrovirus infection efficiency can be increased by using beads on which both material having cell binding domain and material having retrovirus binding domain were immobilized or not was investigated.

Beads on which polypeptides were immobilized were prepared according to the following procedures. As beads, polystyrene beads having the diameter of 1.14 μm (Polybeads Polystyrene Microsphere, manufactured by PolyScience) were used. To 20 μl of a 2.5% suspension of the above beads were added 80 μl of ethanol and 2 ml of various polypeptide solutions in PBS, followed by allowing to stand, overnight at 4° C. To this were added BSA and PBS to prepared 4 ml of 1% BSA/PBS suspension. Beads were recovered from the suspension by centrifugation and suspended in 5 ml of 1% BSA/PBS again. Then, the suspension was allowed to stand at room temperature for 1 hour to obtain a suspension of polypeptide immobilized beads. As the polypeptide solutions, 100 μg/ml of C-274, 100 μg/ml of H-271, 100 μg/ml of CH-271, 100 μg/ml of CH-296 and a mixture of 100 μg/ml of H-271 and 10 μg/ml of C-274. As a control, beads coated with 2% BSA solution was prepared according to the same manner.

One tenth portion of the polypeptide immobilized beads thus prepared was recovered from the above suspension and incubated at 37° C. overnight together with 2,000 of TF-1 cells and 1,000 cfu of TKNEO virus supernatant, respectively. The cells were recovered and suspended in RPMI medium [containing 10% of FCS, 5 ng/ml of GM-CFS (Petrotech), 50 units/ml of penicillin and 50 μg/ml of streptomycin] containing 0.3% of Bacto agar (Difco) and seeded on a 35 mm plate made of the above medium containing 0.5% of Bacto agar. Two mediums containing 0.75 mg/ml of G418 and without G418 were used. The plate was incubated in 5% CO$_2$ at 37° C. for 14 days. Colonies which appeared in the presence of G418 and in the absence of G418 were counted and the appearance ration of G418$^r$ colonies (gene transfer efficiency) was calculated.

The results are shown in FIG. 8. In FIG. 8, the abscissa indicates the functional material used and BSA and the ordinate indicates the gene transfer efficiency. When using the beads on which the mixture of H-271 and C-274 was immobilized, the higher gene transfer efficiency was obtained in comparison with using beads on which only H-271 alone was immobilized and beads on which immobilized with CH-271 or CH-296 having the retrovirus binding domain and cell binding domain on the same molecule, respectively.

Example 4

(1) Gene Transfer Using FGF and C-FGF•A

The effect of FGF (Becton Deckinson) and the polypeptide represented by SEQ. ID No. 4 (C-FGF•A) on retrovirus infection was investigated by NIH/3T3 cell colony forming assay. Namely, assessment was carried but according to the same manner as described in Example 2 (9) by immobilizing FGF (132 pmol/cm$^2$, 2.25 μg/cm$^2$) and C-FGF•A (133 pmol/cm$^2$, 6.3 μg/cm$^2$) on plates, respectively, and immobilizing BSA on a control plate. To each plate was added 2 ml of a virus supernatant containing 1,000 cfu of PM5neo virus and pre-incubated at 37° C. for 30 minutes, followed by thoroughly washing with PBS. To this plate was added 2 ml of DMEM medium containing 2,000 NIH/3T3 cells and incubated at 37° C. for 24 hours, followed by incubation in a selection medium containing 0.75 mg/ml of G418 for 10 days. Colonies were stained and counted. The results are shown in FIG. 9. In FIG. 9, the abscissa indicates the functional material used and the ordinate indicates the number of G418$^r$ colonies appeared.

As shown in FIG. 9, no colony appeared in the control plate coated on which BSA was immobilized. On the other hand, when using FGF and C-FGF•A immobilized plate, G418$^r$ colonies were identified in both plates. This result shows that both FGF and C-FGF•A have retrovirus binding domain and that C-FGF•A wherein the cell binding domain polypeptide of fibronectin was coupled showed superior gene transfer to FGF.

(2) Relation Between Concentration of C-FGF•A and Gene Transfer Efficiency

The gene transfer efficiencies were compared by using plates coated with various concentrations of C-FGF•A. Infection with retrovirus was carried out according to the same procedures as those in Example 4 (1) except for the use of a plate prepared with 0.521 pmol/cm$^2$ (0.0247 µg/cm$^2$)-5.21 pmol/cm$^2$ (0.247 µg/cm$^2$) of C-FGF•A according to the method described in Example 2 (9), and a BSA immobilized plate (control plate). After virus infection treatment, the non-adhered were collected by decantation and the cells adhered to the plate were collected by trypsin treatment to remove them from the plate. The cells thus collected were combined. The resulting cell suspension was divided into two halves, one half portion was cultured with DMEM and the other was cultured with DMEM containing G418 at the final concentration of 0.75 mg/ml. Both portions were incubated at 37° C. for 10 days and the number of colonies which appeared was counted. A ratio of the number of G418$^r$ colonies relative to that of colonies obtained on a medium containing no G418 was taken as the gene transfer efficiency.

The results are shown in FIG. 10. In FIG. 10, the abscissa indicates the concentration of C-FGF•A used for immobilization on the plate and the ordinate indicates the gene transfer efficiency. The experiment result of control plate was also plotted at the polypeptide concentration of 0 µmol/cm$^2$. As shown in FIG. 10, the gene transfer efficiency was concentration-dependently increased as increase in the C-FGF•A concentration upon immobilization.

(3) Gene Transfer into HL-60 Cell

As regards the retrovirus infection of HL-60 cell (ATCC CCL-240) which is a non-adherent cell, the effect of the presence of various polypeptides was investigated according to the following procedures. Namely, to each of plate prepared using 100 pmol/cm$^2$ of C-FGF•A (4.8 µg/cm$^2$) or C-FGF-CS1 (5.1 µg/cm$^2$) according to the method of Example 2 (9) and a control plate on which BSA was immobilized was added 2 ml of RPMI medium (containing 10% of FCS, 50 units/ml, of penicillin and 50 µg/ml of streptomycin) containing 1×10$^4$ cfu of TKNEO virus and 2,000 cells of HL-60, followed by incubation at 37° C. for 24 hours. After incubation, the non-adhered cells were collected by decantation and the cells adhered to the plate were collected by pipetting and these cells were combined. Each ½ portion of the resulting cell suspension was transferred to a plate coated with CH-296, incubated for 24 hours and the medium was exchanged with RPMI medium containing the final concentration of 0.75 mg/ml of G418. After incubation at 37° C. for 12 days, the number of colonies which appeared was counted. The number of G418$^r$ colonies obtained by using each polypeptide is shown in FIG. 11. In FIG. 11, the abscissa indicates the functional material and the ordinate indicates the number of G418$^r$ colonies, respectively.

As shown in FIG. 11, the number of G418$^r$ colonies was remarkably increased when C-FGF•A or C-FGF-CS1 immobilized plate was used, indicating that these polypeptides promote the infection of HL-60 cell with retrovirus.

(4) Gene Transfer into Mouse Bone Marrow Cells

For investigating the effect of FGF, C-FGF•A and C-FGF-CS1 on retrovirus infection of mouse myeloid cells, the following experiment was carried out.

150 mg/kg 5-fluorouracil (5-FU, Amlesco) was administered intraperitoneally to mouse (C3H/HeJ), 6 to 8 weeks age, femur and tibia were isolated 2 days after administration to collect bone marrow. The resulting bone marrow was subjected to density gradient centrifugation using Ficoll-Hypaque (density 1.0875 g/ml, Pharmacia) to obtain a low density mononuclear cell fraction which was used as mouse bone marrow cells.

The mouse bone marrow cells were pre-stimulated prior to infection with retrovirus according to a method by Luskey et al. (Blood, 80, 396 (1992)). Namely, the mouse bone marrow cells were added to α-MEM (Gibco) containing 20% of FCS, 100 units/ml of recombinant human interleukin-6 (rhIL-6, Amgen), 100 ng/ml of recombinant mouse stem cell factor (rmSCF, Amgen), 50 units/ml of penicillin and 50 µg/ml of streptomycin at cell density of 1×10$^6$ cells/ml, followed by incubation at 37° C. for 48 hours in 5% CO$_2$. The pre-stimulated cells including those adhered to the container were collected by aspiration with a pipette.

Each 2 ml of the medium, used for the above pre-stimulation, containing 1×10$^6$ pre-stimulated cells and 1×10$^4$ cfu of PM5neo virus was added to the plate prepared with 236 pmol/cm$^2$ (4 µg/cm$^2$) of FGF, 169 pmol/cm$^2$ (8 µg/cm$^2$) of C-FGF•A or 159 pmol/cm$^2$ (8 µg/cm$^2$) of C-FGF-CS1 according to the method described in Example 2 (9), and a BSA immobilized plate (control plate), followed by incubation at 37° C. After 2 hours, a medium (2 ml) containing the same amount of virus was freshly added to each, plate, followed by continuing incubation for 22 hours. After completion of incubation, the non-adhered cells were collected by decantation and the cells adhered to the plate were collected using a cell dissociation buffer (CDB, containing no enzymes, Gibco) and these cells were combined and washed twice with the same buffer. The number of the cells was counted. The collected cells were subjected to HPP-CFC (High Proliferative Potential-Colony Forming Cells) assay.

HPP-CFC assay was carried out according to a method by Bradley et al. (Aust. J. Exp. Biol. Med. Sci., 44, 287-293 (1966)). As a medium, 1%/0.66% layered soft agar medium with or without G418 at the final concentration of 1.5 mg/ml was used. Infected cells was added thereto at 1×10$^4$ cells/well, followed by incubation at 37° C. for 13 days in 10% CO$_2$. After completion of incubation, the colonies which appeared were observed with an inverted microscope and the number of high density colonies (having the diameter of not less than 0.5 mm) derived from HPP-CFC was counted to calculate the incidence (gene transfer efficiency) of G418$^r$ colonies. The results are shown in FIG. 12. In FIG. 12, the abscissa indicates the functional material used and BSA and the ordinate indicates the gene transfer efficiency.

As shown in FIG. 12, no G418$^r$ colonies appeared in the plate coated with BSA as a control, while the G418$^r$ colonies were obtained when the plates on which the above respective polypeptides were immobilized were used. The gene transfer efficiencies were increased in an order of in FGF, C-FGF•A and C-FGF-CS1, suggesting that the presence of the cell adhesion domain derived from fibronectin and CS-1 polypeptide which has the binding activity to cells domain increase the infection of bone marrow cells with retrovirus.

(5) Relation Between Concentration of C277-ColV Used for Immobilization on Plate and Gene Transfer Efficiency The gene transfer efficiencies were compared by using plates coated with various concentration of C277-ColV according to the following procedures. The plates were prepared according to the method described in Example 2 (9) using 0.1 pmol/cm$^2$ (0.1 μg/cm$^2$)-416 pmol/cm$^2$ (20 μg/cm$^2$) of C277-ColV. 2 ml of a virus supernatant containing 1,000 cfu of PM5neo virus was added to respective plates and pre-incubation was carried out at 37° C. for 30 minutes, followed by washing thoroughly with PBS. To this plate was added 2 ml of DMEM medium containing 2,000 NIH/3T3 cells and the plate was incubated at 37° C. for 24 hours. The non-adhered cells were collected by decantation and the cells adhered to the plate were collected by trypsin treatment to detach them from the plate and these cells were combined. The resulting cell suspension was divided into two halves and one half portion was cultured in DMEM and the other portion was incubated in DMEM containing G418 at the final concentration of 0.75 mg/ml at 37° C. for 10 days and the number of the colonies appeared was counted. A ratio of the number of G418$^r$ colonies relative to that of colonies obtained in a medium containing no G418 was taken as the gene transfer efficiency. The results are shown in FIG. 13. In FIG. 13, the abscissa indicates the functional material used and the ordinate indicates the gene transfer efficiency.

As shown in FIG. 13, when C277-ColV immobilized plate was used, the gene transfer efficiency was increased depending upon the concentration of C277-ColV used for immobilization.

(6) Gene Transfer Using Polylysine

Binding of a polylysine [(Lys)$_n$] to a retrovirus was investigated by the following procedures. As a polylysine, poly-L-lysine hydrobromide (molecular weight: 50,000-100,000, Wako Pure Chemical) was used and according to the same manner as described in Example 2 (9), it was immobilized on a plate by using 133 pmol/cm$^2$ (10 μg/cm$^2$) polylysine solution in PBS. The gene transfer efficiencies of this plate and a control plate on which BSA was immobilized was assessed according to the same manner as described in Example 4 (2). The results are shown in FIG. 14. In FIG. 14, the abscissa indicates the functional material and the ordinate indicates the gene transfer efficiency. As shown in FIG. 14, no colony appeared in the control plate coated with BSA, while G418$^r$ colonies appeared in the polylysine immobilized plate, suggesting that, after washing, the retrovirus remained on the plate because of binding of the retrovirus to the polylysine immobilized on the plate.

Example 5

(1) Gene Transfer Using Polymer of Polypeptide

The gene transfer using a polymer of a polypeptide was carried out without immobilization of the polypeptide on a plate. To a plate pre-coated with BSA according to the method described in Example 2 (9) was added each 2 ml of DMEM containing 1,000 cfu of PM5neo virus, 2,000 cells of NIH/3T3 cell and respective polypeptides (H-271, CH-271, H2-547 and CH2-826) at the final concentration of 0.63 nmol/ml, followed by incubation for 24 hours. The non-adhered cells were collected by decantation and the cells adhered to the plate were collected by trypsin treatment to remove them from the plate. Then, these cells were combined. As a control, the same gene transfer experiment without addition of any polypeptide was carried out according to the same manner. The resulting cell suspension was divided into two halves and one half portion was cultured in DMEM. The other portion was cultured in DMEM containing G418 at the final concentration of 0.75 mg/ml. Both portions were incubated at 37° C. for 10 days and colonies appeared were counted. By taking the ratio of the number of G418$^r$ colonies relative to the number of colonies appeared in the medium without G418 as the gene transfer efficiency, the results are shown in FIG. 15. In FIG. 15, the abscissa indicates the functional material used and the ordinate indicates the gene transfer efficiency.

As seen from FIG. 15, the gene transfer efficiency in the presence of H2-547 was significantly higher than that in the presence of H-271 and, in case of CH2-826, the gene transfer efficiency equal to or higher than that of CH-271 was obtained.

Further, more detailed investigation was carried out according to the same manner as described above except that CH-271, CH-296 and H2-547 were used as polypeptides in both amounts of 0.126 nmol (the final concentration of. 0.063 nmol/ml) and 1.26 nmol (the final concentration of 0.63 nmol/ml) for respective plates. The results are shown in FIG. 16. In FIG. 16, the abscissa indicates the functional materials used and their amounts and the ordinate indicates the gene transfer efficiency.

As shown in from FIG. 16, when H2-547 was used, the gene transfer efficiency was significantly higher than those of CH-271 and CH-296 in either amount of the polypeptide.

(2) Gene Transfer into Mouse Bone Marrow Cells Using H2S-573

For investigation of the effect of H2S-573 on retrovirus infection of bone marrow cells, an experiment of gene transfer into mouse bone marrow cells was carried out according to the same manner as described in Example 4 (4).

Mouse bone marrow cells were prepared according to the same manner as described in the above Example and the cells were pre-stimulated.

As plates for retrovirus infection, in addition to H2S-573 (160 pmol/cm$^2$, 10 μg/cm$^2$) immobilized plate, CH-296 (132 pmol/cm$^2$, 8.3 μg/cm$^2$) immobilized plate and, as a control, BSA immobilized plate were used. The results obtained by HPP-CFC assay are shown in FIG. 17. In FIG. 17, the abscissa indicates the functional material used and the ordinate indicates the gene transfer efficiency.

As shown in FIG. 17, no high density colonies of G418$^r$ appeared in the plate coated with BSA as a control. Although about 50% of the gene transfer efficiency was obtained in CH-296 immobilized plate, high density colonies of G418$^r$ were obtained at the higher efficiency in case of using H2S-573 immobilized plate.

Example 6

(1) Gene Transfer Using Functional Material without Immobilization

The effect on the retrovirus infection efficiency when a polypeptide was present on a plate without immobilization was investigated as follows. Namely, to a plate pre-coated with BSA according to the method described in Example 2 (9) was added each 2 ml of DMEM medium containing 100 cfu of PM5neo virus, 2,000 cells of NIH/3T3 cell and CH-296 at the final concentration of 10, 40, 250 µg/ml (each corresponding to 0.158, 0.632 and 3.950 nmol/ml), followed by incubation for 24 hours. The non-adhered cells were collected by decantation and the cells adhered to the plate were collected by trypsin treatment to remove them from the plate. These cells were combined. The resulting cell suspension was transferred to a 10 cm cell culture plate, followed by incubation for 2-4 hours. The medium was exchanged with DMEM containing G418 at the final concentration of 0.75 mg/ml, followed by incubation for additional 10 days. Separately, as a control, a plate without CH-296, and a plate on which 32 pmol/cm$^2$ (2 µg/cm$^2$) or 127 pmol/cm$^2$ (8 µg/cm$^2$) of CH-296 was immobilized were prepared and the above procedures were carried out by adding a virus supernatant and cells thereto. The number of G418$^r$ colonies thus obtained was counted and the results are summarized in Table 1.

TABLE 1

| Plate | CH-296 | Number of G418$^r$ colonies |
|---|---|---|
| BSA | — | 5 |
| BSA | 10 µg/ml | 41 |
| BSA | 40 µg/ml | 66 |
| BSA | 250 µg/ml | 92 |
| CH-296 (32 pmol/cm$^2$) | — | 55 |
| CH-296 (127 pmol/cm$^2$) | — | 47 |

As shown in Table 1, when cell, virus and CH-296 were present together in the solution, the number of G418$^r$ colonies was considerably increased in comparison with the absence of CH-296. The number was equal to or higher than that obtained by the use of the plate coated with CH-296. In addition, when a CH-296 solution was added, at the above respective concentrations, to a plate coated with BSA and, after allowing to stand for a while, the plate was washed and used for virus infection experiment, the number of G418$^r$ colonies obtained was similar to that in the case without addition of CH-296 was obtained. From this, it is understood that CH-296 does not bind to a BSA immobilized. Therefore, it is considered that the above retrovirus infection promoting effect by CH-296 is not due to the adhesion of CH-296 in the solution to a plate during incubation.

(2) Gene Transfer Using Functional Material without Immobilization

The effect on the retrovirus infection efficiency when polypeptides were present together on a plate without immobilization was investigated as follows. Namely, to a plate pre-coated with BSA according to the method described in Example 2 (9) was added each 2 ml of DMEM medium containing 1,000 cfu of PM5neo virus, 2,000 cells of NIH/3T3 cell, and C-FGF•A, ColV and C277-ColV at the final concentration of 1.67 nmol/ml, respectively, followed by incubation at 37° C. for 24 hours. The non-adhered cells were collected by decantation and the cells adhered to the plate were collected by trypsin treatment to remove them from the plate. These cells were combined. The resulting cell suspension was divided into two halves, one half portion was cultured with DMEM and the other portion was cultured with DMEM containing G418 at the final concentration of 0.75 mg/ml. Both portions were incubated at 37° C. for 10 days and the number of colonies which appeared was counted. A ratio of the number of G418$^r$ colonies relative to that of colonies obtained on a medium containing no G418 was taken as the gene transfer efficiency. The results are shown in FIG. 18. In FIG. 18, the abscissa indicates the functional materials used and the ordinate indicates the gene transfer efficiency.

As shown in FIG. 18, when virus infection is taken place in the presence of each polypeptide, the higher gene transfer efficiency is obtained. Thus, it is clear that, even when these polypeptides are not immobilized on plates, the retrovirus infection is promoted.

(3) Gene Transduction of Non-Adherent Cells by Using Functional Material without Immobilization The effect on the gene transfer efficiency into non-adherent cells by a polypeptide without immobilization was investigated as follows. Namely, to each of a plate prepared with 333 pmol/cm$^2$ (10 µg/cm$^2$) of H-271 and according to the same manner as that described in Example 2 (9) and a control plate on which BSA was immobilized was added 2 ml of RPMI medium (containing 5 ng/ml of GM-CFS, 50 units/ml of penicillin and 50 µg/ml of streptomycin) containing 1×10$^4$ cfu of TKNEO virus and 1×10$^4$ cells of TF-1 cells. To the BSA immobilized plate was further added H-271 at the final concentration of 50 µg/ml (1.67 nmol/ml) of H-271. Each plate was incubated at 37° C. for 24 hours. After incubation, the non-adhered cells were collected by decantation and the cells adhered to the plate were Collected by trypsin treatment. These cells were combined. Each 1/5 portion of the resulting cell suspension was transferred to two plates coated with CH-296, incubated for 24 hours. The medium of one plate was exchanged with the above medium and the medium of the other plate was exchanged with the above medium containing G418 at the final concentration of 0.75 mg/ml. After incubation at 37° C. for 8 days, the number of colonies which appeared was counted. The incidence (gene transfer efficiency) was calculated based on the number of colonies appeared in the presence and absence of G418. The results are shown in FIG. 19. In FIG. 19, the abscissa indicates the functional material and its form used and the ordinate indicates the gene transfer efficiency.

As shown in FIG. 19, when non-immobilized H-271 is used, the gene transfer efficiency obtained is higher than that obtained by using immobilized H-271. Then, it has been shown that, when using H-271 for gene transduction of TF-1 cells, a non-immobilized state is preferred.

(4) Elucidation of Mechanism of Retrovirus Infection Promotion by Polypeptide In order to ascertain that promotion of retrovirus infection to cells by the polypeptide without immobilization as shown in the above Examples resulted from binding of the cells to the polypeptide and binding of the polypeptide to the retrovirus, the following experiment was carried out. First; to BSA immobilized plates prepared with the method described in Example 2 (9) were added 2 ml of DMEM containing 1,000 cells of NIH/3T3 cell, followed by incubation at 37° C. for 24 hours. The medium was removed from the plates, each 2 ml of 1.67 nmol/ml of H-271, CH-271, C-FGF•A and PBS as a control was added thereto, respectively, followed by incubation at 37° C. for 2.5 hours. The plates were washed with a Hanks' balanced salt solution (HBSS, Gibco) containing 25 mM of HEPES. 2 ml of a virus supernatant containing 1,000 cfu of PM5neo virus was added to the plates, followed by incubation at 37° C. for 30 minutes. The plates were washed with PBS. To these plates were added 2 ml of DMEM, followed by incubation at 37° C. for 24 hours. The non-adhered cells were collected by decantation and the cells adhered to the plate were collected by trypsin treatment to detach them from the plate. These cells were combined, respectively. Each cell suspension thus obtained was divided into two halves, one, half portion was cultured with DMEM and the other portion was cultured with DMEM containing G418 at the final concentration of 0.75 mg/ml. Both portions were incubated at 37° C. for 10 days and the number of colonies which appeared was counted. A ratio of the number of G418$^r$ colonies relative to that of colonies obtained on a medium containing no G418 was taken as the gene transfer efficiency. The results are shown in FIG. 20. In FIG. 20, the abscissa indicates the functional materials used and a control the ordinate indicates the gene transfer efficiency.

As shown in FIG. 20, when virus infection was carried out after treatment of the cells on the plate with the above polypeptide solution, the remarkable increase in the infection efficiency was observed. This suggests that the infection efficiency is increased by binding of the polypeptide to cells and further binding of the retrovirus to the polypeptide on the cells.

The similar experiment was carried out except that the polypeptide to be added was replaced with 0.29 nmol/ml of C-FGF•A and 0.79 nmol/ml of CH296, respectively. The results are shown in FIG. 21. In FIG. 21, the abscissa indicates the functional materials used and a control the ordinate indicates the gene transfer efficiency. As shown in FIG. 21, the increase in the gene transfer efficiency was observed in the case of C-FGF•A and CH-296. Thus, the above activity was confirmed on C-FGF•A. At the same time, it was shown that CH-296 has the same activity to promote the retrovirus infection by the same mechanism.

Example 7

(1) Gene Transfer Using Functional Material Immobilized on Beads

Whether the retrovirus infection efficiency could be increased by using beads coated with the functional material or not was investigated according to the following procedures. As beads, polystyrene beads having the diameter of 1.14 μm (Polybeads Polystyrene Microsphere, manufactured by PolyScience) were used. To 20 μl of a 2.5% suspension of the above beads was added 80 μl of ethanol, and 2 ml of 40 μg/ml of CH-296 was added thereto, followed by allowing to stand overnight at 4° C. To this were added BSA and PBS to prepare a 1% BSA/PBS suspension (4 ml), beads were recovered by centrifugation and 5 ml of a 1% BSA/PBS suspension was prepared again to allow to stand at room temperature for 1 hour to obtain a suspension of CH-296 immobilized beads. As a control, beads were prepared according to the same manner except that the immobilization was carried out by using 2% BSA instead of the CH-296 solution.

One tenth portion (0.5 ml) was taken from the above bead suspension and the beads were recovered by centrifugation. DMEM containing 1,000 cfu of PM5neb virus was added thereto, followed by incubation at 37° C. for 30 minutes. The beads were washed twice with 1% BSA/PBS, suspended in 2 ml of DMEM and 1 ml of which was transferred to a plate. 1 ml of DMEM containing 3×10$^5$ cells of NIH/3T3 cell was added thereto, followed by incubation in $CO_2$ incubator at 37° C. for 24 hours. Thereafter, the medium was exchanged with DMEM containing G418 at the final concentration of 0.75 mg/ml, followed by incubation for another 10 days. Colonies which appeared were stained and counted. The results are shown in Table 2.

As shown in Table 2, when beads coated with CH-296 were used, 264 colonies of G418$^r$ appeared, while no resistant colonies were obtained in case of using the beads coated with BSA as a control. This suggests that even immobilization of CH-296 on beads has the effect for increasing retrovirus infection efficiency as in case of immobilization on a plate.

TABLE 2

| Beads | Number of G418$^r$ colonies |
|---|---|
| BSA immobilized (control) | 0 |
| CH-296 immobilized | 264 |

(2) Gene Transfer into Mouse Bone Marrow Cells Using Beads on which Functional Material was Immobilized The possibility of increase in the retrovirus infection efficiency of mouse bone marrow cells with beads coated with the functional material was investigated according to the following procedures.

The mouse bone marrow cells were prepared according to the same manner as described in Example 4 (4) and pre-stimulated.

Each 2 ml of the medium, used for the above pre-stimulation, containing 1×10$^6$ pre-stimulated cells and 1×10$^4$ cfu of PM5neo virus was added to a plate coated with BSA according to the same manner as described in Example 2 (9) and the similar plate coated with BSA to which 1/10 portion of the CH-296 immobilized beads as prepared in Example 7 (1), followed by incubation at 37° C. After 2 hours, a medium (2 ml) containing the same amount of virus was freshly added to each plate, followed by continuing incubation for 22 hours. After completion of incubation, the non-adhered cells were collected by decantation and the cells adhered to the plate were collected using a cell dissociation buffer (CDB, containing no enzymes, Gibco) and these cells were combined and washed twice with the same buffer. The number of the cells was counted. The collected cells were subjected to HPP-CFC assay according to the same manner as described in Example 4 (4).

The results are shown in FIG. 22. In FIG. 22, the abscissa indicates the functional material and its form used and the ordinate indicates the gene transfer efficiency. As shown in the results, it is understood that the retrovirus infection efficiency of mouse bone marrow cells can also be increase by using CH-296 immobilized beads.

Example 8

(1) Gene Transfer Using H-271 and CH-271

The effects of H-271 on retrovirus infection was assessed by pre-incubating a virus supernatant in plates coated with H-271 and CH-271 which was known to promote retrovirus infection, respectively, after thoroughly washing the plates, determining the remaining amount of the virus by NIH/3T3 cell colony formation assay and comparing the results of both plates. Namely, according to the same manner as described in Example 2 (9), plates were prepared with various concentrations of H-271 [67 pmol/cm$^2$ (2 μg/cm$^2$) to 333 pmol/cm$^2$ (10 μg/cm$^2$)] and CH-271 [67 pmol/cm$^2$ (4 μg/cm$^2$) to 333 pmol/cm$^2$ (20 μg/cm$^2$)], respectively. To each plate was added 2 ml of a virus supernatant containing 1,000 cfu of PM5neo virus and pre-incubated at 37° C. for 30 minutes, followed by thoroughly washing with PBS. To this plate was added 2 ml of DMEM medium containing 2,000 NIH/3T3 cells and incubated at 37° C. for 24 hours, followed by incubation in a selection medium containing 0.75 mg/ml of G418 for 10 days. Colonies were stained and counted. The results, are shown in FIG. 23. FIG. 23 is a graph illustrating the relation between the functional material and the gene transfer efficiency. In FIG. 23, the abscissa indicates the amount of the functional material used and the ordinate indicates the number of G418$^r$ colonies.

As shown in FIG. 23, when using CH-271 immobilized plate, the number of G418$^r$ colonies appeared was almost the same regardless of the concentration of the polypeptide. On the other hand, in case of H-271, the number of colonies appeared was increased depending upon the concentration as increase in the concentration of the polypeptide used in immobilization and, in case of the plate prepared with 333 pmol/cm$^2$ of H-271, the number of the colonies appeared was almost the same as that of CH-271. This suggests that the equivalent virus infection efficiency to that of CH-271 can be obtained, when a sufficient amount of H-271 is immobilized on a plate.

(2) Gene Transfer Using C-FGF•A

The effects of C-FGF•A on retrovirus infection was investigated by NIH/3T3 cell colony assay. Namely, assessment was carried out according to the same manner as described in Example 8 (1) except for the use of plates prepared with 127 pmol/cm$^2$ (6 μg/cm$^2$) of C-FGF•A, 127 pmol/cm$^2$ (7.6 μg/cm$^2$) of CH-271 and 127 pmol/cm$^2$ (8 μg/cm$^2$) of CH-289 according to the method described in Example 2 (9) and a control plate on which BSA was immobilized. The results are shown in FIG. 24. FIG. 24 is a graph illustrating the relation between the functional materials and the gene transfer efficiencies. In FIG. 24, the abscissa indicates the functional materials and, BSA and the ordinate indicates the gene transfer efficiency.

As shown in FIG. 24, no colony appeared in the control plate on which BSA was immobilized. On the other hand, when using the plate on which C-FGF•A was immobilized, appearance of G418$^r$ colonies was confirmed and the number of the colonies was the same as those of the plates using CH-271, and CH-296. This suggests that a retrovirus binding domain having substantially the same functions as those of CH-271 and CH-296 is present on FGF molecule.

(3) Gene Transfer Using C-FGF-CS1

The effects of C-FGF-CS1 polypeptide on retrovirus infection was investigated according to the following procedures. Namely, NIH/3T3 cell colony assay was carried out according to the same manner as described in Example 8 (1) by using plates prepared with 133 pmol/cm$^2$ of C-FGF-CS1 (6.7 μg/cm$^2$), C-FGF•A (6.3 μg/cm$^2$), CH-271 (8 μg/cm$^2$), and CH-296 (8.4 μg/cm$^2$), respectively, according to the method described in Example 2 (9). The results are shown in FIG. 25. FIG. 25 is a graph illustrating the relation between the functional materials and the gene transfer efficiencies. In FIG. 25, the abscissa indicates the functional materials used and the ordinate indicates the number of G418$^r$ colonies.

As shown in FIG. 25, almost the same number of colonies appear in the plates on which these four polypeptides were immobilized, respectively, indicating that C-FGF-CS1 molecule has the retrovirus binding activity equivalent to the other polypeptides.

(4) Gene Transfer Using C277-ColV

The effects of C277-ColV polypeptide on retrovirus infection was assessed according to the same manner as in Example 8 (1) by using a plate prepared with 124 pmol/cm$^2$ (6.4 μg/cm$^2$) of C277-ColV and a control plate on which BSA was immobilized. The results are shown in FIG. 26. FIG. 26 is a graph illustrating the relation between the functional material and the gene transfer efficiency. The abscissa indicates the functional material used and BSA and the ordinate indicates the number of G418$^r$ colonies.

As shown in FIG. 26, no colony appeared in the control plate coated with BSA. On the other hand, when using C277-ColV immobilized plate, G418$^r$ colonies appeared. This indicates that the retrovirus remains on the plate after washing due to the presence of a retrovirus binding domain on the ColV molecule.

As described hereinabove, the present invention provides a method for efficient gene transfer into target cells with retroviruses. When the method of the present invention is carrying but by selecting a cell binding material suitable for target cells, transformed target cells can be obtained conveniently at the high gene transfer efficiency without any necessity of a special retrovirus vector. By grafting the transformed cells into vertebrate, transformed animal is readily prepared and the present invention is useful in various technical fields such as medical sciences, cell technology, genetic engineering and developmental technology. In addition, there are provided a culture medium containing the functional material of the present invention or a mixture thereof and a reagent kit for carrying out retrovirus mediated gene transfer into target cells. By using these culture medium and kit, localization of a retrovirus, transduction of an exogenous gene into target cells and the like can be readily and efficiently carried out.

BRIEF EXPLANATION OF DRAWINGS

FIG. 1 is a graph illustrating the gene transfer efficiencies into the target cells with the fibroblast growth factor, the functional material containing the fibroblast growth factor and the mixture of the fibroblast growth factor and the cell adhesion domain polypeptide of fibronectin.

FIG. 2 is a graph illustrating the gene transfer efficiencies into the target cells with the fibroblast growth factor, the mixture of the fibroblast growth factor and the cell adhesion domain polypeptide of fibronectin and the cell adhesion domain polypeptide of fibroncetin.

FIG. 3 is a graph illustrating the gene transfer efficiencies into the target cells with the collagen fragment, the mixture of the cell binding domain polypeptide of fibronectin and the collagen fragment, the functional material containing the collagen fragment and the mixture of the cell binding domain polypeptide of fibronectin.

FIG. 4 is a graph illustrating the gene transfer efficiencies into the target cells with the fibronectin fragment and the mixture of the fibronectin fragment and the cell binding domain polypeptide of fibronectin.

FIG. 5 is a graph illustrating the gene transfer efficiencies into the target cells with the cell binding domain polypeptide of fibronectin, the polylysine, the mixture of the polylysine and the cell binding domain polypeptide of fibronectin, the fibronectin fragment and the mixture of the fibronectin fragment and the cell binding domain polypeptide of fibronectin.

Figure 1:
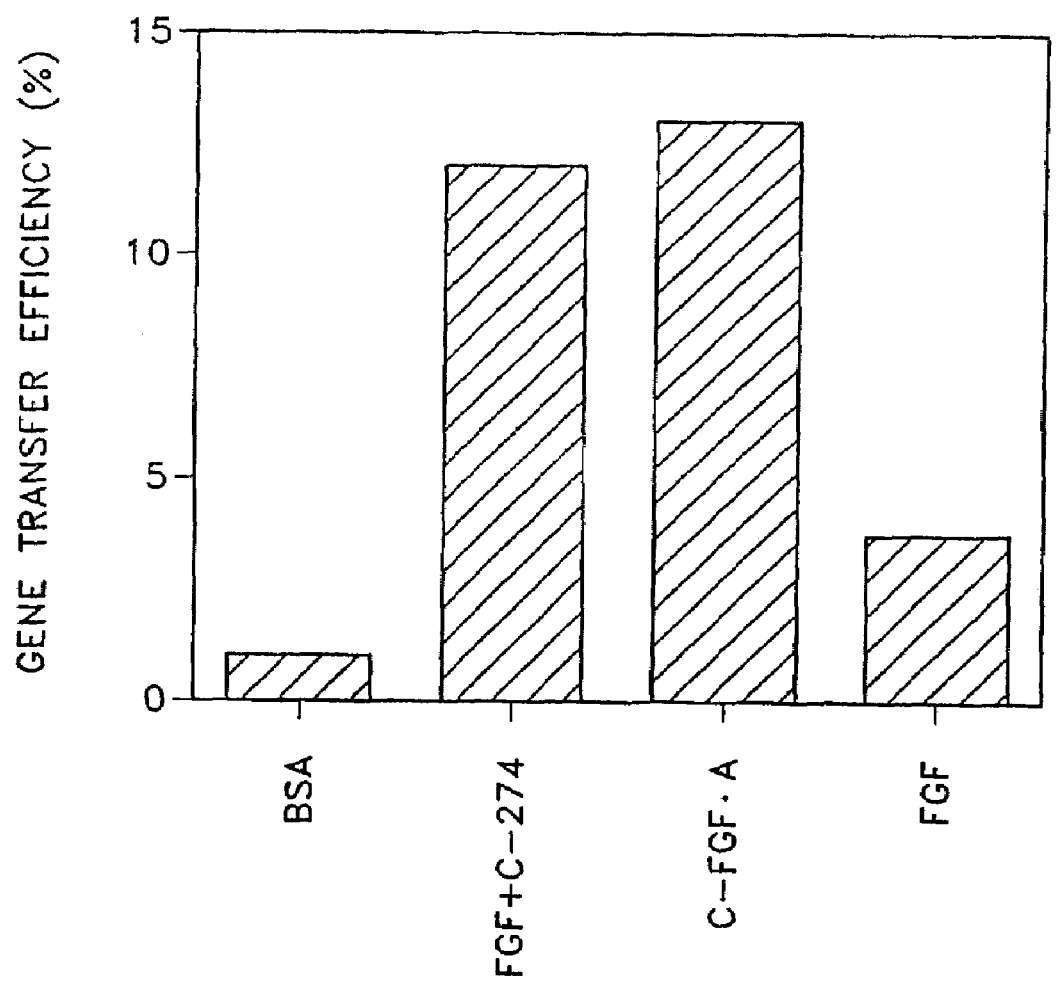
Figure 2:
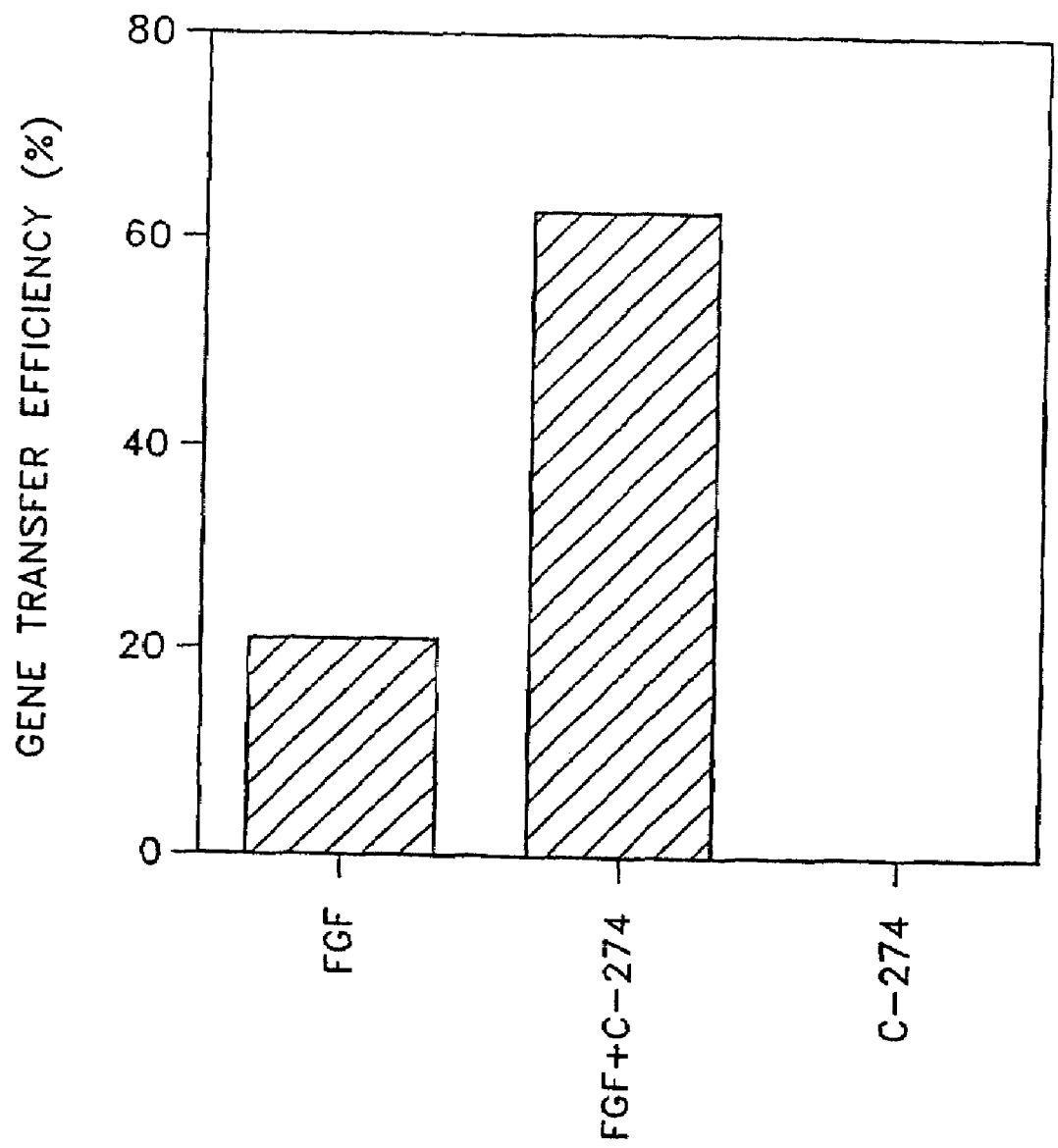
Figure 3:
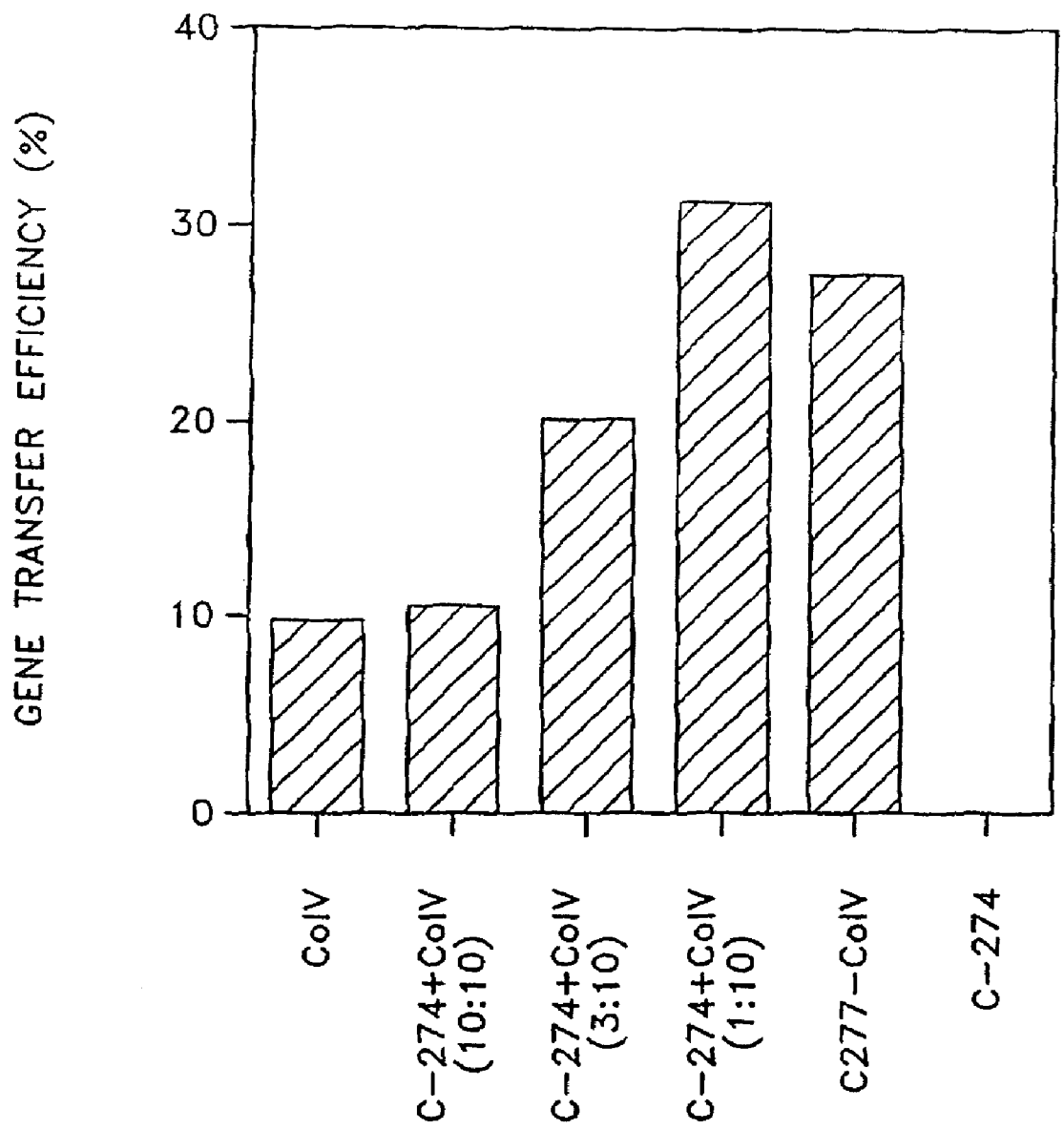
Figure 4:
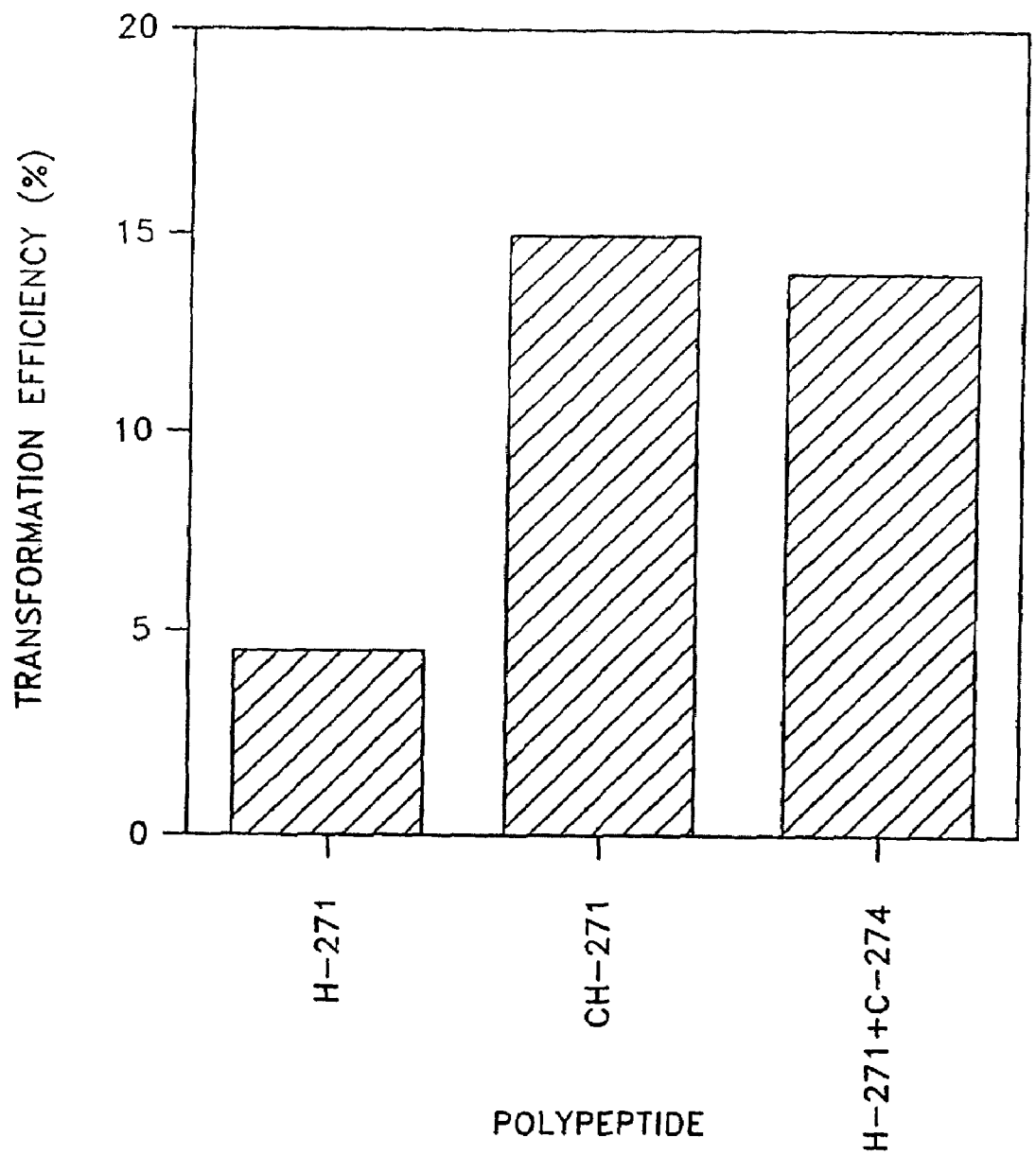
Figure 5:
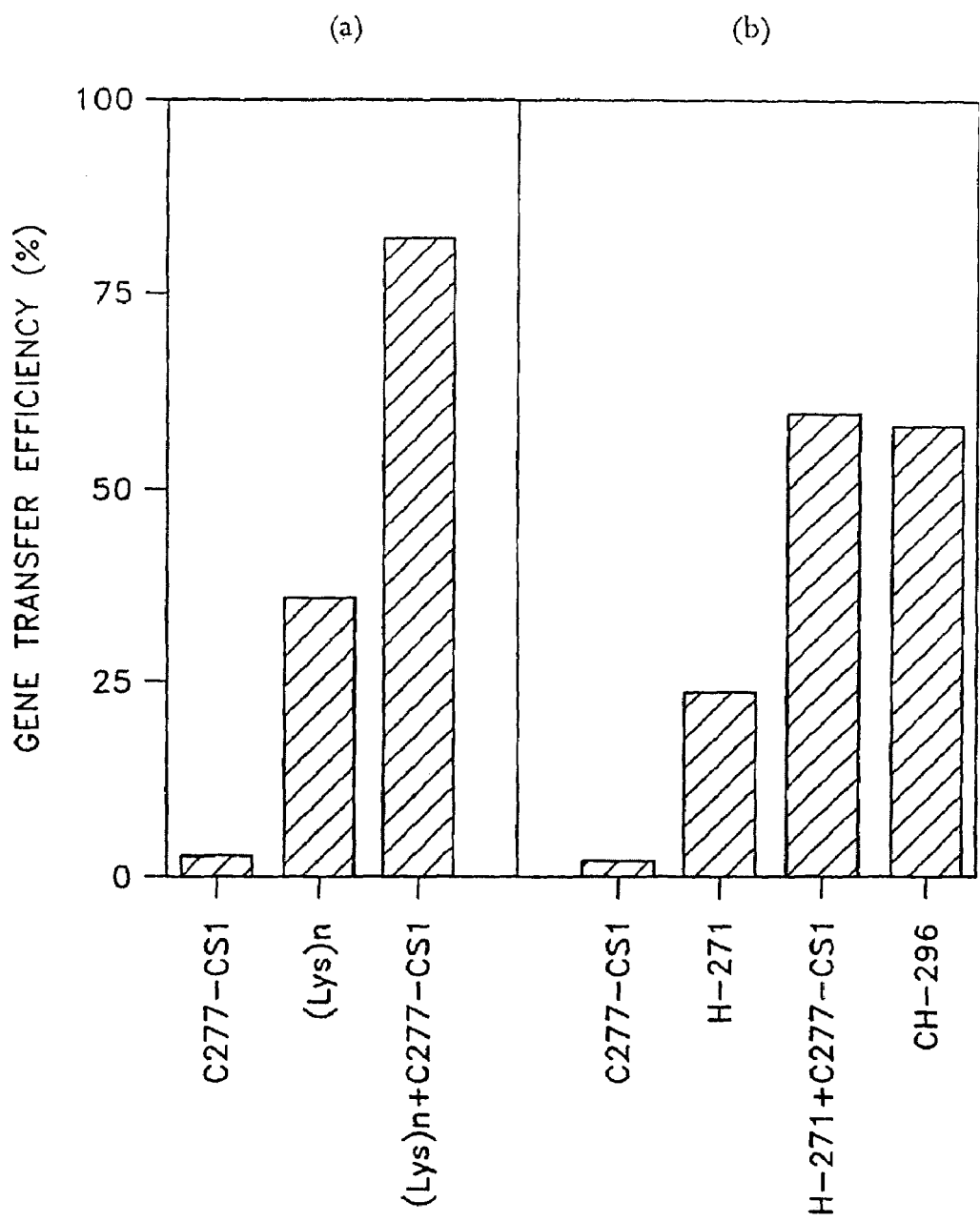
Figure 6:
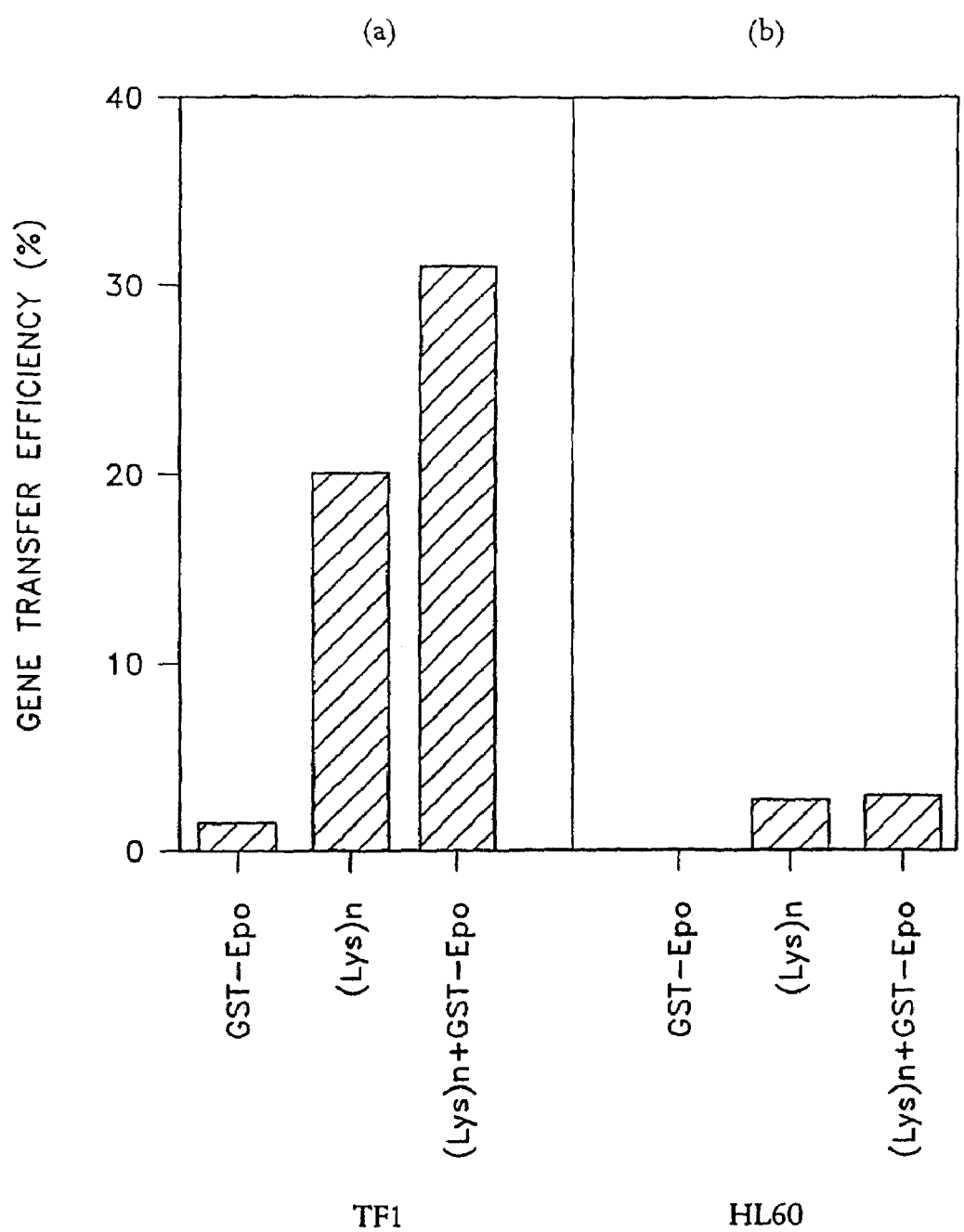
FIG. 6 is a graph illustrating the gene, transfer efficiencies into the target cells with the erythropoietin derivative, the polylysine and the mixture of the erythropoietin derivative and the polylysine.
Figure 7:
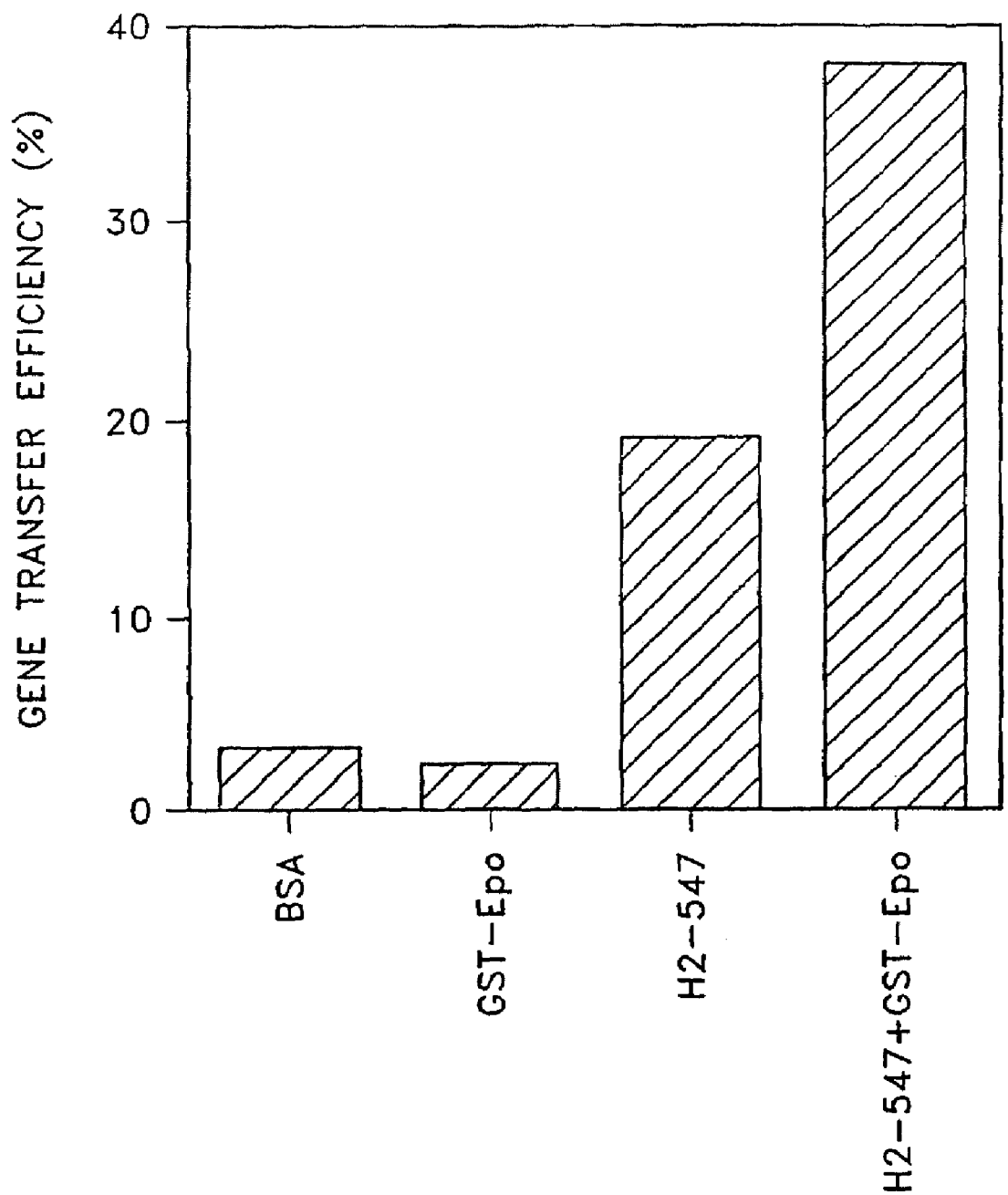
FIG. 7 is a graph illustrating the gene transfer efficiencies into the target cells with the erythropoietin derivative, the fibronectin fragment polymer and the mixture of the erythropoietin derivative and the fibronectin fragment polymer.
Figure 8:
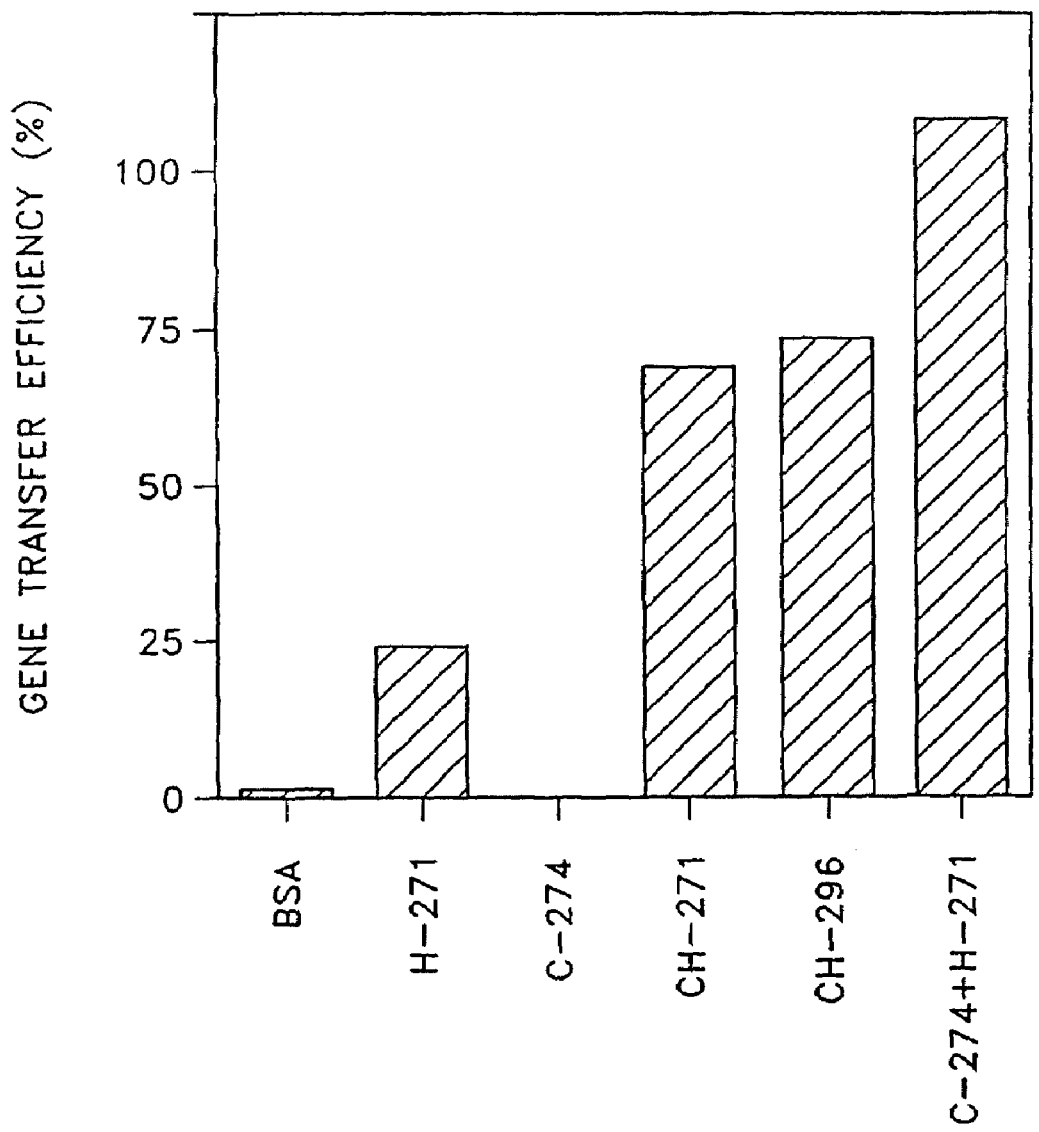
FIG. 8 is a graph illustrating the gene transfer efficiencies into the target cells with the beads on which the fibronectin fragment was immobilized, the beads on which the cell binding domain polypeptide of fibronectin was immobilized and the beads on which the mixture of the fibronectin fragment and the cell binding domain polypeptide of fibronectin was immobilized.
Figure 9:
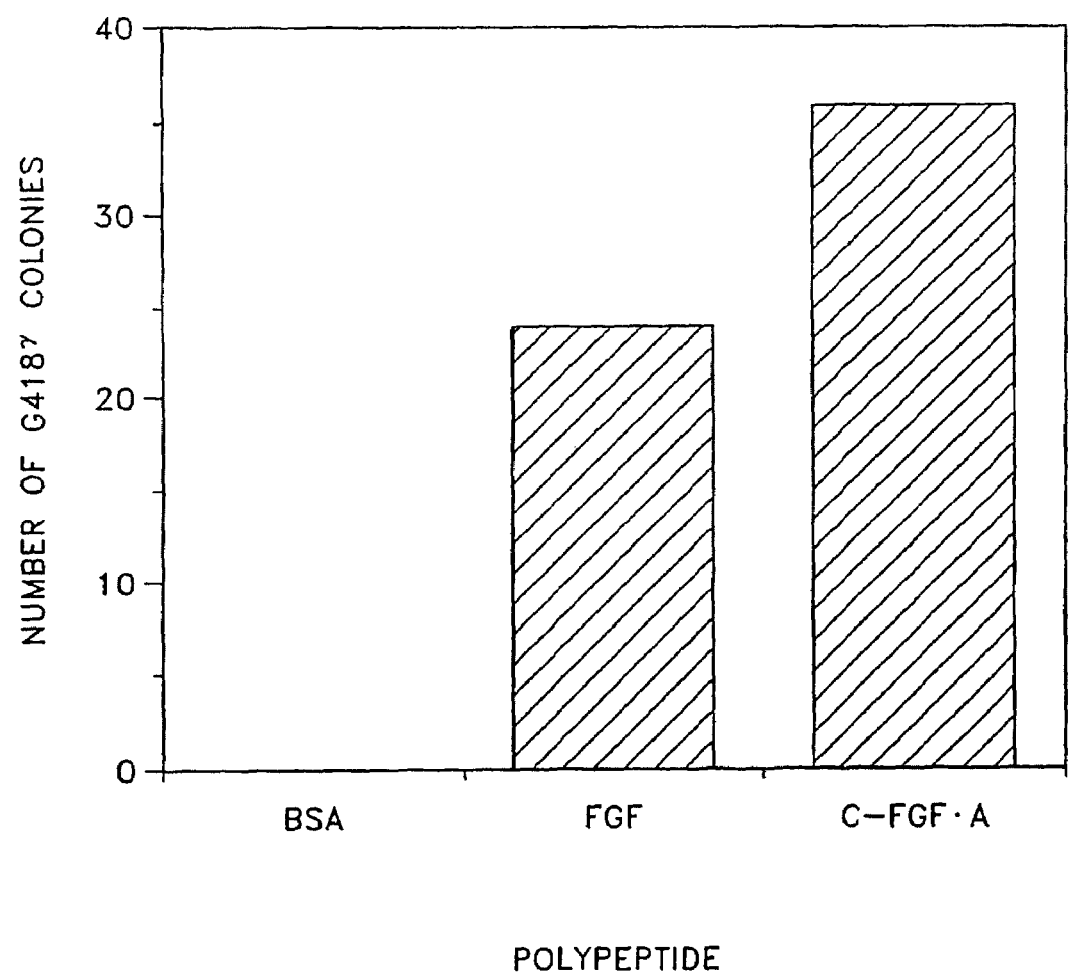
FIG. 9 is a graph illustrating the transformation of the target cells with the fibroblast growth factor and the functional material containing the fibroblast growth factor.
Figure 10:
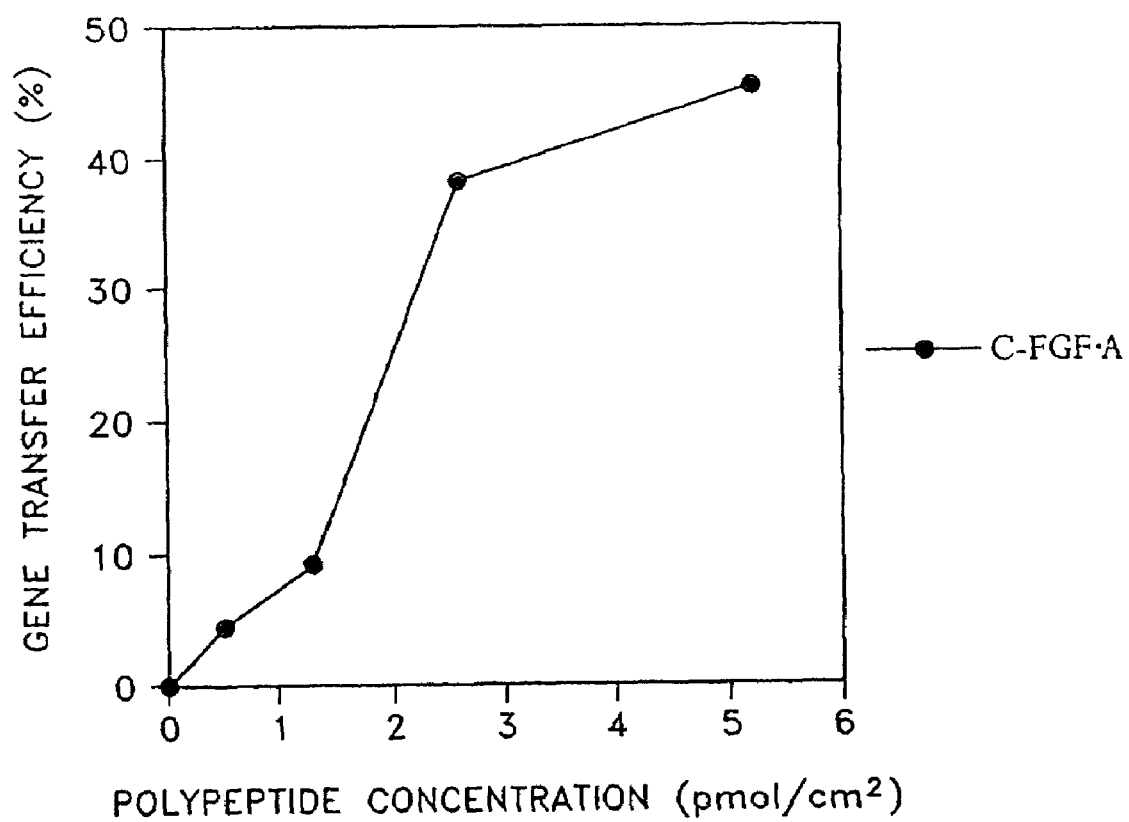
FIG. 10 is a graph illustrating the relation between the amount of the functional material containing the fibroblast growth factor used and the gene transfer efficiency.
Figure 11:
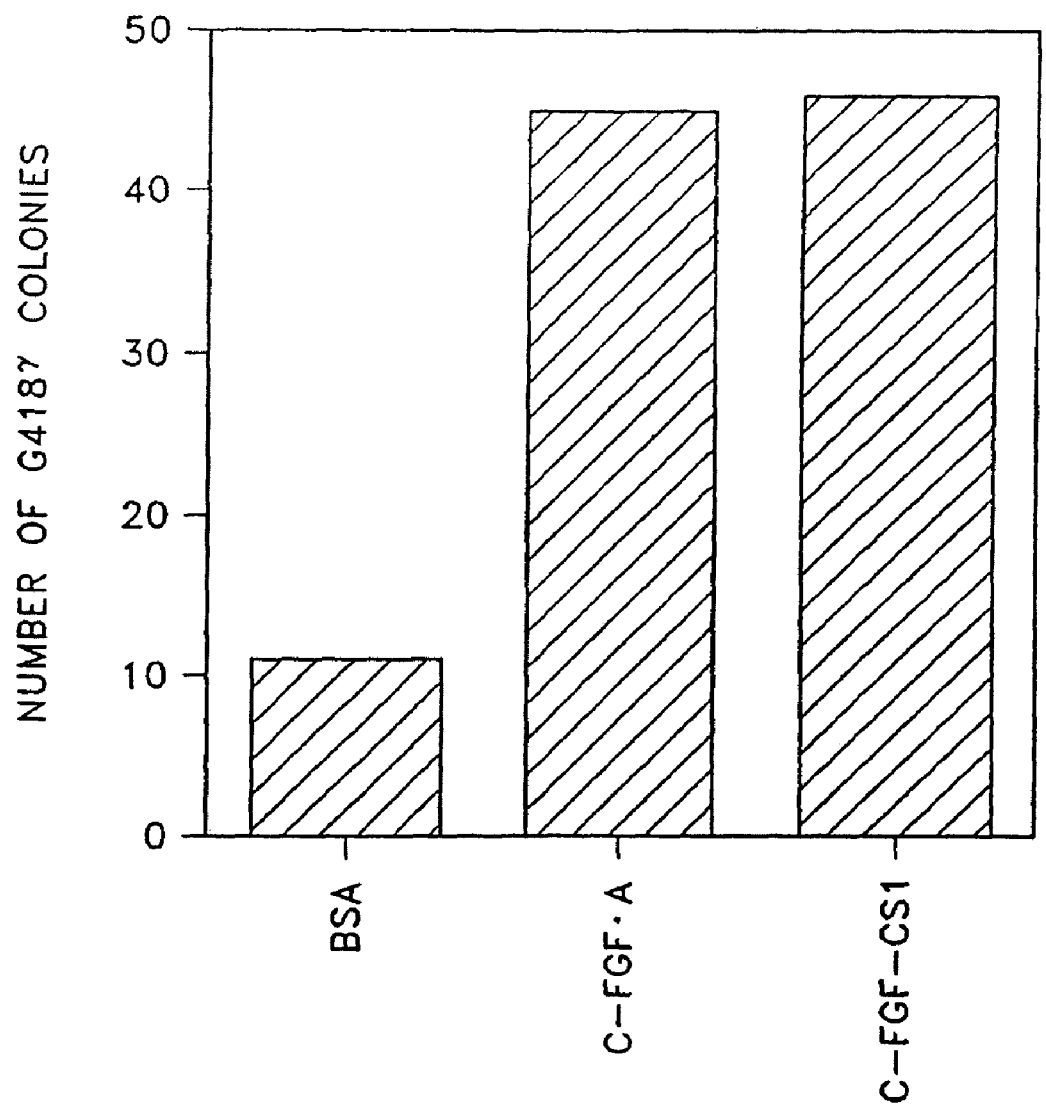
FIG. 11 is a graph illustrating the transformation of the target cells with the functional material containing fibroblast growth factor.
Figure 12:
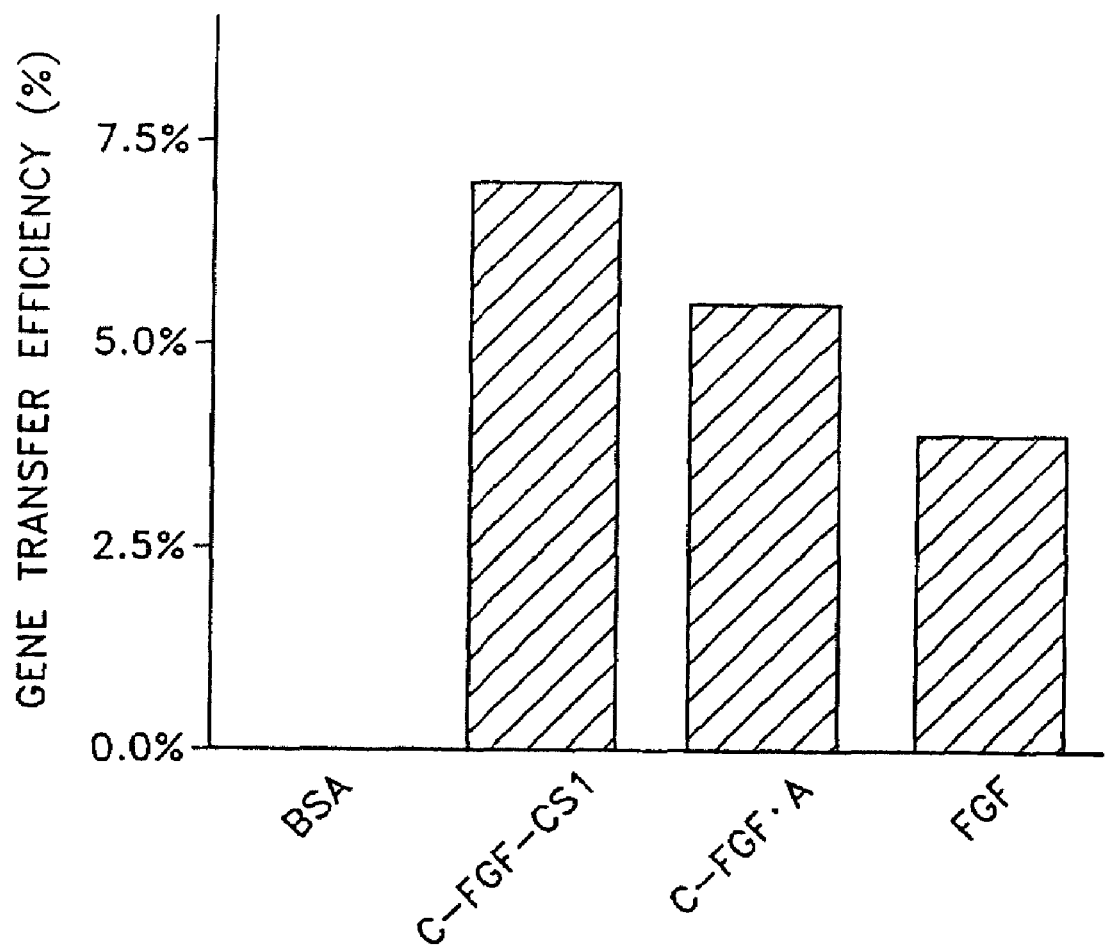
FIG. 12 is another graph illustrating the transformation of the target cells with the functional material containing the fibroblast growth factor.
Figure 13:
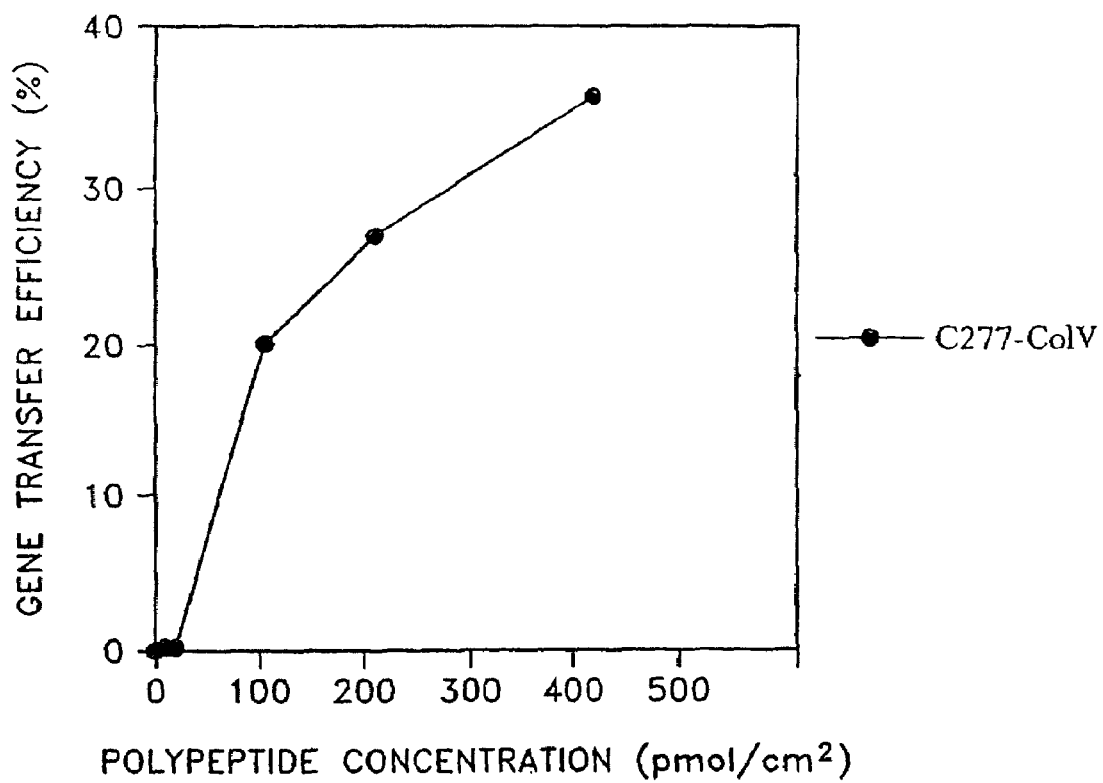
FIG. 13 is a graph illustrating the relation between gene transfer efficiency into the target cells and the amount of the functional material containing the collagen fragment used.
Figure 14:
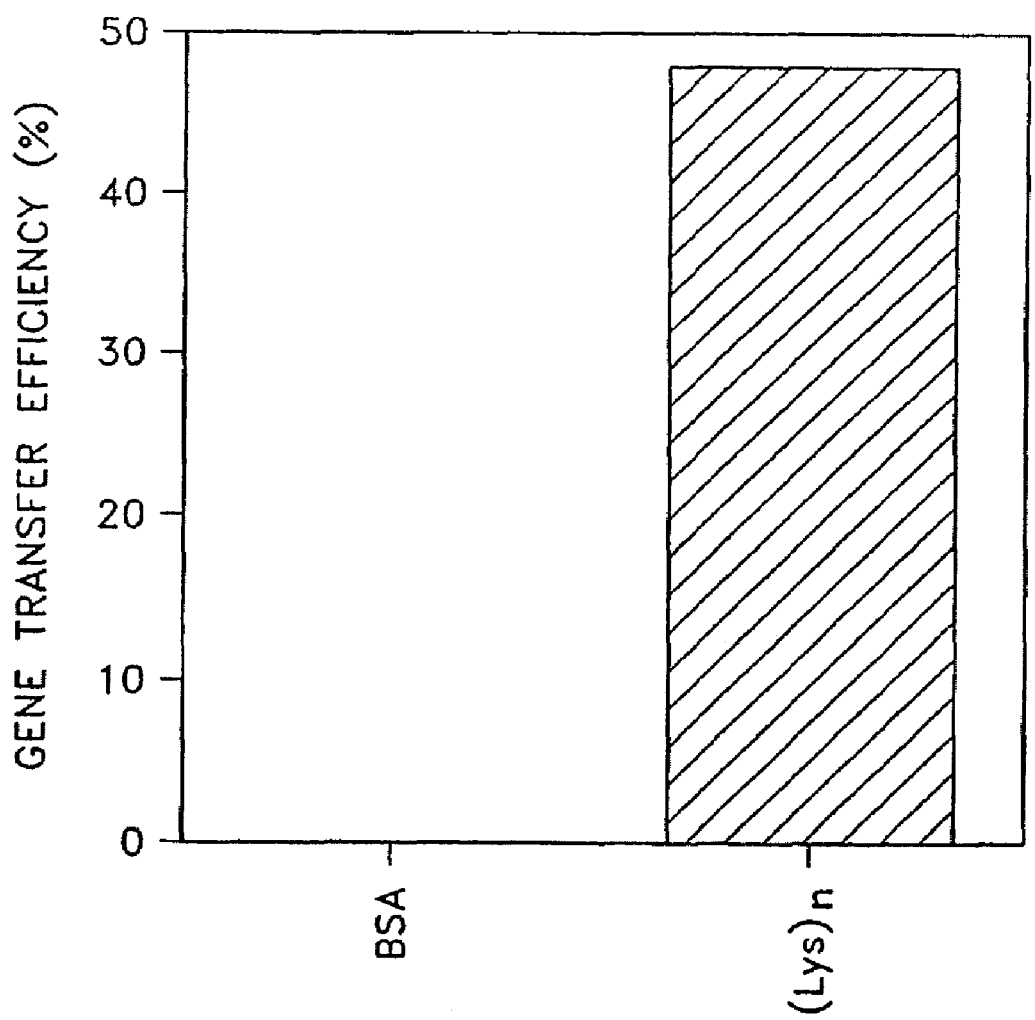
FIG. 14 is a graph illustrating the gene transfer efficiency into the target cells with the polylysine.
Figure 15:
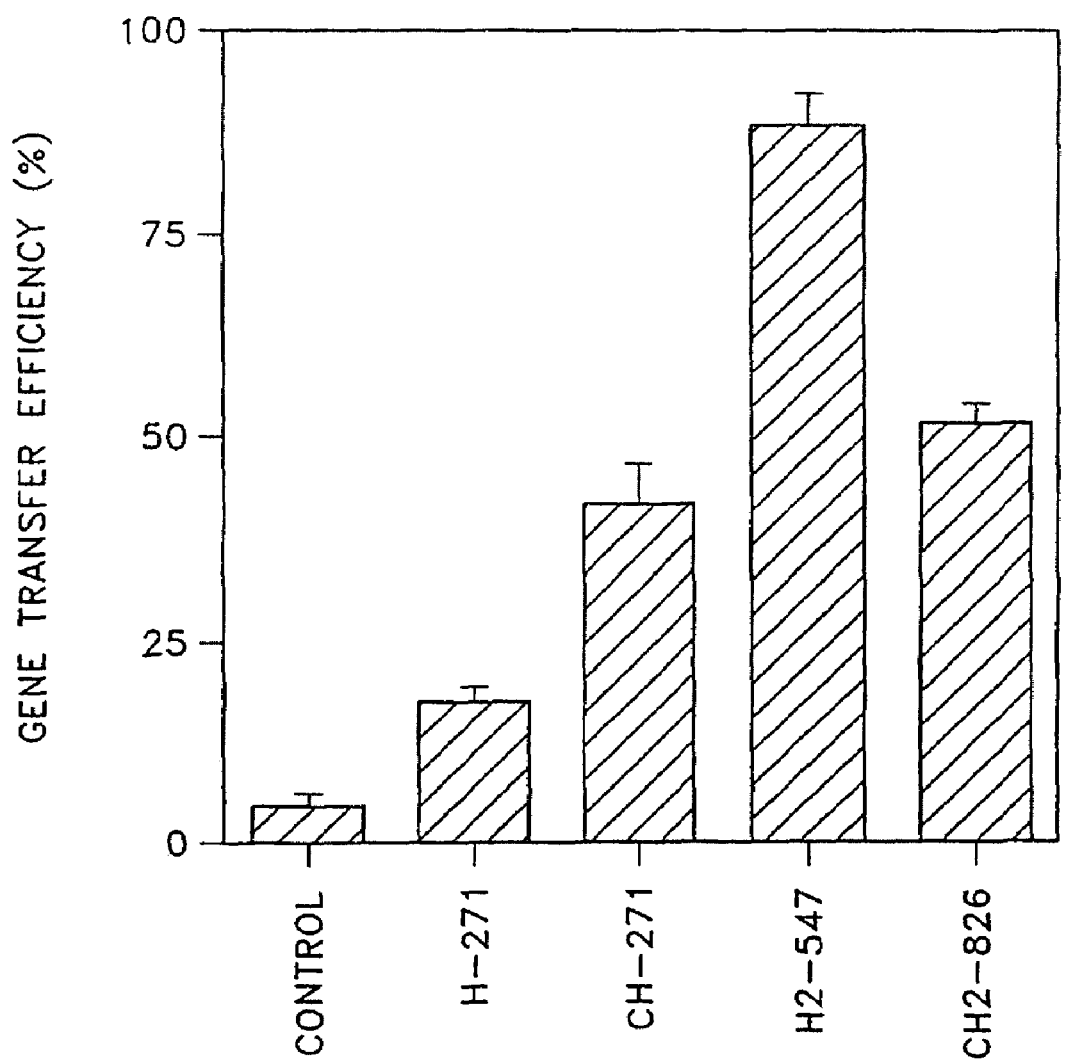
FIG. 15 is a graph illustrating the transformation of the target cells with the fibronectin fragment and the fibronectin fragment polymer.
Figure 16:
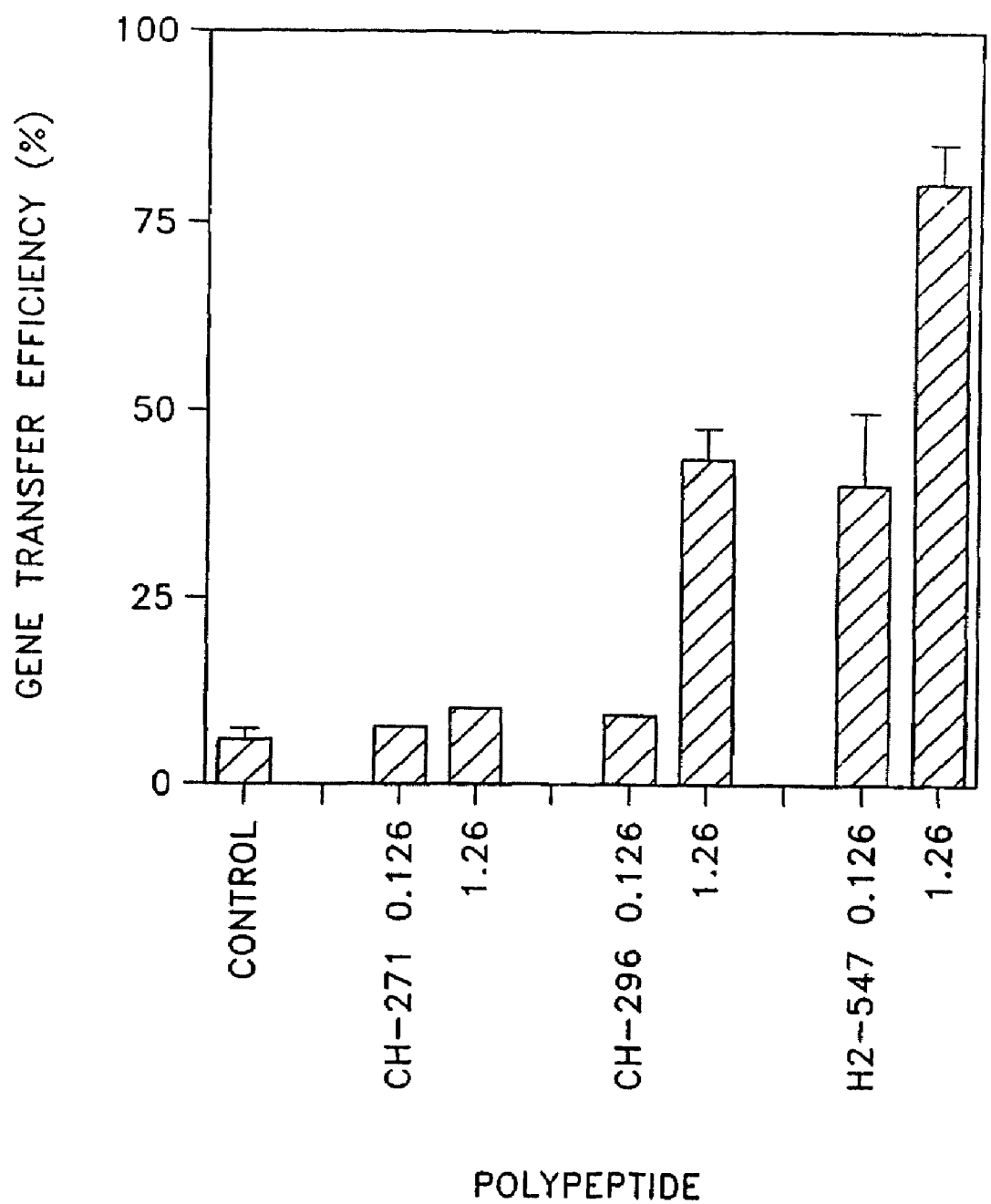
FIG. 16 is another graph illustrating the transformation of target cells with the fibronectin fragment and the fibronectin fragment polymer.
Figure 17:
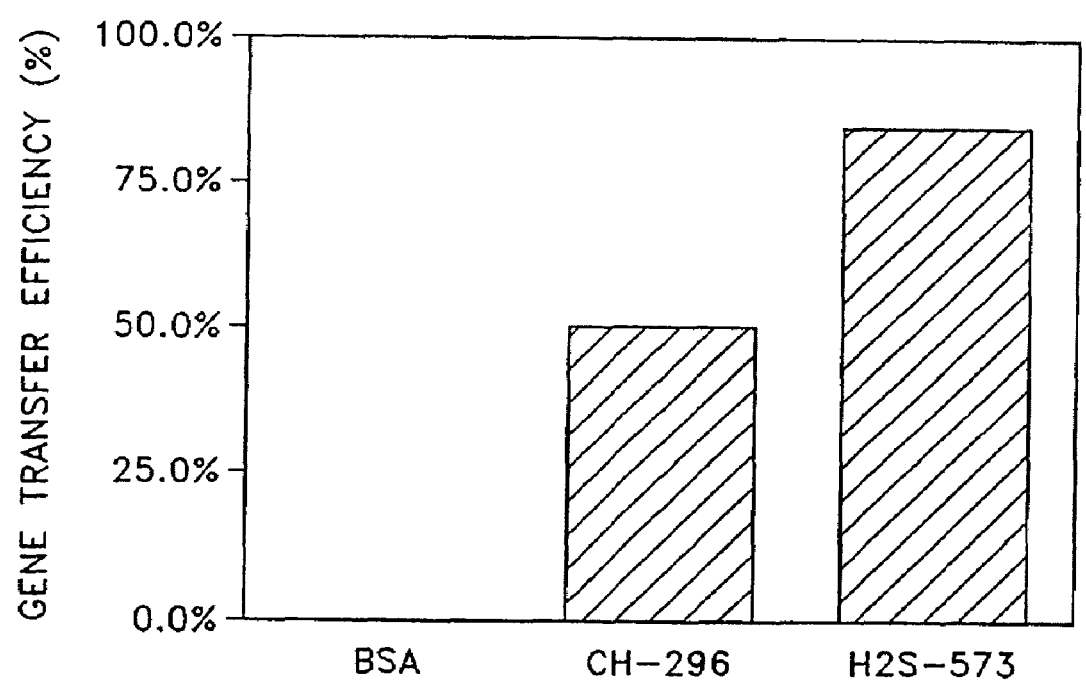
FIG. 17 is yet another graph illustrating the gene transfer efficiency into the target cells with the fibronectin fragment and the fibronectin fragment polymer.
Figure 18:
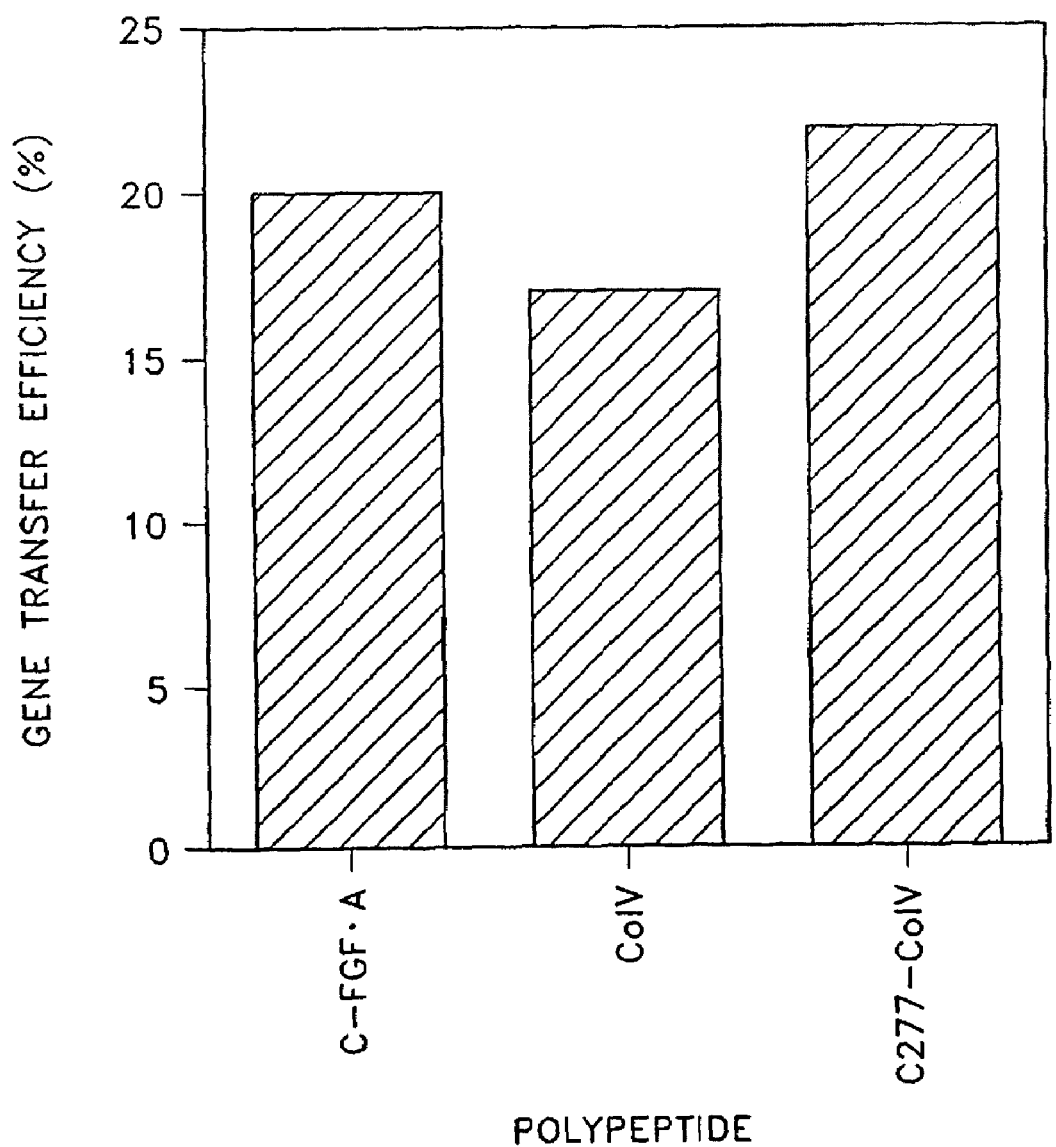
FIG. 18 is a graph illustrating the gene transfer efficiency into the target cells with the functional material containing the fibroblast growth factor, the collagen fragment and the functional material containing the collagen fragment.
Figure 19:
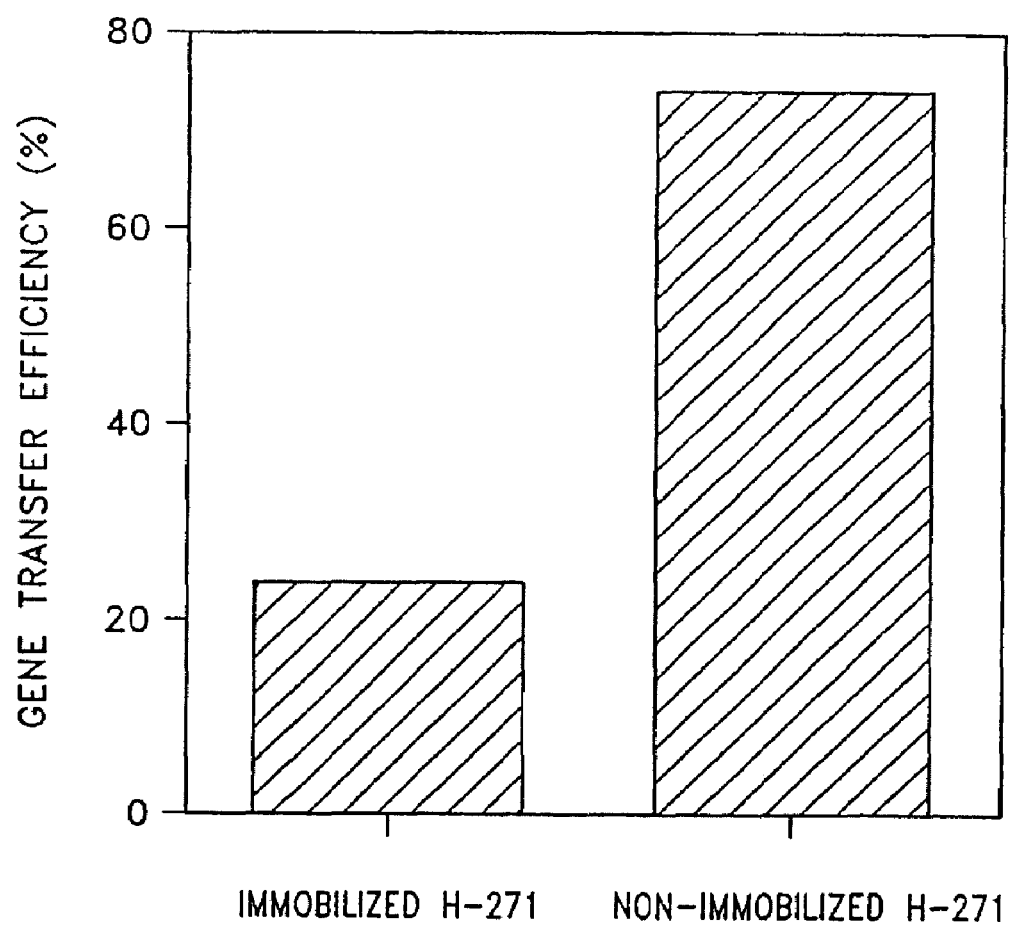
FIG. 19 is a graph illustrating the gene transfer efficiency into the target cells with the fibronectin fragment.
Figure 20:
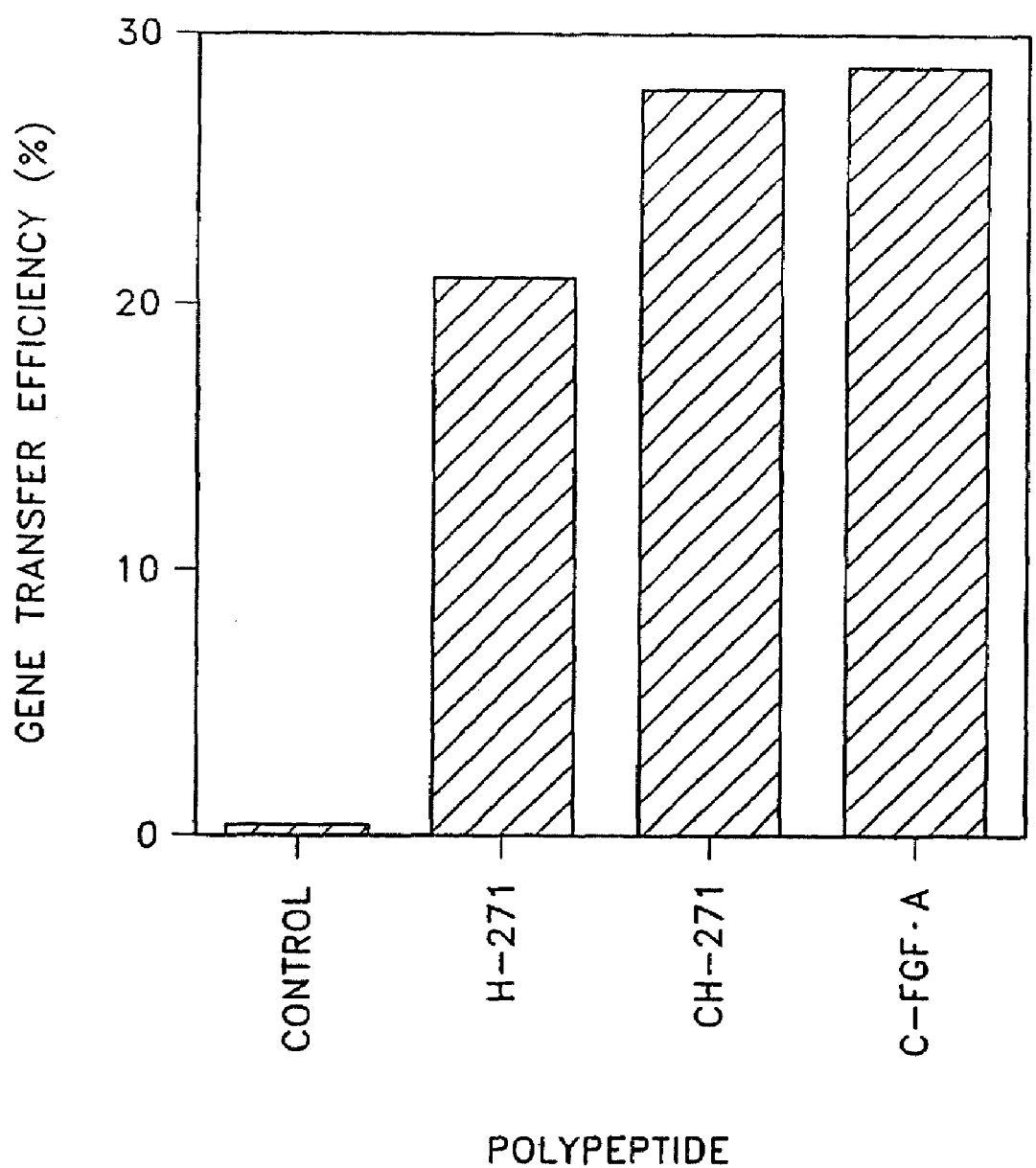
FIG. 20 is a graph illustrating the gene transfer efficiency into the target cells with the functional material containing the fibronectin fragment and fibroblast growth factor.
Figure 21:
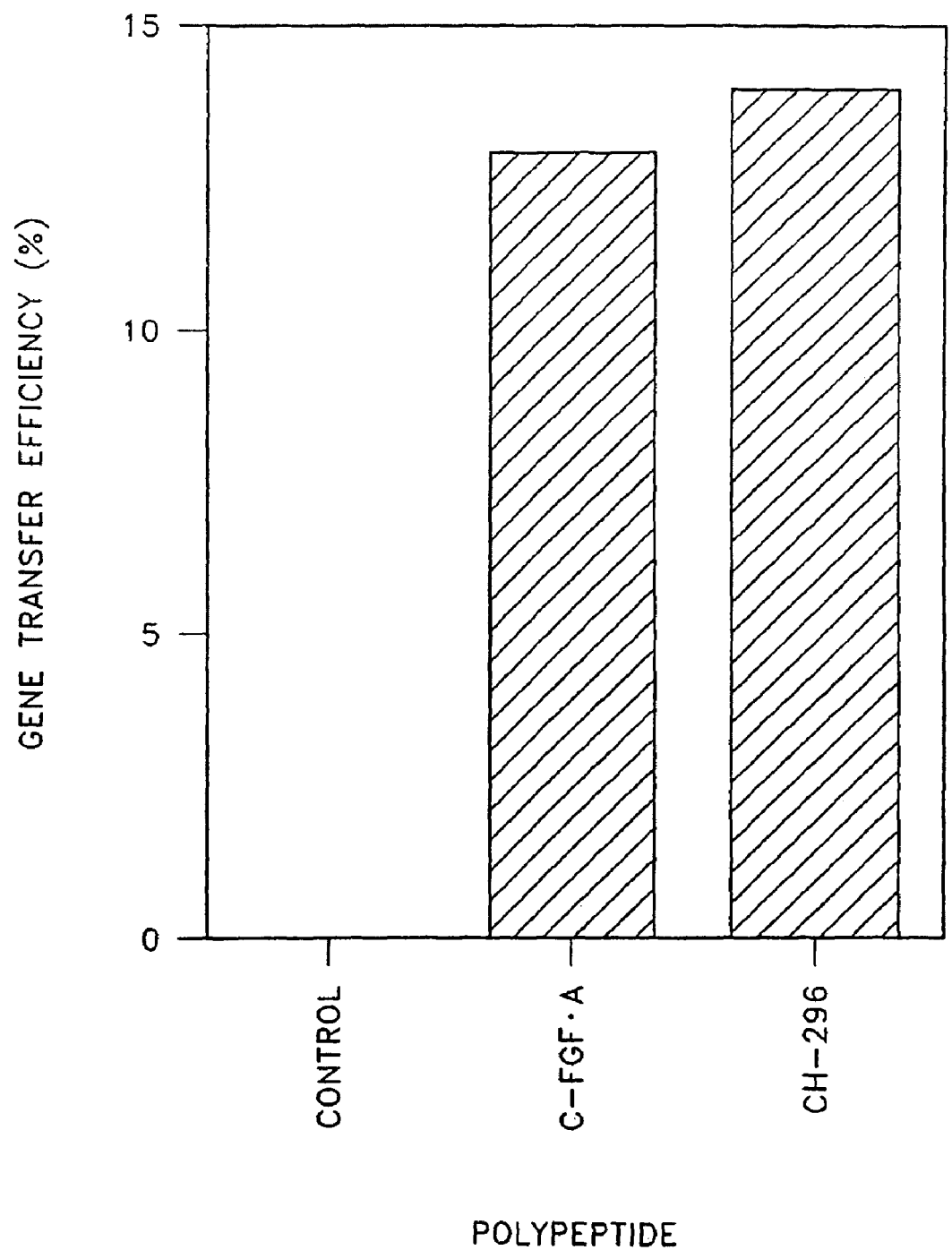
FIG. 21 is a graph illustrating the gene transfer efficiency into the target cells with the functional material containing the fibroblast growth factor and the fibronectin fragment.
Figure 22:
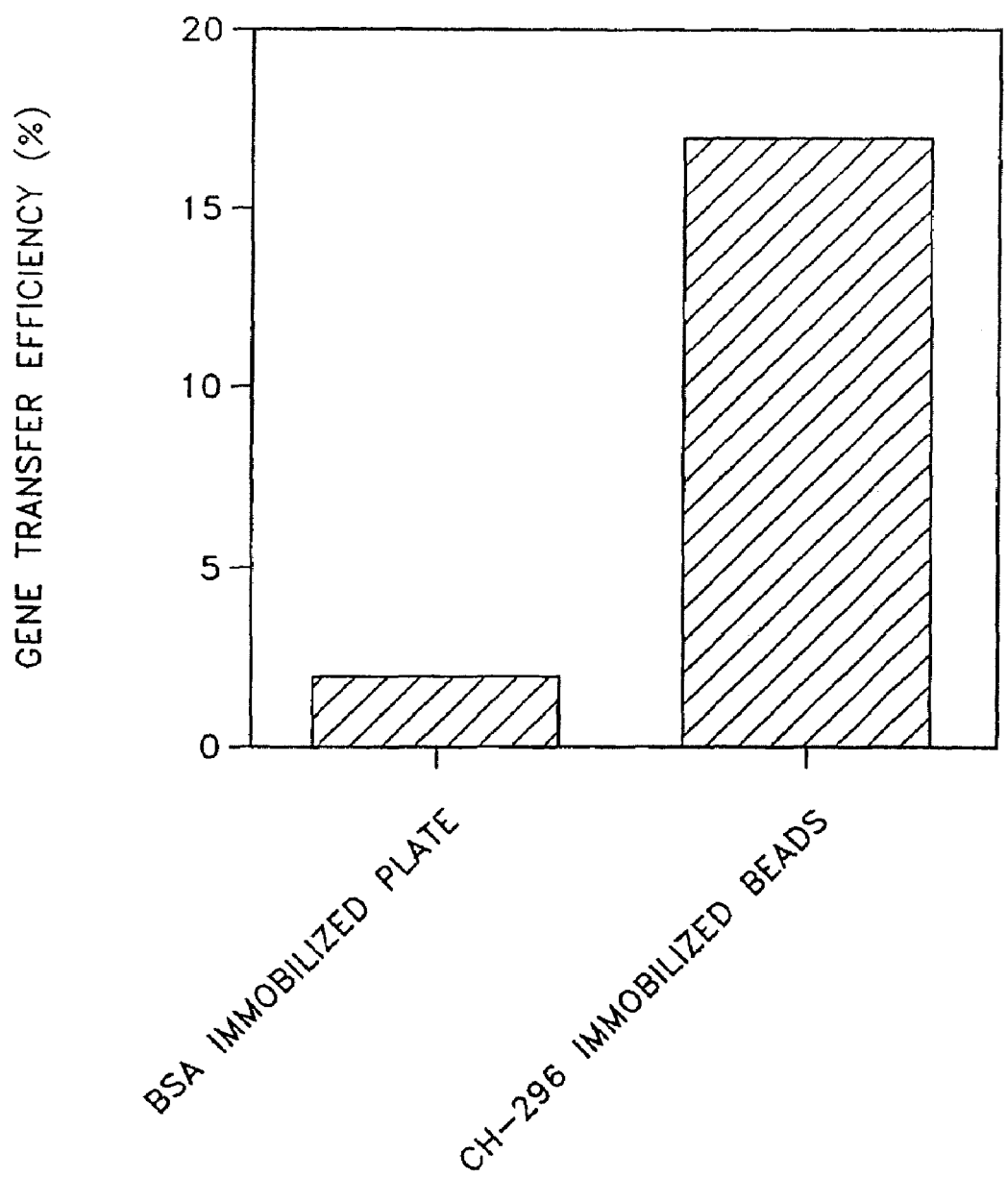
FIG. 22 is a graph illustrating the gene transfer efficiency into the target cells with the fibronectin fragment immobilized beads.
Figure 23:
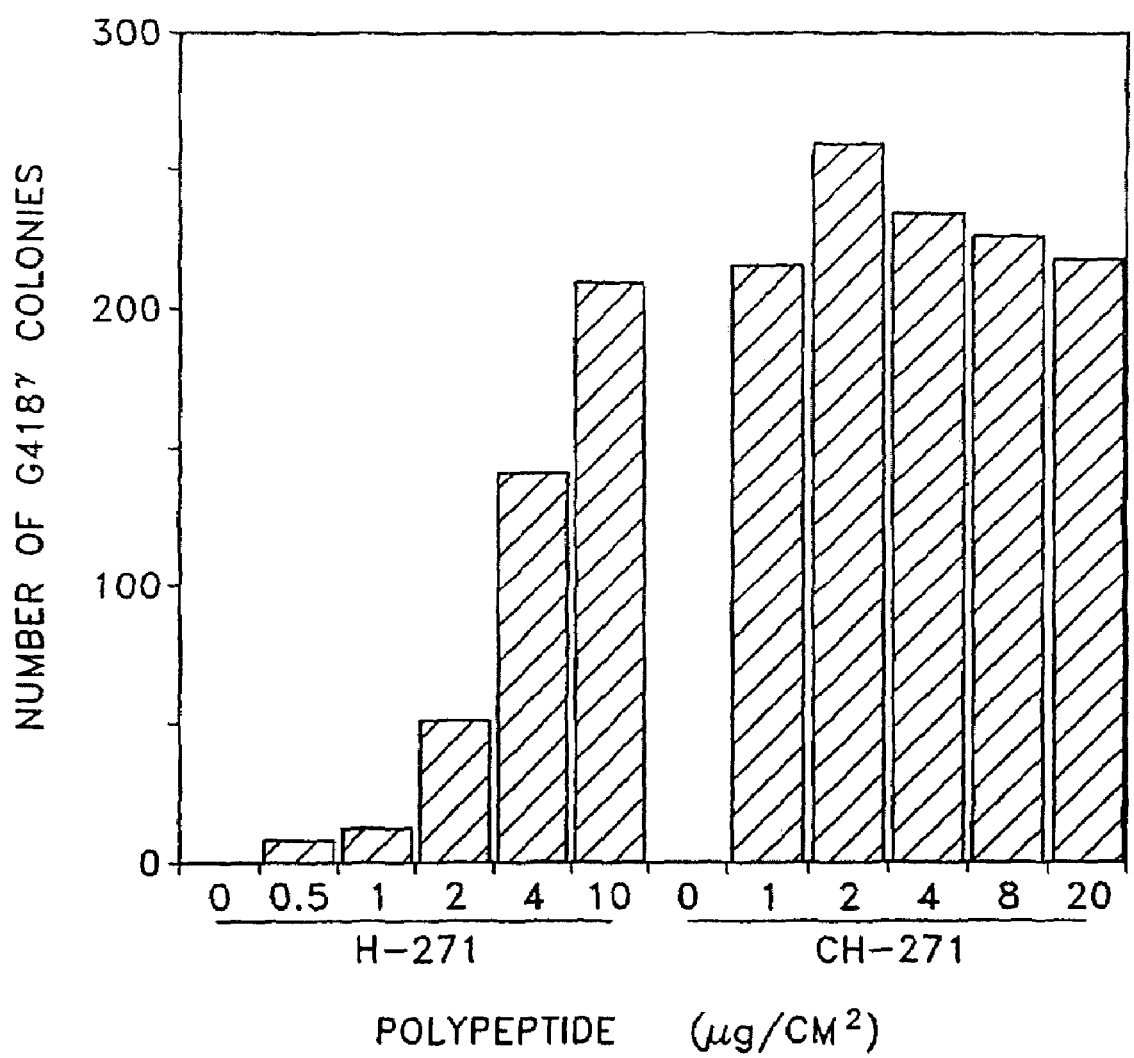
FIG. 23 is a graph illustrating the relation between the amount of the fibronectin fragment used and the gene transduction of the target cells.
Figure 24:
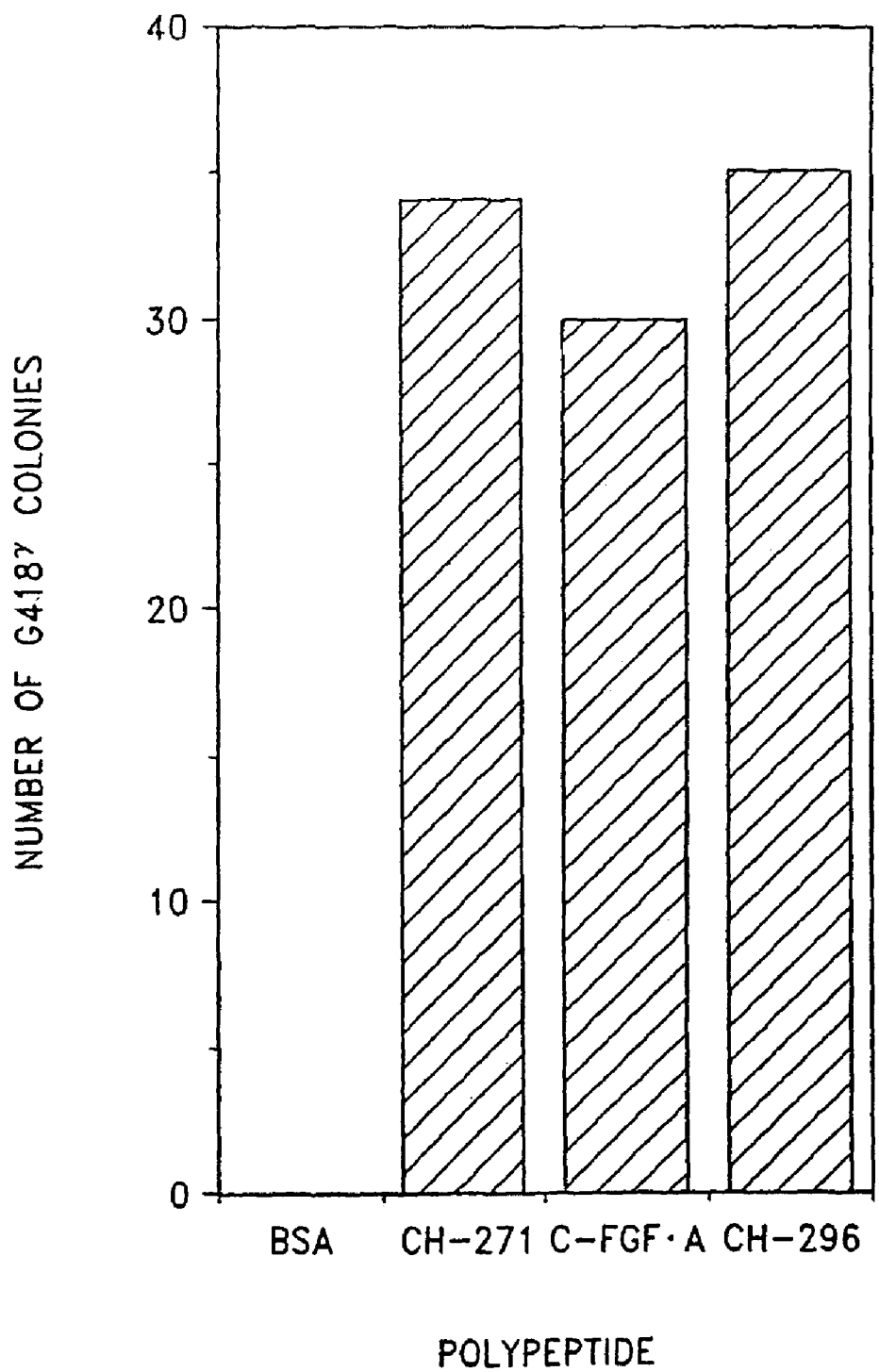
FIG. 24 is a graph illustrating the gene transduction of the target cells with the functional material containing the fibroblast growth factor and the fibronectin fragment.
Figure 25:
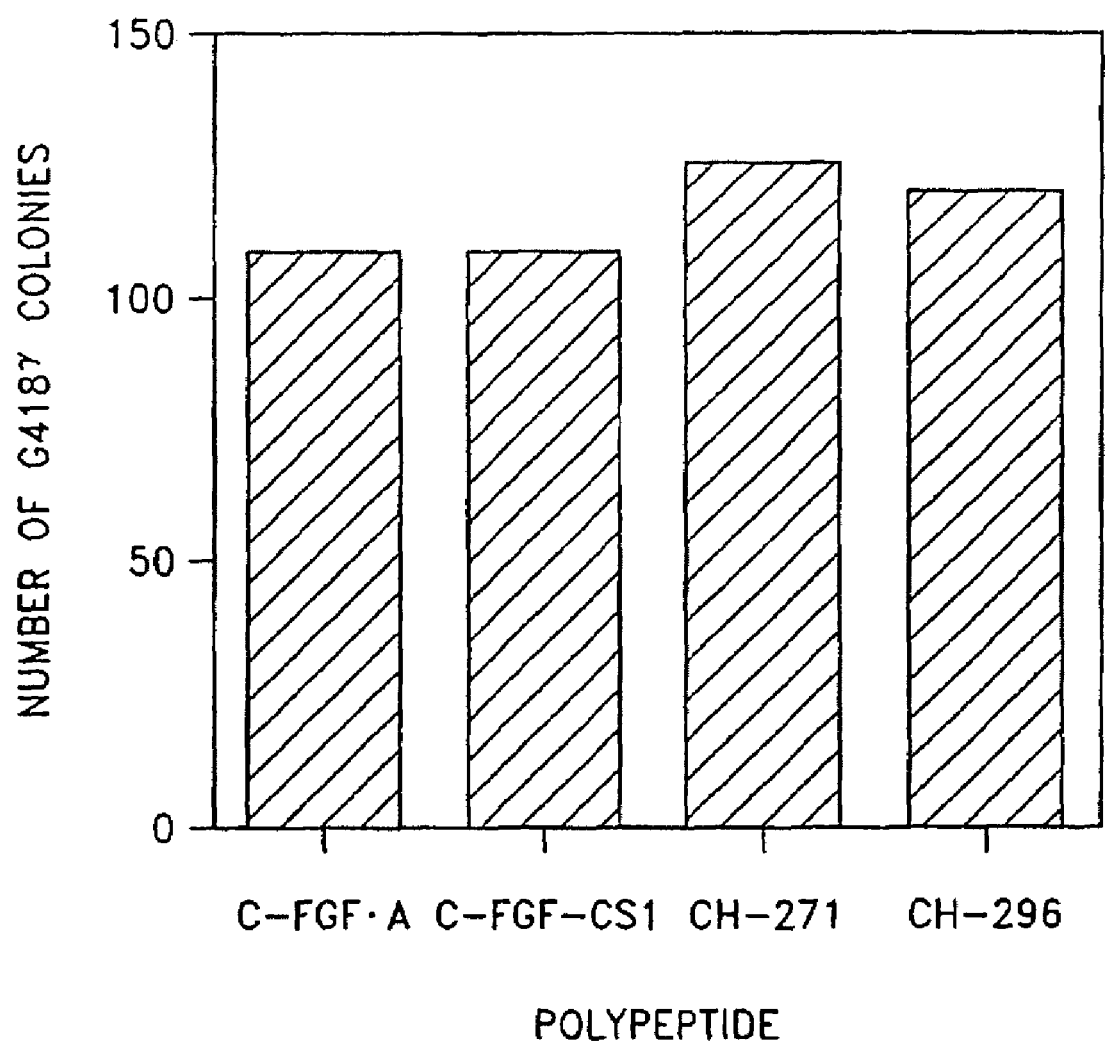
FIG. 25 is another graph illustrating the gene transduction of the target cells with the functional material containing the fibroblast growth factor and the fibronectin fragment.
Figure 26:
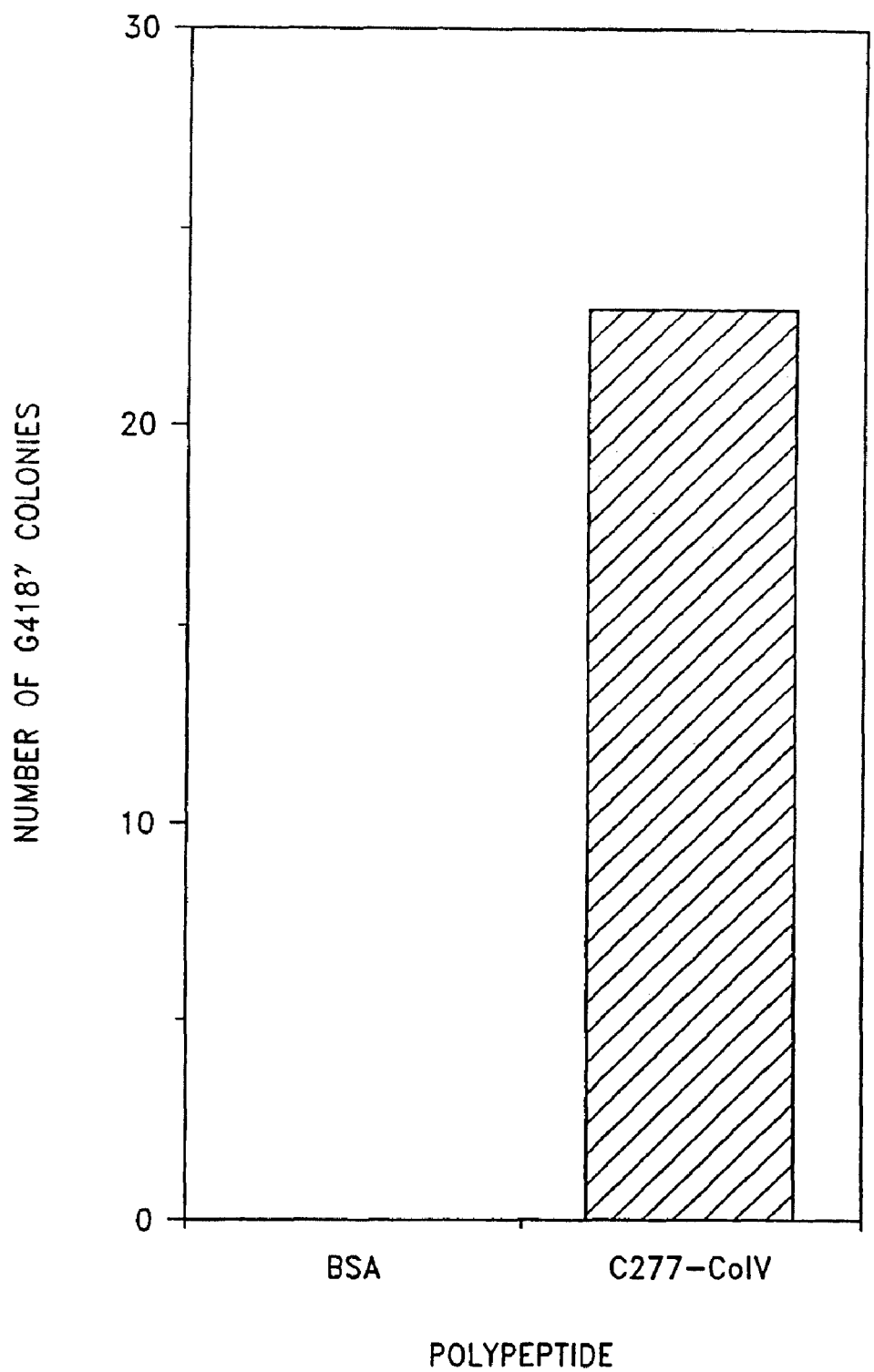
FIG. 26 is a graph illustrating the gene transduction of the target cells with the functional material containing the collagen fragment.

The invention claimed is:

1. An isolated polypeptide comprising the amino acid sequence shown in SEQ. ID No. 13.

2. An isolated nucleic acid comprising a nucleic acid sequence encoding the polypeptide of claim 1.

3. The isolated nucleic acid of claim 2 comprising the nucleic acid sequence shown in SEQ. ID No. 17.

* * * * *

SEQUENCE LISTING (1) GENERAL INFORMATION:

(iii) NUMBER OF SEQUENCES: 39

(2) INFORMATION FOR SEQ ID NO: 1:

(i) SEQUENCE CHARACTERISTICS:
      (A) LENGTH: 271 amino acids
      (B) TYPE: amino acid
      (C) STRANDEDNESS: <Unknown>
      (D) TOPOLOGY: linear (ii) MOLECULE TYPE: peptide (xi) SEQUENCE DESCRIPTION: SEQ ID NO: 1:

Ala Ile Pro Ala Pro Thr Asp Leu Lys Phe Thr Gln Val Thr Pro Thr
 1               5                  10                  15

Ser Leu Ser Ala Gln Trp Thr Pro Pro Asn Val Gln Leu Thr Gly Tyr
                20                  25                  30

Arg Val Arg Val Thr Pro Lys Glu Lys Thr Gly Pro Met Lys Glu Ile
            35                  40                  45

Asn Leu Ala Pro Asp Ser Ser Val Val Ser Gly Leu Met Val
    50                  55                  60

Ala Thr Lys Tyr Glu Val Ser Val Tyr Ala Leu Lys Asp Thr Leu Thr

-continued

```
                65                  70                  75                  80
Ser Arg Pro Ala Gln Gly Val Val Thr Thr Leu Glu Asn Val Ser Pro
                    85                  90                  95

Pro Arg Arg Ala Arg Val Thr Asp Ala Thr Glu Thr Thr Ile Thr Ile
                100                 105                 110

Ser Trp Arg Thr Lys Thr Glu Thr Ile Thr Gly Phe Gln Val Asp Ala
                115                 120                 125

Val Pro Ala Asn Gly Gln Thr Pro Ile Gln Arg Thr Ile Lys Pro Asp
                130                 135                 140

Val Arg Ser Tyr Thr Ile Thr Gly Leu Gln Pro Gly Thr Asp Tyr Lys
145                 150                 155                 160

Ile Tyr Leu Tyr Thr Leu Asn Asp Asn Ala Arg Ser Ser Pro Val Val
                165                 170                 175

Ile Asp Ala Ser Thr Ala Ile Asp Ala Pro Ser Asn Leu Arg Phe Leu
                180                 185                 190

Ala Thr Thr Pro Asn Ser Leu Leu Val Ser Trp Gln Pro Pro Arg Ala
                195                 200                 205

Arg Ile Thr Gly Tyr Ile Ile Lys Tyr Glu Lys Pro Gly Ser Pro Pro
                210                 215                 220

Arg Glu Val Val Pro Arg Pro Arg Pro Gly Val Thr Glu Ala Thr Ile
225                 230                 235                 240

Thr Gly Leu Glu Pro Gly Thr Glu Tyr Thr Ile Tyr Val Ile Ala Leu
                245                 250                 255

Lys Asn Asn Gln Lys Ser Glu Pro Leu Ile Gly Arg Lys Lys Thr
                260                 265                 270

(2) INFORMATION FOR SEQ ID NO: 2:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 2:

Asp Glu Leu Pro Gln Leu Val Thr Leu Pro His Pro Asn Leu His Gly
1               5                   10                  15

Pro Glu Ile Leu Asp Val Pro Ser Thr
                20                  25

(2) INFORMATION FOR SEQ ID NO: 3:

(i) SEQUENCE CHARACTERISTICS:
        (A) LENGTH: 155 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 3:

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
                20                  25                  30

Tyr Cys Lys Asn Gly Gly Phe Phe Leu Arg Ile His Pro Asp Gly Arg
                35                  40                  45
```

```
Val Asp Gly Val Arg Glu Lys Ser Asp Pro His Ile Lys Leu Gln Leu
 50                  55                  60

Gln Ala Glu Glu Arg Gly Val Val Ser Ile Lys Gly Val Cys Ala Asn
 65                  70                  75                  80

Arg Tyr Leu Ala Met Lys Glu Asp Gly Arg Leu Leu Ala Ser Lys Cys
                 85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
130                 135                 140

Ala Ile Leu Phe Leu Pro Met Ser Ala Lys Ser
145                 150                 155
```

(2) INFORMATION FOR SEQ ID NO: 4:

(i) SEQUENCE CHARACTERISTICS:
        (A) LENGTH: 432 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 4:

```
Pro Thr Asp Leu Arg Phe Thr Asn Ile Gly Pro Asp Thr Met Arg Val
 1               5                  10                  15

Thr Trp Ala Pro Pro Ser Ile Asp Leu Thr Asn Phe Leu Val Arg
                 20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
 50                  55                  60

Tyr Val Val Ser Val Ser Ser Val Tyr Glu Gln His Glu Ser Thr Pro
 65                  70                  75                  80

Leu Arg Gly Arg Gln Lys Thr Gly Leu Asp Ser Pro Thr Gly Ile Asp
                 85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
            210                 215                 220

Phe Thr Val Pro Gly Ser Lys Ser Thr Ala Thr Ile Ser Gly Leu Lys
225                 230                 235                 240
```

```
Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
                260                 265                 270

Ile Asp Lys Pro Ser Met Ala Ala Gly Ser Ile Thr Thr Leu Pro Ala
                275                 280                 285

Leu Pro Glu Asp Gly Gly Ser Gly Ala Phe Pro Pro Gly His Phe Lys
                290                 295                 300

Asp Pro Lys Arg Leu Tyr Cys Lys Asn Gly Gly Phe Phe Leu Arg Ile
305                 310                 315                 320

His Pro Asp Gly Arg Val Asp Gly Val Arg Glu Lys Ser Asp Pro His
                325                 330                 335

Ile Lys Leu Gln Leu Gln Ala Glu Glu Arg Gly Val Val Ser Ile Lys
                340                 345                 350

Gly Val Cys Ala Asn Arg Tyr Leu Ala Met Lys Glu Asp Gly Arg Leu
                355                 360                 365

Leu Ala Ser Lys Cys Val Thr Asp Glu Cys Phe Phe Phe Glu Arg Leu
                370                 375                 380

Glu Ser Asn Asn Tyr Asn Thr Tyr Arg Ser Arg Lys Tyr Thr Ser Trp
385                 390                 395                 400

Tyr Val Ala Leu Lys Arg Thr Gly Gln Tyr Lys Leu Gly Ser Lys Thr
                405                 410                 415

Gly Pro Gly Gln Lys Ala Ile Leu Phe Leu Pro Met Ser Ala Lys Ser
                420                 425                 430

(2) INFORMATION FOR SEQ ID NO: 5:

(i) SEQUENCE CHARACTERISTICS:
        (A) LENGTH: 457 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 5:

Pro Thr Asp Leu Arg Phe Thr Asn Ile Gly Pro Asp Thr Met Arg Val
1               5                   10                  15

Thr Trp Ala Pro Pro Pro Ser Ile Asp Leu Thr Asn Phe Leu Val Arg
                20                  25                  30

Tyr Ser Pro Val Lys Asn Glu Glu Asp Val Ala Glu Leu Ser Ile Ser
                35                  40                  45

Pro Ser Asp Asn Ala Val Val Leu Thr Asn Leu Leu Pro Gly Thr Glu
50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
                100                 105                 110

Arg Ala Thr Ile Thr Gly Tyr Arg Ile Arg His His Pro Glu His Phe
                115                 120                 125

Ser Gly Arg Pro Arg Glu Asp Arg Val Pro His Ser Arg Asn Ser Ile
                130                 135                 140

Thr Leu Thr Asn Leu Thr Pro Gly Thr Glu Tyr Val Val Ser Ile Val
145                 150                 155                 160
```

-continued

```
Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Ala Ala Gly Ser Ile Thr Thr Leu Pro Ala
        275                 280                 285

Leu Pro Glu Asp Gly Gly Ser Gly Ala Phe Pro Pro Gly His Phe Lys
    290                 295                 300

Asp Pro Lys Arg Leu Tyr Cys Lys Asn Gly Gly Phe Phe Leu Arg Ile
305                 310                 315                 320

His Pro Asp Gly Arg Val Asp Gly Val Arg Glu Lys Ser Asp Pro His
                325                 330                 335

Ile Lys Leu Gln Leu Gln Ala Glu Glu Arg Gly Val Val Ser Ile Lys
            340                 345                 350

Gly Val Cys Ala Asn Arg Tyr Leu Ala Met Lys Glu Asp Gly Arg Leu
        355                 360                 365

Leu Ala Ser Lys Cys Val Thr Asp Glu Cys Phe Phe Phe Glu Arg Leu
    370                 375                 380

Glu Ser Asn Asn Tyr Asn Thr Tyr Arg Ser Arg Lys Tyr Thr Ser Trp
385                 390                 395                 400

Tyr Val Ala Leu Lys Arg Thr Gly Gln Tyr Lys Leu Gly Ser Lys Thr
                405                 410                 415

Gly Pro Gly Gln Lys Ala Ile Leu Phe Leu Pro Met Ser Ala Ala Ser
            420                 425                 430

Asp Glu Leu Pro Gln Leu Val Thr Leu Pro His Pro Asn Leu His Gly
        435                 440                 445

Pro Glu Ile Leu Asp Val Pro Ser Thr
    450                 455

(2) INFORMATION FOR SEQ ID NO: 6:

(i) SEQUENCE CHARACTERISTICS:
        (A) LENGTH: 186 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 6:

Gly Ile Arg Gly Leu Lys Gly Thr Lys Gly Glu Lys Gly Glu Asp Gly
1               5                   10                  15

Phe Pro Gly Phe Lys Gly Asp Met Gly Ile Lys Gly Asp Arg Gly Glu
                20                  25                  30

Ile Gly Pro Pro Gly Pro Arg Gly Glu Asp Gly Pro Glu Gly Pro Lys
            35                  40                  45
```

```
Gly Arg Gly Gly Pro Asn Gly Asp Pro Gly Pro Leu Gly Pro Gly
    50                  55                  60

Glu Lys Gly Lys Leu Gly Val Pro Gly Leu Pro Gly Tyr Pro Gly Arg
65                  70                  75                  80

Gln Gly Pro Lys Gly Ser Ile Gly Phe Pro Gly Phe Pro Gly Ala Asn
                85                  90                  95

Gly Glu Lys Gly Gly Arg Gly Thr Pro Gly Lys Pro Gly Pro Arg Gly
                100                 105                 110

Gln Arg Gly Pro Thr Gly Pro Arg Gly Glu Arg Gly Pro Arg Gly Ile
                115                 120                 125

Thr Gly Lys Pro Gly Pro Lys Gly Asn Ser Gly Gly Asp Gly Pro Ala
    130                 135                 140

Gly Pro Pro Gly Glu Arg Gly Pro Asn Gly Pro Gln Gly Pro Thr Gly
145                 150                 155                 160

Phe Pro Gly Pro Lys Gly Pro Pro Gly Pro Pro Gly Lys Asp Gly Leu
                165                 170                 175

Pro Gly His Pro Gly Gln Arg Gly Glu Thr
                180                 185

(2) INFORMATION FOR SEQ ID NO: 7:

(i) SEQUENCE CHARACTERISTICS:
        (A) LENGTH: 464 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 7:

Pro Thr Asp Leu Arg Phe Thr Asn Ile Gly Pro Asp Thr Met Arg Val
1                   5                   10                  15

Thr Trp Ala Pro Pro Ser Ile Asp Leu Thr Asn Phe Leu Val Arg
                20                  25                  30

Tyr Ser Pro Val Lys Asn Glu Glu Asp Val Ala Glu Leu Ser Ile Ser
                35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
                100                 105                 110

Arg Ala Thr Ile Thr Gly Tyr Arg Ile Arg His His Pro Glu His Phe
                115                 120                 125

Ser Gly Arg Pro Arg Glu Asp Arg Val Pro His Ser Arg Asn Ser Ile
                130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
                180                 185                 190

Thr Ser Leu Leu Ile Ser Trp Asp Ala Pro Ala Val Thr Val Arg Tyr
                195                 200                 205
```

```
Tyr Arg Ile Thr Tyr Gly Glu Thr Gly Gly Asn Ser Pro Val Gln Glu
            210                 215                 220
Phe Thr Val Pro Gly Ser Lys Ser Thr Ala Thr Ile Ser Gly Leu Lys
225                 230                 235                 240
Pro Gly Val Asp Tyr Thr Ile Thr Val Tyr Ala Val Thr Gly Arg Gly
                245                 250                 255
Asp Ser Pro Ala Ser Ser Lys Pro Ile Ser Ile Asn Tyr Arg Thr Glu
            260                 265                 270
Ile Asp Lys Pro Ser Met Gly Ile Arg Gly Leu Lys Gly Thr Lys Gly
            275                 280                 285
Glu Lys Gly Glu Asp Gly Phe Pro Gly Phe Lys Gly Asp Met Gly Ile
            290                 295                 300
Lys Gly Asp Arg Gly Glu Ile Gly Pro Pro Gly Pro Arg Gly Glu Asp
305                 310                 315                 320
Gly Pro Glu Gly Pro Lys Gly Arg Gly Gly Pro Asn Gly Asp Pro Gly
                325                 330                 335
Pro Leu Gly Pro Pro Gly Glu Lys Gly Lys Leu Gly Val Pro Gly Leu
            340                 345                 350
Pro Gly Tyr Pro Gly Arg Gln Gly Pro Lys Gly Ser Ile Gly Phe Pro
            355                 360                 365
Gly Phe Pro Gly Ala Asn Gly Glu Lys Gly Gly Arg Gly Thr Pro Gly
            370                 375                 380
Lys Pro Gly Pro Arg Gly Gln Arg Gly Pro Thr Gly Pro Arg Gly Glu
385                 390                 395                 400
Arg Gly Pro Arg Gly Ile Thr Gly Lys Pro Gly Pro Lys Gly Asn Ser
                405                 410                 415
Gly Gly Asp Gly Pro Ala Gly Pro Pro Gly Glu Arg Gly Pro Asn Gly
            420                 425                 430
Pro Gln Gly Pro Thr Gly Phe Pro Gly Pro Lys Gly Pro Pro Gly Pro
            435                 440                 445
Pro Gly Lys Asp Gly Leu Pro Gly His Pro Gly Gln Arg Gly Glu Thr
450                 455                 460

(2) INFORMATION FOR SEQ ID NO: 8:

(i) SEQUENCE CHARACTERISTICS:
        (A) LENGTH: 489 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 8:

Pro Thr Asp Leu Arg Phe Thr Asn Ile Gly Pro Asp Thr Met Arg Val
1               5                   10                  15
Thr Trp Ala Pro Pro Ser Ile Asp Leu Thr Asn Phe Leu Val Arg
                20                  25                  30
Tyr Ser Pro Val Lys Asn Glu Glu Asp Val Ala Glu Leu Ser Ile Ser
            35                  40                  45
Pro Ser Asp Asn Ala Val Val Leu Thr Asn Leu Leu Pro Gly Thr Glu
50                  55                  60
Tyr Val Val Ser Val Ser Ser Val Tyr Glu Gln His Glu Ser Thr Pro
65                  70                  75                  80
Leu Arg Gly Arg Gln Lys Thr Gly Leu Asp Ser Pro Thr Gly Ile Asp
                85                  90                  95
```

```
Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
            115                 120                 125

Ser Gly Arg Pro Arg Glu Asp Arg Val Pro His Ser Arg Asn Ser Ile
            130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
            195                 200                 205

Tyr Arg Ile Thr Tyr Gly Glu Thr Gly Gly Asn Ser Pro Val Gln Glu
            210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Gly Ile Arg Gly Leu Lys Gly Thr Lys Gly
            275                 280                 285

Glu Lys Gly Glu Asp Gly Phe Pro Gly Phe Lys Gly Asp Met Gly Ile
            290                 295                 300

Lys Gly Asp Arg Gly Glu Ile Gly Pro Pro Gly Pro Arg Gly Glu Asp
305                 310                 315                 320

Gly Pro Glu Gly Pro Lys Gly Arg Gly Gly Pro Asn Gly Asp Pro Gly
            325                 330                 335

Pro Leu Gly Pro Pro Gly Glu Lys Gly Lys Leu Gly Val Pro Gly Leu
            340                 345                 350

Pro Gly Tyr Pro Gly Arg Gln Gly Pro Lys Gly Ser Ile Gly Phe Pro
            355                 360                 365

Gly Phe Pro Gly Ala Asn Gly Glu Lys Gly Gly Arg Gly Thr Pro Gly
            370                 375                 380

Lys Pro Gly Pro Arg Gly Gln Arg Gly Pro Thr Gly Pro Arg Gly Glu
385                 390                 395                 400

Arg Gly Pro Arg Gly Ile Thr Gly Lys Pro Gly Pro Lys Gly Asn Ser
                405                 410                 415

Gly Gly Asp Gly Pro Ala Gly Pro Pro Gly Glu Arg Gly Pro Asn Gly
            420                 425                 430

Pro Gln Gly Pro Thr Gly Phe Pro Gly Pro Lys Gly Pro Pro Gly Pro
            435                 440                 445

Pro Gly Lys Asp Gly Leu Pro Gly His Pro Gly Gln Arg Gly Ala Ser
            450                 455                 460

Asp Glu Leu Pro Gln Leu Val Thr Leu Pro His Pro Asn Leu His Gly
465                 470                 475                 480

Pro Glu Ile Leu Asp Val Pro Ser Thr
            485

(2) INFORMATION FOR SEQ ID NO: 9:

(i) SEQUENCE CHARACTERISTICS:
```

(A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

AAACCATGGC AGTCAGCGAC GAGCTTCCCC AACTGG                          36

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

AATTGACAAA CCATCCATGG                                            20

(2) INFORMATION FOR SEQ ID NO: 11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 11:

CCATTAAAAT CAGCTAGCAG CAGACATTGG AAG                             33

(2) INFORMATION FOR SEQ ID NO: 12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 12:

TCTAGAGGAT CCTTAGCTAG CGCCTCTCTG TCCAGG                          36

(2) INFORMATION FOR SEQ ID NO: 13:

(i) SEQUENCE CHARACTERISTICS:
        (A) LENGTH: 547 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 13:

Ala Ala Ser Ala Ile Pro Ala Pro Thr Asp Leu Lys Phe Thr Gln Val
1               5                   10                  15

Thr Pro Thr Ser Leu Ser Ala Gln Trp Thr Pro Pro Asn Val Gln Leu
            20                  25                  30

Thr Gly Tyr Arg Val Arg Val Thr Pro Lys Glu Lys Thr Gly Pro Met
        35                  40                  45

Lys Glu Ile Asn Leu Ala Pro Asp Ser Ser Ser Val Val Val Ser Gly

```
            50                  55                  60
Leu Met Val Ala Thr Lys Tyr Glu Val Ser Val Tyr Ala Leu Lys Asp
 65                  70                  75                  80

Thr Leu Thr Ser Arg Pro Ala Gln Gly Val Val Thr Thr Leu Glu Asn
                 85                  90                  95

Val Ser Pro Pro Arg Ala Arg Val Thr Asp Ala Thr Glu Thr Thr
            100                 105                 110

Ile Thr Ile Ser Trp Arg Thr Lys Thr Glu Thr Ile Thr Gly Phe Gln
            115                 120                 125

Val Asp Ala Val Pro Ala Asn Gly Gln Thr Pro Ile Gln Arg Thr Ile
130                 135                 140

Lys Pro Asp Val Arg Ser Tyr Thr Ile Thr Gly Leu Gln Pro Gly Thr
145                 150                 155                 160

Asp Tyr Lys Ile Tyr Leu Tyr Thr Leu Asn Asp Asn Ala Arg Ser Ser
                165                 170                 175

Pro Val Val Ile Asp Ala Ser Thr Ala Ile Asp Ala Pro Ser Asn Leu
            180                 185                 190

Arg Phe Leu Ala Thr Thr Pro Asn Ser Leu Leu Val Ser Trp Gln Pro
            195                 200                 205

Pro Arg Ala Arg Ile Thr Gly Tyr Ile Ile Lys Tyr Glu Lys Pro Gly
210                 215                 220

Ser Pro Pro Arg Glu Val Val Pro Arg Pro Arg Pro Gly Val Thr Glu
225                 230                 235                 240

Ala Thr Ile Thr Gly Leu Glu Pro Gly Thr Glu Tyr Thr Ile Tyr Val
                245                 250                 255

Ile Ala Leu Lys Asn Asn Gln Lys Ser Glu Pro Leu Ile Gly Arg Lys
            260                 265                 270

Lys Thr Ser Ala Ile Pro Ala Pro Thr Asp Leu Lys Phe Thr Gln Val
            275                 280                 285

Thr Pro Thr Ser Leu Ser Ala Gln Trp Thr Pro Pro Asn Val Gln Leu
            290                 295                 300

Thr Gly Tyr Arg Val Arg Val Thr Pro Lys Glu Lys Thr Gly Pro Met
305                 310                 315                 320

Lys Glu Ile Asn Leu Ala Pro Asp Ser Ser Val Val Ser Gly
                325                 330                 335

Leu Met Val Ala Thr Lys Tyr Glu Val Ser Val Tyr Ala Leu Lys Asp
                340                 345                 350

Thr Leu Thr Ser Arg Pro Ala Gln Gly Val Val Thr Thr Leu Glu Asn
            355                 360                 365

Val Ser Pro Pro Arg Arg Ala Arg Val Thr Asp Ala Thr Glu Thr Thr
370                 375                 380

Ile Thr Ile Ser Trp Arg Thr Lys Thr Glu Thr Ile Thr Gly Phe Gln
385                 390                 395                 400

Val Asp Ala Val Pro Ala Asn Gly Gln Thr Pro Ile Gln Arg Thr Ile
                405                 410                 415

Lys Pro Asp Val Arg Ser Tyr Thr Ile Thr Gly Leu Gln Pro Gly Thr
            420                 425                 430

Asp Tyr Lys Ile Tyr Leu Tyr Thr Leu Asn Asp Asn Ala Arg Ser Ser
            435                 440                 445

Pro Val Val Ile Asp Ala Ser Thr Ala Ile Asp Ala Pro Ser Asn Leu
            450                 455                 460

Arg Phe Leu Ala Thr Thr Pro Asn Ser Leu Leu Val Ser Trp Gln Pro
465                 470                 475                 480
```

```
Pro Arg Ala Arg Ile Thr Gly Tyr Ile Ile Lys Tyr Glu Lys Pro Gly
                485                 490                 495

Ser Pro Pro Arg Glu Val Val Pro Arg Pro Arg Pro Gly Val Thr Glu
            500                 505                 510

Ala Thr Ile Thr Gly Leu Glu Pro Gly Thr Glu Tyr Thr Ile Tyr Val
        515                 520                 525

Ile Ala Leu Lys Asn Asn Gln Lys Ser Glu Pro Leu Ile Gly Arg Lys
    530                 535                 540

Lys Thr Ser
545

(2) INFORMATION FOR SEQ ID NO: 14:

(i) SEQUENCE CHARACTERISTICS:
        (A) LENGTH: 826 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 14:

Ala Ala Ser Pro Thr Asp Leu Arg Phe Thr Asn Ile Gly Pro Asp Thr
1               5                   10                  15

Met Arg Val Thr Trp Ala Pro Pro Ser Ile Asp Leu Thr Asn Phe
            20                  25                  30

Leu Val Arg Tyr Ser Pro Val Lys Asn Glu Glu Asp Val Ala Glu Leu
            35                  40                  45

Ser Ile Ser Pro Ser Asp Asn Ala Val Val Leu Thr Asn Leu Leu Pro
    50                  55                  60

Gly Thr Glu Tyr Val Val Ser Val Ser Ser Val Tyr Glu Gln His Glu
65                  70                  75                  80

Ser Thr Pro Leu Arg Gly Arg Gln Lys Thr Gly Leu Asp Ser Pro Thr
            85                  90                  95

Gly Ile Asp Phe Ser Asp Ile Thr Ala Asn Ser Phe Thr Val His Trp
            100                 105                 110

Ile Ala Pro Arg Ala Thr Ile Thr Gly Tyr Arg Ile Arg His His Pro
            115                 120                 125

Glu His Phe Ser Gly Arg Pro Arg Glu Asp Arg Val Pro His Ser Arg
    130                 135                 140

Asn Ser Ile Thr Leu Thr Asn Leu Thr Pro Gly Thr Glu Tyr Val Val
145                 150                 155                 160

Ser Ile Val Ala Leu Asn Gly Arg Glu Glu Ser Pro Leu Leu Ile Gly
            165                 170                 175

Gln Gln Ser Thr Val Ser Asp Val Pro Arg Asp Leu Glu Val Val Ala
            180                 185                 190

Ala Thr Pro Thr Ser Leu Leu Ile Ser Trp Asp Ala Pro Ala Val Thr
            195                 200                 205

Val Arg Tyr Tyr Arg Ile Thr Tyr Gly Glu Thr Gly Gly Asn Ser Pro
            210                 215                 220

Val Gln Glu Phe Thr Val Pro Gly Ser Lys Ser Thr Ala Thr Ile Ser
225                 230                 235                 240

Gly Leu Lys Pro Gly Val Asp Tyr Thr Ile Thr Val Tyr Ala Val Thr
            245                 250                 255

Gly Arg Gly Asp Ser Pro Ala Ser Ser Lys Pro Ile Ser Ile Asn Tyr
            260                 265                 270
```

```
Arg Thr Glu Ile Asp Lys Pro Ser Thr Ser Ala Ile Pro Ala Pro Thr
            275                 280                 285

Asp Leu Lys Phe Thr Gln Val Thr Pro Thr Ser Leu Ser Ala Gln Trp
        290                 295                 300

Thr Pro Pro Asn Val Gln Leu Thr Gly Tyr Arg Val Arg Val Thr Pro
305                 310                 315                 320

Lys Glu Lys Thr Gly Pro Met Lys Glu Ile Asn Leu Ala Pro Asp Ser
                325                 330                 335

Ser Ser Val Val Val Ser Gly Leu Met Val Ala Thr Lys Tyr Glu Val
            340                 345                 350

Ser Val Tyr Ala Leu Lys Asp Thr Leu Thr Ser Arg Pro Ala Gln Gly
        355                 360                 365

Val Val Thr Thr Leu Glu Asn Val Ser Pro Pro Arg Ala Arg Val
        370                 375                 380

Thr Asp Ala Thr Glu Thr Thr Ile Thr Ile Ser Trp Arg Thr Lys Thr
385                 390                 395                 400

Glu Thr Ile Thr Gly Phe Gln Val Asp Ala Val Pro Ala Asn Gly Gln
                405                 410                 415

Thr Pro Ile Gln Arg Thr Ile Lys Pro Asp Val Arg Ser Tyr Thr Ile
            420                 425                 430

Thr Gly Leu Gln Pro Gly Thr Asp Tyr Lys Ile Tyr Leu Tyr Thr Leu
        435                 440                 445

Asn Asp Asn Ala Arg Ser Ser Pro Val Val Ile Asp Ala Ser Thr Ala
450                 455                 460

Ile Asp Ala Pro Ser Asn Leu Arg Phe Leu Ala Thr Thr Pro Asn Ser
465                 470                 475                 480

Leu Leu Val Ser Trp Gln Pro Pro Arg Ala Arg Ile Thr Gly Tyr Ile
                485                 490                 495

Ile Lys Tyr Glu Lys Pro Gly Ser Pro Pro Arg Glu Val Val Pro Arg
            500                 505                 510

Pro Arg Pro Gly Val Thr Glu Ala Thr Ile Thr Gly Leu Glu Pro Gly
        515                 520                 525

Thr Glu Tyr Thr Ile Tyr Val Ile Ala Leu Lys Asn Asn Gln Lys Ser
530                 535                 540

Glu Pro Leu Ile Gly Arg Lys Lys Thr Ser Ala Ile Pro Ala Pro Thr
545                 550                 555                 560

Asp Leu Lys Phe Thr Gln Val Thr Pro Thr Ser Leu Ser Ala Gln Trp
                565                 570                 575

Thr Pro Pro Asn Val Gln Leu Thr Gly Tyr Arg Val Arg Val Thr Pro
            580                 585                 590

Lys Glu Lys Thr Gly Pro Met Lys Glu Ile Asn Leu Ala Pro Asp Ser
        595                 600                 605

Ser Ser Val Val Val Ser Gly Leu Met Val Ala Thr Lys Tyr Glu Val
610                 615                 620

Ser Val Tyr Ala Leu Lys Asp Thr Leu Thr Ser Arg Pro Ala Gln Gly
625                 630                 635                 640

Val Val Thr Thr Leu Glu Asn Val Ser Pro Pro Arg Arg Ala Arg Val
                645                 650                 655

Thr Asp Ala Thr Glu Thr Thr Ile Thr Ile Ser Trp Arg Thr Lys Thr
            660                 665                 670

Glu Thr Ile Thr Gly Phe Gln Val Asp Ala Val Pro Ala Asn Gly Gln
        675                 680                 685
```

```
Thr Pro Ile Gln Arg Thr Ile Lys Pro Asp Val Arg Ser Tyr Thr Ile
    690                 695                 700

Thr Gly Leu Gln Pro Gly Thr Asp Tyr Lys Ile Tyr Leu Tyr Thr Leu
705                 710                 715                 720

Asn Asp Asn Ala Arg Ser Ser Pro Val Val Ile Asp Ala Ser Thr Ala
                725                 730                 735

Ile Asp Ala Pro Ser Asn Leu Arg Phe Leu Ala Thr Thr Pro Asn Ser
            740                 745                 750

Leu Leu Val Ser Trp Gln Pro Pro Arg Ala Arg Ile Thr Gly Tyr Ile
        755                 760                 765

Ile Lys Tyr Glu Lys Pro Gly Ser Pro Pro Arg Glu Val Val Pro Arg
    770                 775                 780

Pro Arg Pro Gly Val Thr Glu Ala Thr Ile Thr Gly Leu Glu Pro Gly
785                 790                 795                 800

Thr Glu Tyr Thr Ile Tyr Val Ile Ala Leu Lys Asn Asn Gln Lys Ser
                805                 810                 815

Glu Pro Leu Ile Gly Arg Lys Lys Thr Ser
            820                 825
```

(2) INFORMATION FOR SEQ ID NO: 15:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

```
AAACCATGGC AGCTAGCGCT ATTCCTGCAC CAACTGAC                           38
```

(2) INFORMATION FOR SEQ ID NO: 16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

```
AAAGGATCCC TAACTAGTCT TTTTCCTTCC AATCAG                             36
```

(2) INFORMATION FOR SEQ ID NO: 17:

(i) SEQUENCE CHARACTERISTICS:
        (A) LENGTH: 1644 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 17:

```
ATGGCAGCTA GCGCTATTCC TGCACCAACT GACCTGAAGT TCACTCAGGT CACACCCACA    60

AGCCTGAGCG CCCAGTGGAC ACCACCCAAT GTTCAGCTCA CTGGATATCG AGTGCGGGTG   120

ACCCCCAAGG AGAAGACCGG ACCAATGAAA GAAATCAACC TTGCTCCTGA CAGCTCATCC   180

GTGGTTGTAT CAGGACTTAT GGTGGCCACC AAATATGAAG TGAGTGTCTA TGCTCTTAAG   240

GACACTTTGA CAAGCAGACC AGCTCAGGGT GTTGTCACCA CTCTGGAGAA TGTCAGCCCA   300
```

```
CCAAGAAGGG CTCGTGTGAC AGATGCTACT GAGACCACCA TCACCATTAG CTGGAGAACC      360

AAGACTGAGA CGATCACTGG CTTCCAAGTT GATGCCGTTC CAGCCAATGG CCAGACTCCA      420

ATCCAGAGAA CCATCAAGCC AGATGTCAGA AGCTACACCA TCACAGGTTT ACAACCAGGC      480

ACTGACTACA AGATCTACCT GTACACCTTG AATGACAATG CTCGGAGCTC CCCTGTGGTC      540

ATCGACGCCT CCACTGCCAT TGATGCACCA TCCAACCTGC GTTTCCTGGC CACCACACCC      600

AATTCCTTGC TGGTATCATG GCAGCCGCCA CGTGCCAGGA TTACCGGCTA CATCATCAAG      660

TATGAGAAGC CTGGGTCTCC TCCCAGAGAA GTGGTCCCTC GGCCCCGCCC TGGTGTCACA      720

GAGGCTACTA TTACTGGCCT GGAACCGGGA ACCGAATATA CAATTTATGT CATTGCCCTG      780

AAGAATAATC AGAAGAGCGA GCCCCTGATT GGAAGGAAAA AGACTAGCGC TATTCCTGCA      840

CCAACTGACC TGAAGTTCAC TCAGGTCACA CCCACAAGCC TGAGCGCCCA GTGGACACCA      900

CCCAATGTTC AGCTCACTGG ATATCGAGTG CGGGTGACCC CCAAGGAGAA GACCGGACCA      960

ATGAAAGAAA TCAACCTTGC TCCTGACAGC TCATCCGTGG TTGTATCAGG ACTTATGGTG     1020

GCCACCAAAT ATGAAGTGAG TGTCTATGCT CTTAAGGACA CTTTGACAAG CAGACCAGCT     1080

CAGGGTGTTG TCACCACTCT GGAGAATGTC AGCCCACCAA GAAGGGCTCG TGTGACAGAT     1140

GCTACTGAGA CCACCATCAC CATTAGCTGG AGAACCAAGA CTGAGACGAT CACTGGCTTC     1200

CAAGTTGATG CCGTTCCAGC CAATGGCCAG ACTCCAATCC AGAGAACCAT CAAGCCAGAT     1260

GTCAGAAGCT ACACCATCAC AGGTTTACAA CCAGGCACTG ACTACAAGAT CTACCTGTAC     1320

ACCTTGAATG ACAATGCTCG GAGCTCCCCT GTGGTCATCG ACGCCTCCAC TGCCATTGAT     1380

GCACCATCCA ACCTGCGTTT CCTGGCCACC ACACCCAATT CCTTGCTGGT ATCATGGCAG     1440

CCGCCACGTG CCAGGATTAC CGGCTACATC ATCAAGTATG AGAAGCCTGG GTCTCCTCCC     1500

AGAGAAGTGG TCCCTCGGCC CCGCCCTGGT GTCACAGAGG CTACTATTAC TGGCCTGGAA     1560

CCGGGAACCG AATATACAAT TTATGTCATT GCCCTGAAGA ATAATCAGAA GAGCGAGCCC     1620

CTGATTGGAA GGAAAAAGAC TAGT                                           1644

(2) INFORMATION FOR SEQ ID NO: 18:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

AAACCATGGC AGCTAGCCCC ACTGACCTGC GATTCAC                                37

(2) INFORMATION FOR SEQ ID NO: 19:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 19:

AAAAGATCTC TAACTAGTGG ATGGTTTGTC AATTTCTG                               38

(2) INFORMATION FOR SEQ ID NO: 20:
```

```
    (i) SEQUENCE CHARACTERISTICS:
        (A) LENGTH: 2481 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 20:

ATGGCAGCTA GCCCCACTGA CCTGCGATTC ACCAACATTG GTCCAGACAC CATGCGTGTC      60

ACCTGGGCTC CACCCCCATC CATTGATTTA ACCAACTTCC TGGTGCGTTA CTCACCTGTG     120

AAAAATGAGG AAGATGTTGC AGAGTTGTCA ATTTCTCCTT CAGACAATGC AGTGGTCTTA     180

ACAAATCTCC TGCCTGGTAC AGAATATGTA GTGAGTGTCT CCAGTGTCTA CGAACAACAT     240

GAGAGCACAC CTCTTAGAGG AAGACAGAAA ACAGGTCTTG ATTCCCCAAC TGGCATTGAC     300

TTTTCTGATA TTACTGCCAA CTCTTTTACT GTGCACTGGA TTGCTCCTCG AGCCACCATC     360

ACTGGCTACA GGATCCGCCA TCATCCCGAG CACTTCAGTG GGAGACCTCG AGAAGATCGG     420

GTGCCCCACT CTCGGAATTC CATCACCCTC ACCAACCTCA CTCCAGGCAC AGAGTATGTG     480

GTCAGCATCG TTGCTCTTAA TGGCAGAGAG GAAAGTCCCT TATTGATTGG CCAACAATCA     540

ACAGTTTCTG ATGTTCCGAG GGACCTGGAA GTTGTTGCTG CGACCCCCAC CAGCCTACTG     600

ATCAGCTGGG ATGCTCCTGC TGTCACAGTG AGATATTACA GGATCACTTA CGGAGAAACA     660

GGAGGAAATA GCCCTGTCCA GGAGTTCACT GTGCCTGGGA GCAAGTCTAC AGCTACCATC     720

AGCGGCCTTA AACCTGGAGT TGATTATACC ATCACTGTGT ATGCTGTCAC TGGCCGTGGA     780

GACAGCCCCG CAAGCAGCAA GCCAATTTCC ATTAATTACC GAACAGAAAT TGACAAACCA     840

TCCACTAGCG CTATTCCTGC ACCAACTGAC CTGAAGTTCA CTCAGGTCAC ACCCACAAGC     900

CTGAGCGCCC AGTGGACACC ACCCAATGTT CAGCTCACTG GATATCGAGT GCGGGTGACC     960

CCCAAGGAGA AGACCGGACC AATGAAAGAA ATCAACCTTG CTCCTGACAG CTCATCCGTG    1020

GTTGTATCAG GACTTATGGT GGCCACCAAA TATGAAGTGA GTGTCTATGC TCTTAAGGAC    1080

ACTTTGACAA GCAGACCAGC TCAGGGTGTT GTCACCACTC TGGAGAATGT CAGCCCACCA    1140

AGAAGGGCTC GTGTGACAGA TGCTACTGAG ACCACCATCA CCATTAGCTG GAGAACCAAG    1200

ACTGAGACGA TCACTGGCTT CCAAGTTGAT GCCGTTCCAG CCAATGGCCA GACTCCAATC    1260

CAGAGAACCA TCAAGCCAGA TGTCAGAAGC TACACCATCA CAGGTTTACA ACCAGGCACT    1320

GACTACAAGA TCTACCTGTA CACCTTGAAT GACAATGCTC GGAGCTCCCC TGTGGTCATC    1380

GACGCCTCCA CTGCCATTGA TGCACCATCC AACCTGCGTT TCCTGGCCAC CACACCCAAT    1440

TCCTTGCTGG TATCATGGCA GCCGCCACGT GCCAGGATTA CCGGCTACAT CATCAAGTAT    1500

GAGAAGCCTG GGTCTCCTCC CAGAGAAGTG GTCCCTCGGC CCCGCCCTGG TGTCACAGAG    1560

GCTACTATTA CTGGCCTGGA ACCGGGAACC GAATATACAA TTTATGTCAT TGCCCTGAAG    1620

AATAATCAGA GAGCGAGCC CCTGATTGGA AGGAAAAAGA CTAGCGCTAT TCCTGCACCA    1680

ACTGACCTGA AGTTCACTCA GGTCACACCC ACAAGCCTGA GCGCCCAGTG GACACCACCC    1740

AATGTTCAGC TCACTGGATA TCGAGTGCGG GTGACCCCCA AGGAGAAGAC CGGACCAATG    1800

AAAGAAATCA ACCTTGCTCC TGACAGCTCA TCCGTGGTTG TATCAGGACT TATGGTGGCC    1860

ACCAAATATG AAGTGAGTGT CTATGCTCTT AAGGACACTT TGACAAGCAG ACCAGCTCAG    1920

GGTGTTGTCA CCACTCTGGA GAATGTCAGC CCACCAAGAA GGGCTCGTGT GACAGATGCT    1980

ACTGAGACCA CCATCACCAT TAGCTGGAGA ACCAAGACTG AGACGATCAC TGGCTTCCAA    2040
```

```
GTTGATGCCG TTCCAGCCAA TGGCCAGACT CCAATCCAGA GAACCATCAA GCCAGATGTC    2100

AGAAGCTACA CCATCACAGG TTTACAACCA GGCACTGACT ACAAGATCTA CCTGTACACC    2160

TTGAATGACA ATGCTCGGAG CTCCCCTGTG GTCATCGACG CCTCCACTGC CATTGATGCA    2220

CCATCCAACC TGCGTTTCCT GGCCACCACA CCCAATTCCT TGCTGGTATC ATGGCAGCCG    2280

CCACGTGCCA GGATTACCGG CTACATCATC AAGTATGAGA AGCCTGGGTC TCCTCCCAGA    2340

GAAGTGGTCC CTCGGCCCCG CCCTGGTGTC ACAGAGGCTA CTATTACTGG CCTGGAACCG    2400

GGAACCGAAT ATACAATTTA TGTCATTGCC CTGAAGAATA TCAGAAGAG CGAGCCCCTG     2460

ATTGGAAGGA AAAAGACTAG T                                              2481
```

(2) INFORMATION FOR SEQ ID NO: 21:

(i) SEQUENCE CHARACTERISTICS:
        (A) LENGTH: 472 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 21:

```
Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
        35                  40                  45

Pro Ser Asp Asn Ala Val Val Leu Thr Asn Leu Leu Pro Gly Thr Glu
50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270
```

```
Ile Asp Lys Pro Ser Met Ala Ile Pro Ala Pro Thr Asp Leu Lys Phe
            275                 280                 285

Thr Gln Val Thr Pro Thr Ser Leu Ser Ala Gln Trp Thr Pro Pro Asn
        290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
                325                 330                 335

Val Ser Gly Leu Met Val Ala Thr Lys Tyr Glu Val Ser Val Tyr Ala
            340                 345                 350

Leu Lys Asp Thr Leu Thr Ser Arg Pro Ala Gln Gly Val Val Thr Thr
        355                 360                 365

Leu Glu Asn Val Ser Pro Pro Arg Arg Ala Arg Val Thr Asp Ala Thr
    370                 375                 380

Glu Thr Thr Ile Thr Ile Ser Trp Arg Thr Lys Thr Glu Thr Ile Thr
385                 390                 395                 400

Gly Phe Gln Val Asp Ala Val Pro Ala Asn Gly Gln Thr Pro Ile Gln
                405                 410                 415

Arg Thr Ile Lys Pro Asp Val Arg Ser Tyr Thr Ile Thr Gly Leu Gln
            420                 425                 430

Pro Gly Thr Asp Tyr Lys Ile Tyr Leu Tyr Thr Leu Asn Asp Asn Ala
        435                 440                 445

Arg Ser Ser Pro Val Val Ile Asp Ala Ser Thr Ala Ile Asp Ala Pro
    450                 455                 460

Ser Asn Leu Arg Phe Leu Ala Thr
465                 470

(2) INFORMATION FOR SEQ ID NO: 22:

(i) SEQUENCE CHARACTERISTICS:
        (A) LENGTH: 457 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 22:

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
    130                 135                 140
```

```
Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
            165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
            195                 200                 205

Tyr Arg Ile Thr Tyr Gly Glu Thr Gly Gly Asn Ser Pro Val Gln Glu
        210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
            245                 250                 255

Asp Ser Pro Ala Ser Ser Lys Pro Ile Ser Ile Asn Tyr Arg Thr Glu
            260                 265                 270

Ile Asp Lys Pro Ser Met Asn Val Ser Pro Pro Arg Arg Ala Arg Val
        275                 280                 285

Thr Asp Ala Thr Glu Thr Thr Ile Thr Ile Ser Trp Arg Thr Lys Thr
290                 295                 300

Glu Thr Ile Thr Gly Phe Gln Val Asp Ala Val Pro Ala Asn Gly Gln
305                 310                 315                 320

Thr Pro Ile Gln Arg Thr Ile Lys Pro Asp Val Arg Ser Tyr Thr Ile
            325                 330                 335

Thr Gly Leu Gln Pro Gly Thr Asp Tyr Lys Ile Tyr Leu Tyr Thr Leu
            340                 345                 350

Asn Asp Asn Ala Arg Ser Ser Pro Val Val Ile Asp Ala Ser Thr Ala
            355                 360                 365

Ile Asp Ala Pro Ser Asn Leu Arg Phe Leu Ala Thr Thr Pro Asn Ser
        370                 375                 380

Leu Leu Val Ser Trp Gln Pro Pro Arg Ala Arg Ile Thr Gly Tyr Ile
385                 390                 395                 400

Ile Lys Tyr Glu Lys Pro Gly Ser Pro Pro Arg Glu Val Val Pro Arg
            405                 410                 415

Pro Arg Pro Gly Val Thr Glu Ala Thr Ile Thr Gly Leu Glu Pro Gly
            420                 425                 430

Thr Glu Tyr Thr Ile Tyr Val Ile Ala Leu Lys Asn Asn Gln Lys Ser
            435                 440                 445

Glu Pro Leu Ile Gly Arg Lys Lys Thr
    450                 455
```

(2) INFORMATION FOR SEQ ID NO: 23:

(i) SEQUENCE CHARACTERISTICS:
        (A) LENGTH: 549 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 23:

```
Pro Thr Asp Leu Arg Phe Thr Asn Ile Gly Pro Asp Thr Met Arg Val
1               5                   10                  15

Thr Trp Ala Pro Pro Pro Ser Ile Asp Leu Thr Asn Phe Leu Val Arg
            20                  25                  30
```

-continued

Tyr Ser Pro Val Lys Asn Glu Glu Asp Val Ala Glu Leu Ser Ile Ser
        35                  40                  45
Pro Ser Asp Asn Ala Val Val Leu Thr Asn Leu Leu Pro Gly Thr Glu
 50                  55                  60
Tyr Val Val Ser Val Ser Ser Val Tyr Glu Gln His Glu Ser Thr Pro
 65                  70                  75                  80
Leu Arg Gly Arg Gln Lys Thr Gly Leu Asp Ser Pro Thr Gly Ile Asp
                85                  90                  95
Phe Ser Asp Ile Thr Ala Asn Ser Phe Thr Val His Trp Ile Ala Pro
            100                 105                 110
Arg Ala Thr Ile Thr Gly Tyr Arg Ile Arg His His Pro Glu His Phe
        115                 120                 125
Ser Gly Arg Pro Arg Glu Asp Arg Val Pro His Ser Arg Asn Ser Ile
130                 135                 140
Thr Leu Thr Asn Leu Thr Pro Gly Thr Glu Tyr Val Val Ser Ile Val
145                 150                 155                 160
Ala Leu Asn Gly Arg Glu Glu Ser Pro Leu Leu Ile Gly Gln Gln Ser
                165                 170                 175
Thr Val Ser Asp Val Pro Arg Asp Leu Glu Val Val Ala Ala Thr Pro
            180                 185                 190
Thr Ser Leu Leu Ile Ser Trp Asp Ala Pro Ala Val Thr Val Arg Tyr
        195                 200                 205
Tyr Arg Ile Thr Tyr Gly Glu Thr Gly Gly Asn Ser Pro Val Gln Glu
210                 215                 220
Phe Thr Val Pro Gly Ser Lys Ser Thr Ala Thr Ile Ser Gly Leu Lys
225                 230                 235                 240
Pro Gly Val Asp Tyr Thr Ile Thr Val Tyr Ala Val Thr Gly Arg Gly
                245                 250                 255
Asp Ser Pro Ala Ser Ser Lys Pro Ile Ser Ile Asn Tyr Arg Thr Glu
            260                 265                 270
Ile Asp Lys Pro Ser Met Ala Ile Pro Ala Pro Thr Asp Leu Lys Phe
        275                 280                 285
Thr Gln Val Thr Pro Thr Ser Leu Ser Ala Gln Trp Thr Pro Pro Asn
290                 295                 300
Val Gln Leu Thr Gly Tyr Arg Val Arg Val Thr Pro Lys Glu Lys Thr
305                 310                 315                 320
Gly Pro Met Lys Glu Ile Asn Leu Ala Pro Asp Ser Ser Ser Val Val
                325                 330                 335
Val Ser Gly Leu Met Val Ala Thr Lys Tyr Glu Val Ser Val Tyr Ala
            340                 345                 350
Leu Lys Asp Thr Leu Thr Ser Arg Pro Ala Gln Gly Val Val Thr Thr
        355                 360                 365
Leu Glu Asn Val Ser Pro Pro Arg Arg Ala Arg Val Thr Asp Ala Thr
370                 375                 380
Glu Thr Thr Ile Thr Ile Ser Trp Arg Thr Lys Thr Glu Thr Ile Thr
385                 390                 395                 400
Gly Phe Gln Val Asp Ala Val Pro Ala Asn Gly Gln Thr Pro Ile Gln
                405                 410                 415
Arg Thr Ile Lys Pro Asp Val Arg Ser Tyr Thr Ile Thr Gly Leu Gln
            420                 425                 430
Pro Gly Thr Asp Tyr Lys Ile Tyr Leu Tyr Thr Leu Asn Asp Asn Ala
        435                 440                 445

```
Arg Ser Ser Pro Val Val Ile Asp Ala Ser Thr Ala Ile Asp Ala Pro
    450                 455                 460

Ser Asn Leu Arg Phe Leu Ala Thr Thr Pro Asn Ser Leu Leu Val Ser
465                 470                 475                 480

Trp Gln Pro Pro Arg Ala Arg Ile Thr Gly Tyr Ile Ile Lys Tyr Glu
                485                 490                 495

Lys Pro Gly Ser Pro Pro Arg Glu Val Val Pro Arg Pro Arg Pro Gly
            500                 505                 510

Val Thr Glu Ala Thr Ile Thr Gly Leu Glu Pro Gly Thr Glu Tyr Thr
                515                 520                 525

Ile Tyr Val Ile Ala Leu Lys Asn Asn Gln Lys Ser Glu Pro Leu Ile
    530                 535                 540

Gly Arg Lys Lys Thr
545

(2) INFORMATION FOR SEQ ID NO: 24:

(i) SEQUENCE CHARACTERISTICS:
        (A) LENGTH: 574 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 24:

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
                20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
            115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
            195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240
```

-continued

```
Pro Gly Val Asp Tyr Thr Ile Thr Val Tyr Ala Val Thr Gly Arg Gly
            245                 250                 255

Asp Ser Pro Ala Ser Ser Lys Pro Ile Ser Ile Asn Tyr Arg Thr Glu
            260                 265                 270

Ile Asp Lys Pro Ser Met Ala Ile Pro Ala Pro Thr Asp Leu Lys Phe
            275                 280                 285

Thr Gln Val Thr Pro Thr Ser Leu Ser Ala Gln Trp Thr Pro Pro Asn
            290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
            325                 330                 335

Val Ser Gly Leu Met Val Ala Thr Lys Tyr Glu Val Ser Val Tyr Ala
            340                 345                 350

Leu Lys Asp Thr Leu Thr Ser Arg Pro Ala Gln Gly Val Val Thr Thr
            355                 360                 365

Leu Glu Asn Val Ser Pro Pro Arg Arg Ala Arg Val Thr Asp Ala Thr
            370                 375                 380

Glu Thr Thr Ile Thr Ile Ser Trp Arg Thr Lys Thr Glu Thr Ile Thr
385                 390                 395                 400

Gly Phe Gln Val Asp Ala Val Pro Ala Asn Gly Gln Thr Pro Ile Gln
            405                 410                 415

Arg Thr Ile Lys Pro Asp Val Arg Ser Tyr Thr Ile Thr Gly Leu Gln
            420                 425                 430

Pro Gly Thr Asp Tyr Lys Ile Tyr Leu Tyr Thr Leu Asn Asp Asn Ala
            435                 440                 445

Arg Ser Ser Pro Val Val Ile Asp Ala Ser Thr Ala Ile Asp Ala Pro
            450                 455                 460

Ser Asn Leu Arg Phe Leu Ala Thr Thr Pro Asn Ser Leu Leu Val Ser
465                 470                 475                 480

Trp Gln Pro Pro Arg Ala Arg Ile Thr Gly Tyr Ile Ile Lys Tyr Glu
            485                 490                 495

Lys Pro Gly Ser Pro Pro Arg Glu Val Val Pro Arg Pro Arg Pro Gly
            500                 505                 510

Val Thr Glu Ala Thr Ile Thr Gly Leu Glu Pro Gly Thr Glu Tyr Thr
            515                 520                 525

Ile Tyr Val Ile Ala Leu Lys Asn Asn Gln Lys Ser Glu Pro Leu Ile
            530                 535                 540

Gly Arg Lys Lys Thr Asp Glu Leu Pro Gln Leu Val Thr Leu Pro His
545                 550                 555                 560

Pro Asn Leu His Gly Pro Glu Ile Leu Asp Val Pro Ser Thr
            565                 570
```

(2) INFORMATION FOR SEQ ID NO: 25:

(i) SEQUENCE CHARACTERISTICS:
        (A) LENGTH: 274 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 25:

```
Pro Thr Asp Leu Arg Phe Thr Asn Ile Gly Pro Asp Thr Met Arg Val
1               5                   10                  15
```

-continued

```
Thr Trp Ala Pro Pro Ser Ile Asp Leu Thr Asn Phe Leu Val Arg
         20                  25                  30

Tyr Ser Pro Val Lys Asn Glu Glu Asp Val Ala Glu Leu Ser Ile Ser
     35                  40                  45

Pro Ser Asp Asn Ala Val Val Leu Thr Asn Leu Pro Gly Thr Glu
 50                  55                  60

Tyr Val Val Ser Val Ser Ser Val Tyr Glu Gln His Glu Ser Thr Pro
 65                  70                  75                  80

Leu Arg Gly Arg Gln Lys Thr Gly Leu Asp Ser Pro Thr Gly Ile Asp
                 85                  90                  95

Phe Ser Asp Ile Thr Ala Asn Ser Phe Thr Val His Trp Ile Ala Pro
             100                 105                 110

Arg Ala Thr Ile Thr Gly Tyr Arg Ile Arg His His Pro Glu His Phe
             115                 120                 125

Ser Gly Arg Pro Arg Glu Asp Arg Val Pro His Ser Arg Asn Ser Ile
130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                 165                 170                 175

Thr Val Ser Asp Val Pro Arg Asp Leu Glu Val Val Ala Ala Thr Pro
             180                 185                 190

Thr Ser Leu Leu Ile Ser Trp Asp Ala Pro Ala Val Thr Val Arg Tyr
             195                 200                 205

Tyr Arg Ile Thr Tyr Gly Glu Thr Gly Gly Asn Ser Pro Val Gln Glu
         210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                 245                 250                 255

Asp Ser Pro Ala Ser Ser Lys Pro Ile Ser Ile Asn Tyr Arg Thr Glu
             260                 265                 270

Ile Asp
```

(2) INFORMATION FOR SEQ ID NO: 26:

(i) SEQUENCE CHARACTERISTICS:
        (A) LENGTH: 1374 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 26:

```
ATGCCCACTG ACCTGCGATT CACCAACATT GGTCCAGACA CCATGCGTGT CACCTGGGCT      60

CCACCCCCAT CCATTGATTT AACCAACTTC CTGGTGCGTT ACTCACCTGT GAAAAATGAG     120

GAAGATGTTG CAGAGTTGTC AATTTCTCCT TCAGACAATG CAGTGGTCTT AACAAATCTC     180

CTGCCTGGTA CAGAATATGT AGTGAGTGTC TCCAGTGTCT ACGAACAACA TGAGAGCACA     240

CCTCTTAGAG GAAGACAGAA AACAGGTCTT GATTCCCCAA CTGGCATTGA CTTTTCTGAT     300

ATTACTGCCA ACTCTTTTAC TGTGCACTGG ATTGCTCCTC GAGCCACCAT CACTGGCTAC     360

AGGATCCGCC ATCATCCCGA GCACTTCAGT GGGAGACCTC GAGAAGATCG GGTGCCCCAC     420

TCTCGGAATT CCATCACCCT CACCAACCTC ACTCCAGGCA CAGAGTATGT GGTCAGCATC     480
```

```
GTTGCTCTTA ATGGCAGAGA GGAAAGTCCC TTATTGATTG GCCAACAATC AACAGTTTCT        540

GATGTTCCGA GGGACCTGGA AGTTGTTGCT GCGACCCCCA CCAGCCTACT GATCAGCTGG        600

GATGCTCCTG CTGTCACAGT GAGATATTAC AGGATCACTT ACGGAGAAAC AGGAGGAAAT        660

AGCCCTGTCC AGGAGTTCAC TGTGCCTGGG AGCAAGTCTA CAGCTACCAT CAGCGGCCTT        720

AAACCTGGAG TTGATTATAC CATCACTGTG TATGCTGTCA CTGGCCGTGG AGACAGCCCC        780

GCAAGCAGCA AGCCAATTTC CATTAATTAC CGAACAGAAA TTGACAAACC ATCCATGGCA        840

GCCGGGAGCA TCACCACGCT GCCCGCCTTG CCCGAGGATG GCGGCAGCGG CGCCTTCCCG        900

CCCGGCCACT TCAAGGACCC CAAGCGGCTG TACTGCAAAA ACGGGGGCTT CTTCCTGCGC        960

ATCCACCCCG ACGGCCGAGT TGACGGGGTC CGGGAGAAGA GCGACCCTCA CATCAAGCTA       1020

CAACTTCAAG CAGAAGAGAG AGGAGTTGTG TCTATCAAAG GAGTGTGTGC TAACCGTTAC       1080

CTGGCTATGA AGGAAGATGG AAGATTACTG GCTTCTAAAT GTGTTACGGA TGAGTGTTTC       1140

TTTTTTGAAC GATTGGAATC TAATAACTAC AATACTTACC GCTCAAGGAA ATACACCAGT       1200

TGGTATGTGG CACTGAAACG AACTGGGCAG TATAAACTTG GATCCAAAAC AGGACCTGGG       1260

CAGAAAGCTA TACTTTTTCT TCCAATGTCT GCTGCTAGCG ACGAGCTTCC CCAACTGGTA       1320

ACCCTTCCAC ACCCCAATCT TCATGGACCA GAGATCTTGG ATGTTCCTTC CACA            1374

(2) INFORMATION FOR SEQ ID NO: 27:

(i) SEQUENCE CHARACTERISTICS:
        (A) LENGTH: 1416 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 27:

CCCACTGACC TGCGATTCAC CAACATTGGT CCAGACACCA TGCGTGTCAC CTGGGCTCCA         60

CCCCCATCCA TTGATTTAAC CAACTTCCTG GTGCGTTACT CACCTGTGAA AATGAGGAA        120

GATGTTGCAG AGTTGTCAAT TTCTCCTTCA GACAATGCAG TGGTCTTAAC AAATCTCCTG       180

CCTGGTACAG AATATGTAGT GAGTGTCTCC AGTGTCTACG AACAACATGA GAGCACACCT       240

CTTAGAGGAA GACAGAAAAC AGGTCTTGAT TCCCCAACTG GCATTGACTT TTCTGATATT       300

ACTGCCAACT CTTTTACTGT GCACTGGATT GCTCCTCGAG CCACCATCAC TGGCTACAGG       360

ATCCGCCATC ATCCCGAGCA CTTCAGTGGG AGACCTCGAG AAGATCGGGT GCCCCACTCT       420

CGGAATTCCA TCACCCTCAC CAACCTCACT CCAGGCACAG AGTATGTGGT CAGCATCGTT       480

GCTCTTAATG GCAGAGAGGA AAGTCCCTTA TTGATTGGCC AACAATCAAC AGTTTCTGAT       540

GTTCCGAGGG ACCTGGAAGT TGTTGCTGCG ACCCCCACCA GCCTACTGAT CAGCTGGGAT       600

GCTCCTGCTG TCACAGTGAG ATATTACAGG ATCACTTACG AGAAACAGG AGGAAATAGC        660

CCTGTCCAGG AGTTCACTGT GCCTGGGAGC AAGTCTACAG CTACCATCAG CGGCCTTAAA       720

CCTGGAGTTG ATTATACCAT CACTGTGTAT GCTGTCACTG GCCGTGGAGA CAGCCCCGCA       780

AGCAGCAAGC CAATTTCCAT TAATTACCGA ACAGAAATTG ACAAACCATC CATGGCTATT       840

CCTGCACCAA CTGACCTGAA GTTCACTCAG GTCACACCCA AGCCTGAG CGCCCAGTGG        900

ACACCACCCA ATGTTCAGCT CACTGGATAT CGAGTGCGGG TGACCCCCAA GGAGAAGACC       960

GGACCAATGA AAGAAATCAA CCTTGCTCCT GACAGCTCAT CCGTGGTTGT ATCAGGACTT      1020

ATGGTGGCCA CCAAATATGA AGTGAGTGTC TATGCTCTTA AGGACACTTT GACAAGCAGA      1080
```

```
CCAGCTCAGG GTGTTGTCAC CACTCTGGAG AATGTCAGCC CACCAAGAAG GGCTCGTGTG      1140

ACAGATGCTA CTGAGACCAC CATCACCATT AGCTGGAGAA CCAAGACTGA GACGATCACT      1200

GGCTTCCAAG TTGATGCCGT TCCAGCCAAT GGCCAGACTC CAATCCGAG AACCATCAAG      1260

CCAGATGTCA GAAGCTACAC CATCACAGGT TTACAACCAG GCACTGACTA CAAGATCTAC      1320

CTGTACACCT TGAATGACAA TGCTCGGAGC TCCCCTGTGG TCATCGACGC CTCCACTGCC      1380

ATTGATGCAC CATCCAACCT GCGTTTCCTG GCCACC                               1416
```

(2) INFORMATION FOR SEQ ID NO: 28:

(i) SEQUENCE CHARACTERISTICS:
        (A) LENGTH: 35 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 28:

```
Gly Gly Arg Gly Thr Pro Gly Lys Pro Gly Pro Arg Gly Gln Arg Gly
1               5                   10                  15

Pro Thr Gly Pro Arg Gly Glu Arg Gly Pro Arg Gly Ile Thr Gly Lys
            20                  25                  30

Pro Gly Pro
        35
```

(2) INFORMATION FOR SEQ ID NO: 29:

(i) SEQUENCE CHARACTERISTICS:
        (A) LENGTH: 302 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 29:

```
Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Pro Gly Thr Glu
        50                  55                  60

Tyr Val Val Ser Val Ser Ser Val Tyr Glu Gln His Glu Ser Thr Pro
65                      70                  75                  80

Leu Arg Gly Arg Gln Lys Thr Gly Leu Asp Ser Pro Thr Gly Ile Asp
                    85                  90                  95

Phe Ser Asp Ile Thr Ala Asn Ser Phe Thr Val His Trp Ile Ala Pro
                100                 105                 110

Arg Ala Thr Ile Thr Gly Tyr Arg Ile Arg His His Pro Glu His Phe
            115                 120                 125

Ser Gly Arg Pro Arg Glu Asp Arg Val Pro His Ser Arg Asn Ser Ile
        130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175
```

```
Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
            195                 200                 205

Tyr Arg Ile Thr Tyr Gly Glu Thr Gly Gly Asn Ser Pro Val Gln Glu
            210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Asp Glu Leu Pro Gln Leu Val Thr Leu Pro His
            275                 280                 285

Pro Asn Leu His Gly Pro Glu Ile Leu Asp Val Pro Ser Thr
            290                 295                 300

(2) INFORMATION FOR SEQ ID NO: 30:

(i) SEQUENCE CHARACTERISTICS:
        (A) LENGTH: 573 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 30:

Met Ala Ala Ser Ala Ile Pro Ala Pro Thr Asp Leu Lys Phe Thr Gln
1               5                   10                  15

Val Thr Pro Thr Ser Leu Ser Ala Gln Trp Thr Pro Pro Asn Val Gln
            20                  25                  30

Leu Thr Gly Tyr Arg Val Arg Val Thr Pro Lys Glu Lys Thr Gly Pro
            35                  40                  45

Met Lys Glu Ile Asn Leu Ala Pro Asp Ser Ser Val Val Val Ser
50                  55                  60

Gly Leu Met Val Ala Thr Lys Tyr Glu Val Ser Val Tyr Ala Leu Lys
65                  70                  75                  80

Asp Thr Leu Thr Ser Arg Pro Ala Gln Gly Val Val Thr Thr Leu Glu
            85                  90                  95

Asn Val Ser Pro Pro Arg Arg Ala Arg Val Thr Asp Ala Thr Glu Thr
            100                 105                 110

Thr Ile Thr Ile Ser Trp Arg Thr Lys Thr Glu Thr Ile Thr Gly Phe
            115                 120                 125

Gln Val Asp Ala Val Pro Ala Asn Gly Gln Thr Pro Ile Gln Arg Thr
            130                 135                 140

Ile Lys Pro Asp Val Arg Ser Tyr Thr Ile Thr Gly Leu Gln Pro Gly
145                 150                 155                 160

Thr Asp Tyr Lys Ile Tyr Leu Tyr Thr Leu Asn Asp Asn Ala Arg Ser
                165                 170                 175

Ser Pro Val Val Ile Asp Ala Ser Thr Ala Ile Asp Ala Pro Ser Asn
            180                 185                 190

Leu Arg Phe Leu Ala Thr Thr Pro Asn Ser Leu Leu Val Ser Trp Gln
            195                 200                 205

Pro Pro Arg Ala Arg Ile Thr Gly Tyr Ile Ile Lys Tyr Glu Lys Pro
            210                 215                 220
```

```
Gly Ser Pro Pro Arg Glu Val Val Pro Arg Pro Arg Pro Gly Val Thr
225                 230                 235                 240

Glu Ala Thr Ile Thr Gly Leu Glu Pro Gly Thr Glu Tyr Thr Ile Tyr
            245                 250                 255

Val Ile Ala Leu Lys Asn Asn Gln Lys Ser Glu Pro Leu Ile Gly Arg
            260                 265                 270

Lys Lys Thr Ala Ile Pro Ala Pro Thr Asp Leu Lys Phe Thr Gln Val
            275                 280                 285

Thr Pro Thr Ser Leu Ser Ala Gln Trp Thr Pro Pro Asn Val Gln Leu
290                 295                 300

Thr Gly Tyr Arg Val Arg Val Thr Pro Lys Glu Lys Thr Gly Pro Met
305                 310                 315                 320

Lys Glu Ile Asn Leu Ala Pro Asp Ser Ser Val Val Val Ser Gly
            325                 330                 335

Leu Met Val Ala Thr Lys Tyr Glu Val Ser Val Tyr Ala Leu Lys Asp
            340                 345                 350

Thr Leu Thr Ser Arg Pro Ala Gln Gly Val Val Thr Thr Leu Glu Asn
            355                 360                 365

Val Ser Pro Pro Arg Arg Ala Arg Val Thr Asp Ala Thr Glu Thr Thr
370                 375                 380

Ile Thr Ile Ser Trp Arg Thr Lys Thr Glu Thr Ile Thr Gly Phe Gln
385                 390                 395                 400

Val Asp Ala Val Pro Ala Asn Gly Gln Thr Pro Ile Gln Arg Thr Ile
                405                 410                 415

Lys Pro Asp Val Arg Ser Tyr Thr Ile Thr Gly Leu Gln Pro Gly Thr
            420                 425                 430

Asp Tyr Lys Ile Tyr Leu Tyr Thr Leu Asn Asp Asn Ala Arg Ser Ser
            435                 440                 445

Pro Val Val Ile Asp Ala Ser Thr Ala Ile Asp Ala Pro Ser Asn Leu
450                 455                 460

Arg Phe Leu Ala Thr Thr Pro Asn Ser Leu Leu Val Ser Trp Gln Pro
465                 470                 475                 480

Pro Arg Ala Arg Ile Thr Gly Tyr Ile Ile Lys Tyr Glu Lys Pro Gly
                485                 490                 495

Ser Pro Pro Arg Glu Val Val Pro Arg Pro Arg Pro Gly Val Thr Glu
            500                 505                 510

Ala Thr Ile Thr Gly Leu Glu Pro Gly Thr Glu Tyr Thr Ile Tyr Val
            515                 520                 525

Ile Ala Leu Lys Asn Asn Gln Lys Ser Glu Pro Leu Ile Gly Arg Lys
530                 535                 540

Lys Thr Ser Asp Glu Leu Pro Gln Leu Val Thr Leu Pro His Pro Asn
545                 550                 555                 560

Leu His Gly Pro Glu Ile Leu Asp Val Pro Ser Thr Ser
                565                 570

(2) INFORMATION FOR SEQ ID NO: 31:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 31:
```

AAACCATGGC AGCTAGCAAT GTCAGCCCAC CAAGAAG                                37

(2) INFORMATION FOR SEQ ID NO: 32:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 32:

AAAGGATCCC TAACTAGTGG AAGGAACATC CAAGATC                                37

(2) INFORMATION FOR SEQ ID NO: 33:

(i) SEQUENCE CHARACTERISTICS:
        (A) LENGTH: 1722 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 33:

ATGGCAGCTA GCGCTATTCC TGCACCAACT GACCTGAAGT TCACTCAGGT CACACCCACA        60

AGCCTGAGCG CCCAGTGGAC ACCACCCAAT GTTCAGCTCA CTGGATATCG AGTGCGGGTG       120

ACCCCCAAGG AGAAGACCGG ACCAATGAAA GAAATCAACC TTGCTCCTGA CAGCTCATCC       180

GTGGTTGTAT CAGGACTTAT GGTGGCCACC AAATATGAAG TGAGTGTCTA TGCTCTTAAG       240

GACACTTTGA CAAGCAGACC AGCTCAGGGT GTTGTCACCA CTCTGGAGAA TGTCAGCCCA       300

CCAAGAAGGG CTCGTGTGAC AGATGCTACT GAGACCACCA TCACCATTAG CTGGAGAACC       360

AAGACTGAGA CGATCACTGG CTTCCAAGTT GATGCCGTTC CAGCCAATGG CCAGACTCCA       420

ATCCAGAGAA CCATCAAGCC AGATGTCAGA AGCTACACCA TCACAGGTTT ACAACCAGGC       480

ACTGACTACA AGATCTACCT GTACACCTTG AATGACAATG CTCGGAGCTC CCCTGTGGTC       540

ATCGACGCCT CCACTGCCAT TGATGCACCA TCCAACCTGC GTTTCCTGGC CACCACACCC       600

AATTCCTTGC TGGTATCATG GCAGCCGCCA CGTGCCAGGA TTACCGGCTA CATCATCAAG       660

TATGAGAAGC CTGGGTCTCC TCCCAGAGAA GTGGTCCCTC GGCCCCGCCC TGGTGTCACA       720

GAGGCTACTA TTACTGGCCT GGAACCGGGA ACCGAATATA CAATTTATGT CATTGCCCTG       780

AAGAATAATC AGAAGAGCGA GCCCCTGATT GGAAGGAAAA AGACTAGCGC TATTCCTGCA       840

CCAACTGACC TGAAGTTCAC TCAGGTCACA CCCACAAGCC TGAGCGCCCA GTGGACACCA       900

CCCAATGTTC AGCTCACTGG ATATCGAGTG CGGGTGACCC CCAAGGAGAA GACCGGACCA       960

ATGAAAGAAA TCAACCTTGC TCCTGACAGC TCATCCGTGG TTGTATCAGG ACTTATGGTG      1020

GCCACCAAAT ATGAAGTGAG TGTCTATGCT CTTAAGGACA CTTTGACAAG CAGACCAGCT      1080

CAGGGTGTTG TCACCACTCT GGAGAATGTC AGCCCACCAA GAAGGGCTCG TGTGACAGAT      1140

GCTACTGAGA CCACCATCAC CATTAGCTGG AGAACCAAGA CTGAGACGAT CACTGGCTTC      1200

CAAGTTGATG CCGTTCCAGC CAATGGCCAG ACTCCAATCC AGAGAACCAT CAAGCCAGAT      1260

GTCAGAAGCT ACACCATCAC AGGTTTACAA CCAGGCACTG ACTACAAGAT CTACCTGTAC      1320

ACCTTGAATG ACAATGCTCG GAGCTCCCCT GTGGTCATCG ACGCCTCCAC TGCCATTGAT      1380

GCACCATCCA ACCTGCGTTT CCTGGCCACC ACACCCAATT CCTTGCTGGT ATCATGGCAG      1440

```
CCGCCACGTG CCAGGATTAC CGGCTACATC ATCAAGTATG AGAAGCCTGG GTCTCCTCCC      1500

AGAGAAGTGG TCCCTCGGCC CCGCCCTGGT GTCACAGAGG CTACTATTAC TGGCCTGGAA      1560

CCGGGAACCG AATATACAAT TTATGTCATT GCCCTGAAGA ATAATCAGAA GAGCGAGCCC      1620

CTGATTGGAA GGAAAAAGAC TAGCGACGAG CTTCCCCAAC TGGTAACCCT TCCACACCCC      1680

AATCTTCATG GACCAGAGAT CTTGGATGTT CCTTCCACTA GT                        1722

(2) INFORMATION FOR SEQ ID NO: 34:

(i) SEQUENCE CHARACTERISTICS:
        (A) LENGTH: 412 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 34:

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Ile Glu Gly
    210                 215                 220

Arg Gly Ile Pro Arg Asn Ser Gly Ala Pro Arg Leu Ile Cys Asp
225                 230                 235                 240

Ser Arg Val Leu Gln Arg Tyr Leu Leu Glu Ala Lys Glu Ala Glu Asn
                245                 250                 255

Ile Thr Thr Gly Cys Ala Glu His Cys Ser Leu Asn Glu Asn Ile Thr
            260                 265                 270

Val Pro Asp Thr Lys Val Asn Phe Tyr Ala Trp Lys Arg Met Glu Val
        275                 280                 285

Gly Gln Gln Ala Val Glu Val Trp Gln Gly Leu Ala Leu Leu Ser Glu
    290                 295                 300
```

```
Ala Val Leu Arg Gly Gln Ala Leu Leu Val Asn Ser Ser Gln Pro Trp
305                 310                 315                 320

Glu Pro Leu Gln Leu His Val Asp Lys Ala Val Ser Gly Leu Arg Ser
            325                 330                 335

Leu Thr Thr Leu Leu Arg Ala Leu Gly Ala Gln Lys Glu Ala Ile Ser
            340                 345                 350

Pro Pro Asp Ala Ala Ser Ala Ala Pro Leu Arg Thr Ile Thr Ala Asp
            355                 360                 365

Thr Phe Arg Lys Leu Phe Arg Val Tyr Ser Asn Phe Leu Arg Gly Lys
        370                 375                 380

Leu Lys Leu Tyr Thr Gly Glu Ala Cys Arg Thr Gly Asp Arg Leu Ala
385                 390                 395                 400

Met Asp Pro Leu Glu Ser Thr Arg Ala Ala Ala Ser
            405                 410
```

(2) INFORMATION FOR SEQ ID NO: 35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 35:

GCTCCCTCTG GGCCTCCCAG TCCT                                          24

(2) INFORMATION FOR SEQ ID NO: 36:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 36:

GTTGGTGAGG GAGGTGGTGG ATAT                                          24

(2) INFORMATION FOR SEQ ID NO: 37:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 37:

GGCCTCCCGA ATTCCGGTGC CCCACCACGC CTC                               33

(2) INFORMATION FOR SEQ ID NO: 38:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 38:

```
CCCACGTGGA TCCATGGCTA ATCTGTCCCC TGT                             33

(2) INFORMATION FOR SEQ ID NO: 39:

(i) SEQUENCE CHARACTERISTICS:
        (A) LENGTH: 1239 base pairs
        (B) TYPE: nucleic acid
        (C) STRANDEDNESS: double
        (D) TOPOLOGY: linear (ii) MOLECULE TYPE: DNA (xi) SEQUENCE DESCRIPTION: SEQ ID NO: 39:

ATGTCCCCTA TACTAGGTTA TTGGAAAATT AAGGGCCTTG TGCAACCCAC TCGACTTCTT   60

TTGGAATATC TTGAAGAAAA ATATGAAGAG CATTTGTATG AGCGCGATGA AGGTGATAAA  120

TGGCGAAACA AAAGTTTGA ATTGGGTTTG GAGTTTCCCA ATCTTCCTTA TTATATTGAT  180

GGTGATGTTA AATTAACACA GTCTATGGCC ATCATACGTT ATATAGCTGA CAAGCACAAC  240

ATGTTGGGTG GTTGTCCAAA AGAGCGTGCA GAGATTTCAA TGCTTGAAGG AGCGGTTTTG  300

GATATTAGAT ACGGTGTTTC GAGAATTGCA TATAGTAAAG ACTTTGAAAC TCTCAAAGTT  360

GATTTTCTTA GCAAGCTACC TGAAATGCTG AAAATGTTCG AAGATCGTTT ATGTCATAAA  420

ACATATTTAA ATGGTGATCA TGTAACCCAT CCTGACTTCA TGTTGTATGA CGCTCTTGAT  480

GTTGTTTTAT ACATGGACCC AATGTGCCTG GATGCGTTCC CAAAATTAGT TTGTTTTAAA  540

AAACGTATTG AAGCTATCCC ACAAATTGAT AAGTACTTGA AATCCAGCAA GTATATAGCA  600

TGGCCTTTGC AGGGCTGGCA AGCCACGTTT GGTGGTGGCG ACCATCCTCC AAAATCGGAT  660

CTGATCGAAG GTCGTGGGAT CCCCAGGAAT TCCGGTGCCC CACCACGCCT CATCTGTGAC  720

AGCCGAGTCC TGCAGAGGTA CCTCTTGGAG GCCAAGGAGG CCGAGAATAT CACGACGGGC  780

TGTGCTGAAC ACTGCAGCTT GAATGAGAAT ATCACTGTCC CAGACACCAA AGTTAATTTC  840

TATGCCTGGA AGAGGATGGA GGTCGGGCAG CAGGCCGTAG AAGTCTGGCA GGGCCTGGCC  900

CTGCTGTCGG AAGCTGTCCT GCGGGGCCAG GCCCTGTTGG TCAACTCTTC CCAGCCGTGG  960

GAGCCCCTGC AGCTGCATGT GGATAAAGCC GTCAGTGGCC TTCGCAGCCT CACCACTCTG 1020

CTTCGGGCTC TGGGAGCCCA GAAGGAAGCC ATCTCCCCTC CAGATGCGGC CTCAGCTGCT 1080

CCACTCCGAA CAATCACTGC TGACACTTTC CGCAAACTCT TCCGAGTCTA CTCCAATTTC 1140

CTCCGGGGAA AGCTGAAGCT GTACACAGGG GAGGCCTGCA GGACAGGGGA CAGATTAGCC 1200

ATGGATCCTC TAGAGTCGAC TCGAGCGGCC GCATCGTGA                       1239
```